United States Patent
McMahon

(10) Patent No.: US 11,357,230 B2
(45) Date of Patent: Jun. 14, 2022

(54) HERBICIDAL AMIDES

(71) Applicant: FMC Corporation, Philadelphia, PA (US)

(72) Inventor: Travis Chandler McMahon, Middletown, DE (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 16/614,870

(22) PCT Filed: May 30, 2018

(86) PCT No.: PCT/US2018/035015
§ 371 (c)(1),
(2) Date: Nov. 19, 2019

(87) PCT Pub. No.: WO2018/222646
PCT Pub. Date: Dec. 6, 2018

(65) Prior Publication Data
US 2020/0154709 A1    May 21, 2020

Related U.S. Application Data

(60) Provisional application No. 62/512,683, filed on May 30, 2017.

(51) Int. Cl.
*A01N 43/36* (2006.01)
*C07D 207/277* (2006.01)

(52) U.S. Cl.
CPC ......... *A01N 43/36* (2013.01); *C07D 207/277* (2013.01)

(58) Field of Classification Search
None
See application file for complete search history.

(56) References Cited

U.S. PATENT DOCUMENTS

| | | | |
|---|---|---|---|
| 3,741,989 A | 6/1973 | Zaugg | |
| 3,959,481 A | 5/1976 | Davis et al. | |
| 4,594,094 A | 6/1986 | Kollmeyer | |
| 4,874,422 A | 10/1989 | Woolard | |
| 5,196,534 A | 3/1993 | Whitehead et al. | |
| 5,856,273 A | 1/1999 | Kay et al. | |
| 7,205,318 B2 | 4/2007 | Qiao et al. | |
| 7,355,053 B2 | 4/2008 | Reinhard et al. | |
| 7,375,232 B2 | 5/2008 | Clark et al. | |
| 8,293,926 B2 | 10/2012 | Yasuoka et al. | |
| 8,461,202 B2 | 6/2013 | Sancho Sanz et al. | |
| 8,575,154 B2 | 11/2013 | Kori et al. | |
| 8,946,216 B2 | 2/2015 | Deng et al. | |
| 9,119,397 B2 | 9/2015 | Yerkes et al. | |
| 9,446,995 B2 | 9/2016 | Chong | |
| 9,737,073 B2 | 8/2017 | Gifford et al. | |
| 9,944,602 B2 | 4/2018 | Satterfield et al. | |
| 9,969,728 B2 | 5/2018 | Defays et al. | |
| 10,227,286 B2 | 3/2019 | Satterfield | |
| 10,294,202 B2 | 5/2019 | Satterfield et al. | |
| 10,405,547 B2 | 9/2019 | Satterfield et al. | |
| 10,442,807 B2 | 10/2019 | Campbell et al. | |
| 10,582,709 B2 * | 3/2020 | Stevenson | A01N 43/74 |
| 10,906,873 B2 * | 2/2021 | Campbell | C07D 413/06 |
| 2004/0242671 A1 | 12/2004 | Grimee et al. | |
| 2007/0123508 A1 | 5/2007 | Olsson et al. | |
| 2009/0062366 A1 | 3/2009 | Hachiya et al. | |
| 2009/0203694 A1 | 8/2009 | Hurley et al. | |
| 2011/0218199 A1 | 9/2011 | Georges et al. | |
| 2015/0173371 A1 | 6/2015 | Mann et al. | |
| 2016/0137639 A1 | 5/2016 | Kotoku et al. | |
| 2018/0049437 A1 | 2/2018 | Satterfield et al. | |
| 2018/0057442 A1 | 3/2018 | Satterfield | |
| 2018/0077931 A1 | 3/2018 | Stevenson et al. | |
| 2018/0099935 A1 | 4/2018 | Satterfield et al. | |
| 2018/0141904 A1 | 5/2018 | Campbell et al. | |
| 2018/0213788 A1 | 8/2018 | Satterfield et al. | |
| 2020/0010446 A1 | 1/2020 | Chen | |
| 2020/0115337 A1 | 4/2020 | Campbell | |
| 2020/0120931 A1 | 4/2020 | Campbell | |

FOREIGN PATENT DOCUMENTS

| | | |
|---|---|---|
| CN | 102531918 | 10/2013 |
| DE | 1262277 | 3/1968 |
| EP | 2336104 | 6/2011 |
| IN | 1462DEL08 | 6/2008 |
| JP | 53-056288 | 5/1978 |
| JP | 54-088114 | 7/1979 |
| JP | 08-269145 | 10/1996 |
| KR | 20130142477 | 12/2013 |
| RU | 2555370 | 7/2015 |

(Continued)

OTHER PUBLICATIONS

Cambridge medchem "Carbonyl bioisosteres" (http://web.archive.org/web/20130113041908/https://www.cambridgemedchemconsulting.com/resources/bioisosteres/carbonyl_bioisosteres.html) (Year: 2013).*
Patani et al. (Chem. Rev., 1996, 96, 3147-3176) (Year: 1996).*
International Search Report from co-pending PCT/US2018/035015 application dated Jul. 17, 2018.
(Continued)

*Primary Examiner* — Erin E Hirt
(74) *Attorney, Agent, or Firm* — Reed A Coats; FMC Corporation

(57) ABSTRACT

Disclosed are compounds of Formula 1, including all stereoisomers, N-oxides, and salts thereof

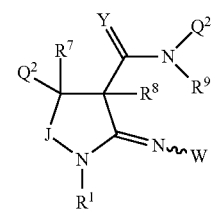

wherein W, $R^1$, J, $Q^1$, $R^7$, $R^8$, Y, $R^9$ and are as defined in the disclosure.

Also disclosed are compositions containing the compounds of Formula 1 and methods for controlling undesired vegetation comprising contacting the undesired vegetation or its environment with an effective amount of a compound or a composition of the invention.

12 Claims, No Drawings

(56) References Cited

FOREIGN PATENT DOCUMENTS

| WO | 200009481 | 2/2000 |
|---|---|---|
| WO | 2002/006512 | 1/2002 |
| WO | 2003/024222 | 3/2003 |
| WO | 2004046081 | 6/2004 |
| WO | 2006081562 | 8/2006 |
| WO | 2006/127396 | 11/2006 |
| WO | 2009062371 | 5/2009 |
| WO | 20120034957 | 3/2012 |
| WO | 20150084796 | 6/2015 |
| WO | 20160003997 | 1/2016 |
| WO | 20160094117 | 6/2016 |
| WO | 20160164201 | 10/2016 |
| WO | 2016182780 | 11/2016 |
| WO | 20160176082 | 11/2016 |
| WO | 20160196019 | 12/2016 |
| WO | 20160196593 | 12/2016 |
| WO | 20170023515 | 2/2017 |
| WO | 2017075559 | 5/2017 |
| WO | 2018/065311 | 4/2018 |
| WO | 20180118384 | 6/2018 |
| WO | 20180175231 | 9/2018 |
| WO | 2018175226 | 12/2018 |
| WO | 2018222647 | 12/2018 |

OTHER PUBLICATIONS

Murata et al.; "Oxidation of N-Acyl-Pyrrolidines and -Piperidines with Iron(II)-Hydrogen Peroxide and an Iron Complex-Molecular Oxygen"; J. Chem. Soc. Perkin Trans.; 1987; 1259-1262. (XP055297105).

Banerjee et al., "A Stereoselective Cyclization Strategy for the Preparation of gamma-Lactams and Their Use in the Synthesis of alpha-Methyl-beta-Proline", J. Org. Chem. 2012, vol. 77, pp. 10925-10930.

Campaigne et el.; Synthesis of Some Ureidodihydrofurans and Related Pyrimidones as Potential Antimalarials; J. Med. Chem.; 1969; 339-342 (XP002278920).

Cauliez et al.; "Studies on Pyrrolidinones. On the Carbamoylation of Some Pyroglutamic Derivatives"; J. Het. Chem.; 33; 1996; 1233-1237. (XP055297107).

Hajra, S. et al., "Organocatalytic Enantioselective Conjugate Addition of Nitromethane to Alkylidinemalonates: Asymmetric Synthesis of Pyrrolidine-3-Carboxylic Acid Derivatives", RSC Advances, 2013, 3, 10185-10188.

Hwang et al.; "Diastereoselective Synthesis of Oxazolidinone Derivatives and Their Antifungal Activities"; Korean J. of Med. Chem.; vol. 4, No. 1; 1994; 52-56. (XP009191451).

IPCOM000241978D; Jun. 11, 2015.

PubChem Entry CID 29937915 (4S)-4-[3-(trifluoromethyl)phenyl]pyrrolidin-2-one: May 28, 2009.

Wang et al., "Asymmetric Cyanation of Activated Olefins with Ethyl Cyanoformate Catalyzed by a Modular Titanium Catalyst", Org. Lett., 2010, vol. 12(6), pp. 1280-1283.

XP002734980; Jan. 20, 2002.

XP002734981; WO0009481; Feb. 24, 2000.

XP002759805; Jan. 20, 2002.

XP002759806; Mar. 23, 2009.

CN Decision, "Invalidation Request Examination Decision," in CN Appln. No. 201480074726.8, dated Apr. 20, 2021, 23 pages.

CN Opposition, "Request for Invalidation of a Patent Right," in CN Appln No. 201480074726.8, dated Sep. 9, 2020, 49 pages (English Translation).

CN Support, "Declaration of Aman Chandi," in CN Appln. No. 201480074726.8, dated Dec. 18, 2020, 9 pages.

CN Support, "Declaration of Steven Gutteridge," in CN Appln. No. 201480074726.8, dated Dec. 18, 2020, 5 pages.

CN Support, "Declaration of Steven Gutteridge," in CN Appln. No. 201480074726.8, dated Feb. 10, 2021, 5 pages.

EP Opposition Response, "Auxiliary Request 1—marked up," in EP Appln No. 14815174.9, from response dated Jun. 25, 2021, 10 pages.

EP Opposition Response, "Auxiliary Request 1," in EP Appln No. 14815174.9, from response dated Jun. 25, 2021, 10 pages.

EP Opposition Response, "Auxiliary Request 2—marked up," in EP Appln No. 14815174.9, from response dated Jun. 25, 2021, 10 pages.

EP Opposition Response, "Auxiliary Request 2," in EP Appln No. 14815174.9, from response dated Jun. 25, 2021, 10 pages.

EP Opposition Response, "Auxiliary Request 3—marked up," in EP Appln No. 14815174.9, from response dated Jun. 25, 2021, 10 pages.

EP Opposition Response, "Auxiliary Request 3," in EP Appln No. 14815174.9, from response dated Jun. 25, 2021, 9 pages.

EP Opposition Response, "Auxiliary Request 4—marked up," in EP Appln No. 14815174.9, from response dated Jun. 25, 2021, 10 pages.

EP Opposition Response, "Auxiliary Request 4," in EP Appln No. 14815174.9, from response dated Jun. 25, 2021, 9 pages.

EP Opposition Response, "Auxiliary Request 5—marked up," in EP Appln No. 14815174.9, from response dated Jun. 25, 2021, 11 pages.

EP Opposition Response, "Auxiliary Request 5," in EP Appln No. 14815174.9, from response dated Jun. 25, 2021, 7 pages.

EP Opposition Response, "Data testing herbicidal activity of compounds IC1*, IC3* andIC6 against plants," Exhibit D16 in EP Appln No. 14815174.9, from response dated Jun. 25, 2021, 5 pages.

EP Opposition Response, "Experimental data for further compounds," Exhibit D19 in EP Appln. No. 14815174.9, from response dated Jun. 25, 2021, 9 pages.

EP Opposition Response, "HRAC Mode of Action Classification 2021," Exhibit D21 in EP Appln. No. 14815174.9, from response dated Jun. 25, 2021, 2 pages.

EP Opposition Response, "Press Release—Novel herbicide tetflupyrolimet from FMC Corporation granted a new mode of action classification," Exhibit D20 in EP Appln. No 14815174 9, dated Apr. 8, 2021, 3 pages.

EP Opposition Response, "Submission In Opposition Proceedings—FMC," in EP Appln. No. 14815174.9, dated Jun. 25, 2021, 43 pages.

EP Opposition, "Cudney—Why Herbicides Are Selective," Exhibit D22 in EP Appln. No. 14815174.9, 1996 Symposium Proceedings, 3 pages.

EP Opposition, "English translation of the second amendments based on granted claims in CNIPA Decision," Exhibit D28 in EP Appln. No. 14815174.9, dated Apr. 15, 2021, 3 pages.

EP Opposition, "Notice of Opposition to a European Patent," in EP Appln. No. 14815174.9, dated Aug. 31, 2020, 55 pages.

EP Opposition, "Smith—Organic Chemistry, An Acid-Base Approach," Exhibit D25 in EP Appln. No. 14815174.9, CRC Press, Taylor & Francis Group, LLC, 2011, pp. 24-32, 23 pages.

EP Opposition, "Submission In Opposition Proceedings—Syngenta," in EP Appln. No. 14815174.9, dated Nov. 5, 2020, 68 pages.

EP Opposition, "Summons to Attend Oral Proceedings Pursuant to Rule 115(1) EPC," in EP Appln. No. 14815174.9, dated Jul. 16, 2021, 14 pages.

EP Opposition, "TechLine Invasive Plant News—Factors Affecting Herbicide Performance," Exhibit D23 in EP Appln. No. 14815174.9, dated Jun. 2019, 9 pages.

EP Opposition, "US-PTAB Decision in relation to U.S. Pat. No. 10,294,202 B2," Exhibit D30 in EP Appln. No. 14815174.9, dated Aug. 31, 2021, 66 pages.

EP Opposition, "Walsh—Enzymatic Reaction Mechanisms," Exhibit D26 in EP Appln. No. 14815174.9, W. H. Freeman and Company, 1979, Chapter 2, pp. 24-48, 27 pages.

EP Opposition, "Williams—Opportunities for Chiral Agrochemicals," Exhibit D24 in EP Appln. No. 14815174.9, Pestic. Sci., 1996, 46:3-9.

EP Opposition, "Written Submission," in EP Appln. No. 14815174.9, dated Dec. 14, 2021, 3 pages.

EP Opposition, "Written Submission," in EP Appln. No. 14815174.9, dated Dec. 7, 2021, 2 pages.

(56) References Cited

OTHER PUBLICATIONS

EP Opposition, "Written Submission," in EP Appln. No. 14815174.9, dated Nov. 25, 2021, 32 pages.
EP Opposition, "Written Submission," in EP Appln. No. 14815174.9, dated Nov. 30, 2021, 6 pages.
IN Opposition, "Declaration of Dhaval Dayabhai Diyora," in IN Appln. No. 201617018886, dated Jun. 1, 2016, 60 pages.
Smirnova et al., "Optical Isomerism and Biological Activity of Pharmaceutical Preparations", Moscow University Chemistry Bulletin, vol. 67, No. 3, 2012, pp. 95-102.

* cited by examiner

HERBICIDAL AMIDES

FIELD OF THE INVENTION

This invention relates to certain herbicidal amides, their (N-oxides,) salts and compositions, and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action. WO 2015/084796, WO 2016/003997 and WO 2016/196593 disclose certain herbicidal amides. The herbicidal amides of the present invention are not disclosed in these publications.

SUMMARY OF THE INVENTION

This disclosure relates, in part, to a compound of Formula 1, including all stereoisomers and N-oxides of such compounds, and salts of such compounds, stereoisomers and N-oxides:

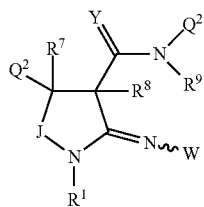

1 wherein
W is —$NR^A R^B$ or —$OR^C$;
$R^A$ is H, cyano, CHO, $C_2$-$C_4$ alkylcarbonyl, $C_1$-$C_4$ alkyl; or phenyl substituted or unsubstituted with halogen or $C_1$-$C_4$ alkyl;
$R^B$ is H, cyano, hydroxy, CHO, $C_1$-$C_6$ alkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl or $C_3$-$C_{10}$ trialkylsilyl; or a phenyl ring or a naphthalenyl ring system, each ring or ring system substituted or unsubstituted with up to 5 substituents independently selected from $R^{16}$; or a 4- to 7-membered heterocyclic ring, substituted or unsubstituted on ring members with up to 5 substituents independently selected from $R^{16}$; or
$R^A$ and $R^B$ are taken together along with the nitrogen atom to which they are both bonded to form a 4-, 5- or 6-membered ring containing ring members selected from carbon, oxygen, nitrogen and —C(=O)—; or taken together as a 6- to 10-membered bicyclic ring system; or taken together as an 8- to 13-membered tricyclic ring system, each ring or ring system containing ring members selected from carbon, nitrogen and —C(=O)— and substituted or unsubstituted with halogen, cyano or $C_1$-$C_4$ alkyl;
$R^C$ is $C_1$-$C_4$ haloalkyl, $C_2$-$C_4$ haloalkylcarbonyl, $C_3$-$C_6$ cycloalkyl; or phenyl substituted or unsubstituted with halogen, cyano or $C_1$-$C_4$ alkyl; or a 6-membered nitrogen containing aromatic ring substituted or unsubstituted with halogen, cyano or $C_1$-$C_4$ alkyl;
J is —$CR^2R^3$—, —$CR^2R^3$—$CR^4R^5$—, —$NR^6$— or —O— (i.e. where the bond projecting to the left is connected to $NR^1$);
Y is O, S or $NR^{15}$;
$R^1$ is H, hydroxy, amino, cyano, CHO, $C_3$-$C_8$ alkylcarbonylalkyl, —C($C_1$-$C_4$ alkyl)=N—O($C_1$-$C_4$ alkyl), —C(O)$NH_2$, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl, $C_3$-$C_8$ cycloalkenyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkenylalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_5$-$C_{10}$ cycloalkylcarbonylalkyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl; or —CPh=N—O($C_1$-$C_4$ alkyl) where the phenyl is substituted or unsubstituted with up to 5 substituents independently selected from $R^{13}$; or $G^1$;
$Q^1$ is a phenyl ring or a naphthalenyl ring system, each ring or ring system substituted or unsubstituted with up to 5 substituents independently selected from $R^{10}$; or a 4- to 7-membered heterocyclic ring; or an 8- to 10-membered bicyclic ring system, each ring or ring system containing ring members selected from carbon atoms and 1 to 5 heteroatoms independently selected from up to 2 O, up to 2 S and up to 5 N atoms, wherein up to 3 carbon ring members are independently selected from C(=O) and C(=S), and the sulfur atom ring members are independently selected from S(=O)$_u$ (=$NR^{14}$)$_v$, each ring or ring system substituted or unsubstituted with up to 5 substituents independently selected from $R^{10}$ on carbon atom ring members and selected from $R^{12}$ on nitrogen atom ring members;
$Q^2$ is a phenyl ring or a naphthalenyl ring system, each ring or ring system substituted or unsubstituted with up to 5 substituents independently selected from $R^{11}$; or a 4- to 7-membered heterocyclic ring; or an 8- to 10-membered bicyclic ring system, each ring or ring system containing ring members selected from carbon atoms and 1 to 4 heteroatoms independently selected from up to 2 O, up to 2 S and up to 5 N atoms, wherein up to 3 carbon ring members are independently selected from C(=O) and C(=S), and the sulfur atom ring members are independently selected from $S(=O)_u$ $(=NR^{14})_v$, each ring or ring system substituted or unsubstituted with up to 5 substituents independently selected from $R^{11}$ on carbon atom ring members and selected from $R^{13}$ on nitrogen atom ring members;

$R^2$ and $R^3$ are each independently H, halogen, hydroxy, $C_1$-$C_4$ alkyl, $C_1$-$C_4$ haloalkyl or $C_1$-$C_4$ alkoxy; or $R^2$ and $R^3$ are taken together with the carbon atom to which they are bonded to form a $C_3$-$C_7$ cycloalkyl ring;

$R^4$ and $R^5$ are each independently H, halogen, hydroxy, $C_1$-$C_4$ alkyl, $C_1$-$C_4$ haloalkyl or $C_1$-$C_4$ alkoxy;

$R^6$ is $C_1$-$C_6$ alkyl, $C_2$-$C_6$ alkenyl, $C_3$-$C_6$ alkynyl or $C_1$-$C_6$ alkoxy; or $R^1$ and $R^6$ are taken together as $C_3$-$C_6$ alkylene or —$CH_2OCH_2$—;

$R^7$ and $R^8$ are each independently H, halogen, hydroxy, $C_1$-$C_4$ alkoxy, $C_1$-$C_4$ haloalkyl or $C_1$-$C_4$ alkyl;

$R^9$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl or $C_3$-$C_{10}$ trialkylsilyl; or $G^1$;

each $R^{10}$ and $R^{11}$ is independently halogen, hydroxy, cyano, nitro, amino, $C_1$-$C_8$ alkyl, $C_1$-$C_8$ cyanoalkyl, $C_1$-$C_8$ cyanoalkoxy, $C_1$-$C_8$ haloalkyl, $C_1$-$C_8$ hydroxyalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkynyl, $C_2$-$C_8$ haloalkynyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkoxyhaloalkoxy, $C_3$-$C_6$ cycloalkyl, cyclopropylmethyl, 1-methylcyclopropyl, 2-methylcyclopropyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylamino, $C_2$-$C_8$ dialkylamino, $C_2$-$C_8$ halodialkylamino, $C_2$-$C_8$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_2$-$C_8$ alkylaminocarbonyl, $C_4$-$C_{10}$ cycloalkylaminocarbonyl, $C_3$-$C_{10}$ dialkylaminocarbonyl, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, formylamino, $C_2$-$C_8$ alkylcarbonylamino, $C_2$-$C_8$ haloalkylcarbonylamino, $C_3$-$C_8$ cycloalkylamino, $C_2$-$C_8$ alkoxycarbonylamino, $C_1$-$C_6$ alkylsulfonylamino, $C_1$-$C_6$ haloalkylsulfonylamino, —SF$_5$, —SCN, SO$_2$NH$_2$, $C_3$-$C_{12}$ trialkylsilyl, $C_4$-$C_{12}$ trialkylsilylalkyl or $C_4$-$C_{12}$ trialkylsilylalkoxy; or $G^2$; or $R^{20}S(=O)=N$—, $R^{20}S(=O)_2NR^{19}$—C(=O)— or $R^{20}(R^{19}N=)_qS(=O)_p$—, wherein the free bond projecting to the right indicates the connecting point to $Q^1$;

each $R^{12}$ and $R^{13}$ is independently cyano, $C_1$-$C_3$ alkyl, $C_1$-$C_8$ hydroxyalkyl, $C_2$-$C_3$ alkenyl, $C_2$-$C_3$ alkynyl, $C_3$-$C_6$ cycloalkyl, $C_2$-$C_3$ alkoxyalkyl, $C_1$-$C_3$ alkoxy, $C_2$-$C_3$ alkylcarbonyl, $C_2$-$C_3$ alkoxycarbonyl, $C_2$-$C_3$ alkylaminoalkyl or $C_3$-$C_4$ dialkylaminoalkyl;

each $R^{14}$ is independently H, cyano, $C_2$-$C_3$ alkylcarbonyl or $C_2$-$C_3$ haloalkylcarbonyl;

$R^{15}$ is H, cyano, hydroxy, CHO, $C_1$-$C_4$ alkyl, $C_1$-$C_4$ haloalkyl, $C_1$-$C_4$ alkoxy, $C_2$-$C_6$ alkylcarbonyl or $C_2$-$C_6$ haloalkylcarbonyl;

each $G^1$ is independently phenyl; or a 5- or 6-membered heterocyclic ring, each substituted or unsubstituted on ring members with up to 5 substituents independently selected from $R^{17}$;

each $G^2$ is independently phenyl, phenylmethyl (i.e. benzyl), pyridinylmethyl, phenylcarbonyl (i.e. benzoyl), phenoxy, phenylethynyl, phenylsulfonyl or a 5- or 6-membered heterocyclic ring, each substituted or unsubstituted on ring members with up to 5 substituents independently selected from $R^{18}$;

each $R^{16}$, $R^{17}$ and $R^{18}$ is independently halogen, cyano, hydroxy, amino, nitro, —CHO, —C(=O)OH, —C(=O)NH$_2$, —SO$_2$NH$_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_1$-$C_8$ hydroxyalkyl, $C_2$-$C_8$ haloalkylcarbonyl, $C_2$-$C_6$ alkoxyalkyl, $C_2$-$C_6$ alkylaminoalkyl, $C_2$-$C_8$ alkoxycarbonyl, $C_3$-$C_8$ cycloalkyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_3$-$C_8$ dialkylaminoalkyl, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_1$-$C_6$ alkylamino, $C_2$-$C_8$ dialkylamino, $C_2$-$C_8$ alkylcarbonylamino, $C_1$-$C_6$ alkylsulfonylamino, phenyl, pyridinyl or thienyl;

each $R^{19}$ is independently H, cyano, $C_2$-$C_3$ alkylcarbonyl or $C_2$-$C_3$ haloalkylcarbonyl;

each $R^{20}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy, $C_3$-$C_{10}$ trialkylsilyl or $G^1$;

each u and v are independently 0, 1 or 2 (i.e. in each instance of $S(=O)_u(=NR^{14})_v$), provided that the sum of u and v is 0, 1 or 2; and each p and q are independently 0, 1 or 2 (i.e. in each instance of $R^{20}(R^{19}N=)_qS(=O)_p—$), provided that the sum of u and v is 0, 1 or 2 and when p is 0, q is other than 1 or 2.

More particularly, this invention pertains to a compound of Formula 1 (including all stereoisomers), an N-oxide or a salt thereof. This invention also relates to a herbicidal composition comprising a compound of the invention (i.e. in a herbicidally effective amount) and at least one component selected from the group consisting of surfactants, solid diluents and liquid diluents. This invention further relates to a method for controlling the growth of undesired vegetation comprising contacting the vegetation or its environment with a herbicidally effective amount of a compound of the invention (e.g., as a composition described herein).

This invention also includes a herbicidal mixture comprising (a) a compound selected from Formula 1, N-oxides, and salts thereof, and (b) at least one additional active ingredient selected from (b1) through (b16); and salts of compounds of (b1) through (b16), as described below.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "broadleaf" used either alone or in words such as "broadleaf weed" means dicot or dicotyledon, a term used to describe a group of angiosperms characterized by embryos having two cotyledons.

As used herein, the term "alkylating agent" refers to a chemical compound in which a carbon-containing radical is bound through a carbon atom to a leaving group such as halide or sulfonate, which is displaceable by bonding of a nucleophile to said carbon atom. Unless otherwise indicated, the term "alkylating" does not limit the carbon-containing radical to alkyl.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkylene" denotes a straight-chain or branched alkanediyl. Examples of "alkylene" include $CH_2CH_2CH_2$, $CH_2CH(CH_3)$ and the different butylene, pentylene and hexylene isomers.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxyalkyl" denotes at least alkoxy substitution on the alkoxy moiety of alkoxyalkyl moiety. Examples of "alkoxyalkoxyalkyl" include $CH_3OCH_2OCH_2—$, $CH_3CH_2O(CH_3)CHOCH_2—$ and $(CH_3O)_2CHOCH_2—$. "Alkoxyalkoxy" denotes alkoxy substitution on alkoxy. Examples of alkoxyalkoxy include $CH_3CH_2OCH_2O$, $(CH_3)_2CHOCH_2CH_2O$ and $CH_3CH_2CH_2OCH_2O$. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)—$, $CH_3CH_2S(O)—$, $CH_3CH_2CH_2S(O)—$, $(CH_3)_2CHS(O)—$ and the different butylsulfinyl, pentylsulfinyl and hexylsulfinyl isomers. "Alkylsulfonyl" indicates a sulfonyl moiety substituted with a straight-chain or branched alkyl group. Examples of "alkylsulfonyl" include $CH_3S(O)_2—$, $CH_3CH_2S(O)_2—$, $CH_3CH_2CH_2S(O)_2—$, $(CH_3)_2CHS(O)_2—$, and the different butylsulfonyl, pentylsulfonyl and hexylsulfonyl isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Alkylsulfinylalkyl" denotes alkylsulfinyl substitution on alkyl. Examples of "alkylsulfinylalkyl" include $CH_3S(=O)CH_2$, $CH_3S(=O)CH_2CH_2$, $CH_3CH_2S$ (=O)CH$_2$ and CH$_3$CH$_2$S(=O)CH$_2$CH$_2$. "Alkylsulfonylalkyl" denotes alkylsulfonyl substitution on alkyl. Examples of "alkylsulfonylalkyl" include CH$_3$S(=O)$_2$CH$_2$, CH$_3$S(=O)$_2$CH$_2$CH$_2$, CH$_3$CH$_2$S(=O)$_2$CH$_2$ and CH$_3$CH$_2$S(=O)$_2$CH$_2$CH$_2$. Examples of "alkylsulfonyloxy" include CH$_3$S(O)$_2$O—, CH$_3$CH$_2$S(O)$_2$O— and CH$_3$CH$_2$CH$_2$S(O)$_2$O—. "Alkylamino", "dialkylamino", "halodialkylamino" and the like, are defined analogously to the above examples. Examples of "alkylsulfonylamino" include CH$_3$S(=O)NH— and CH$_2$CH$_2$CH$_2$S(=O)NH—. Examples of "alkylaminoalkyl" include CH$_3$NHCH$_2$—, (CH$_3$)$_2$CHNHCH$_2$— and CH$_3$NHCH(CH$_3$)—. Examples of "dialkylaminoalkyl" include (CH$_3$)$_2$NCH$_2$—, (CH$_3$)$_2$NC(CH$_3$)H— and (CH$_3$)(CH$_3$)NCH$_2$—. Examples of "alkylaminocarbonyl" include (CH$_3$)NHC(O)— and (CH$_3$CH$_2$)NHC(O)—. An example of "dialkylaminocarbonyl" is (CH$_3$)$_2$NC(O)—. An example of "alkylaminosulfonyl" is (CH$_3$)NHS(O)$_2$— and an example of "dialkylaminosulfonyl" is (CH$_3$)$_2$NS(O)$_2$—. The term "alkylcarbonylamino" denotes a straight-chain or branched alkyl moiety bonded to the C(=O) moiety of carbonylamino group. Examples of "alkylcarbonylamino" include CH$_3$C(=O)NH— and CH$_3$CH$_2$C(=O)NH—. The term "alkoxycarbonylamino" denotes a straight-chain or branched alkoxy moiety bonded to the C(=O) moiety of carbonylamino group. Examples of "alkoxycarbonylamino" include CH$_3$OC(=O)NH— and CH$_3$CH$_2$OC(=O)NH—.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. Examples of the term "alkylcycloalkylalkyl" include 1-methylcyclopropylmethyl and 2-methylcyclopentylethyl. The term "cycloalkylalkenyl" denotes cycloalkyl bonded to an alkenyl moiety. The term "cycloalkylcycloalkyl" denotes cycloalkyl substitution on a cycloalkyl moiety by a single bond. The term "cycloalkylalkynyl" denotes cycloalkyl bonded to an alkynyl moiety. The term "cycloalkylamino" denotes cycloalkyl bonded to an amino moiety. The term "cycloalkylaminocarbonyl" denotes cycloalkyl bonded to an aminocarbonyl moiety. The term "cycloalkylaminoalkyl" denotes cycloalkyl bonded to an aminoalkyl moiety. The term "cycloalkylcarbonyl" denotes cycloalkyl bonded to a carbonyl moiety. The term "cycloalkylcarbonylalkyl" denotes cycloalkyl bonded to a carbonylalkyl moiety. The term "cycloalkylcarbonyloxy" denotes cycloalkyl bonded to the carbon atom of a carbonyloxy moiety. The term "cycloalkoxy" denotes cycloalkyl linked through an oxygen atom such as cyclopentyloxy and cyclohexyloxy. The term "cycloalkoxyalkyl" denotes cycloalkoxy linked through an alkyl moiety. The terms "cycloalkylthio", "cycloalkylsulfinyl" and "cycloalkylsulfonyl" denotes cycloalkyl bonded through a sulfur, sulfinyl or sulfonyl moiety, respectively.

The term "cycloalkoxycarbonyl" denotes cycloalkoxy linked through a carbonyl moiety. "Cycloalkylalkoxy" denotes cycloalkylalkyl linked through an oxygen atom attached to the alkyl chain. Examples of "cycloalkylalkoxy" include cyclopropylmethoxy, cyclopentylethoxy, and other cycloalkyl moieties bonded to straight-chain or branched alkoxy groups. "Cycloalkenyl" includes groups such as cyclopentenyl and cyclohexenyl as well as groups with more than one double bond such as 1,3- and 1,4-cyclohexadienyl. The term "halocycloalkenyl" denotes halogen substitution on the cycloalkenyl moiety.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include F$_3$C, ClCH$_2$, CF$_3$CH$_2$ and CF$_3$CCl$_2$. The terms "halocycloalkyl", "halocycloalkylalkyl", "halocycloalkoxy", "haloalkoxy", "haloalkoxyalkoxy", "haloalkylthio", "haloalkylsulfinyl", "haloalkylsulfonyl", "haloalkenyl", "haloalkynyl", "haloalkenyloxy", "haloalkenylalkyl", "haloalkylcarbonyl", "haloalkylcarbonylamino", "haloalkylsulfonylamino", "haloalkoxyhaloalkoxy", "haloalkylsulfonyloxy", "haloalkynyloxy", "haloalkoxyalkyl", "haloalkylcarbonyloxy", "haloalkylaminoalkyl" and the like, are defined analogously to the term "haloalkyl". Examples of "haloalkoxy" include CF$_3$O—, CCl$_3$CH$_2$O—, HCF$_2$CH$_2$CH$_2$O— and CF$_3$CH$_2$O—. Examples of "haloalkylthio" include CCl$_3$S—, CF$_3$S—, CCl$_3$CH$_2$S— and C$_1$CH$_2$CH$_2$CH$_2$S—. Examples of "haloalkylsulfinyl" include CF$_3$S(O)—, CCl$_3$S(O)—, CF$_3$CH$_2$S(O)— and CF$_3$CF$_2$S(O)—. Examples of "haloalkylsulfonyl" include CF$_3$S(O)$_2$—, CCl$_3$S(O)$_2$—, CF$_3$CH$_2$S(O)$_2$— and CF$_3$CF$_2$S(O)$_2$—. Examples of "haloalkylsulfonyloxy" include CHCl$_2$S(O)$_2$O—, CH$_2$C$_1$CH$_2$S(O)$_2$O— and CH$_3$CHClCH$_2$S(O)$_2$O—. Examples of "haloalkenyl" include (Cl)$_2$C=CHCH$_2$— and CF$_3$CH$_2$CH=CHCH$_2$—. Examples of "haloalkenyloxy" include (Cl)$_2$C=CHCH$_2$O— and CF$_3$CH$_2$CH=CHCH$_2$O—. Examples of "haloalkynyl" include HC≡CCHCl—, CF$_3$C≡C—, CCl$_3$C≡C— and FCH$_2$C≡CCH$_2$—. Examples of "haloalkynyloxy" include HC≡CCHClO—, CCl$_3$C≡C— and FCH$_2$C≡CCH$_2$O—. Examples of "haloalkoxyalkyl" include CF$_3$OCH$_2$—, C$_1$CH$_2$CH$_2$OCH$_2$CH$_2$—, Cl$_3$CCH$_2$OCH$_2$— as well as branched alkyl derivatives. Examples of "haloalkoxycarbonyl" include CF$_3$OC(O)—, C$_1$CH$_2$CH$_2$OCH$_2$CH$_2$—, Cl$_3$CCH$_2$OCH$_2$OC(O)— as well as branched alkyl derivatives.

"Alkylcarbonyl" denotes a straight-chain or branched alkyl moiety bonded to a C(=O) moiety. "Alkoxycarbonyl" denotes a straight-chain or branched alkoxy moiety bonded to a C(=O) moiety. Examples of "alkylcarbonyl" include CH$_3$C(=O)—, CH$_3$CH$_2$CH$_2$C(=O)— and (CH$_3$)$_2$CHC(=O)—. Examples of "alkoxycarbonyl" include CH$_3$OC(=O)—, CH$_3$CH$_2$OC(=O)—, CH$_3$CH$_2$CH$_2$OC(=O)—, (CH$_3$)$_2$CHOC(=O)— and the different butoxy- or pentoxycarbonyl isomers. "Cycloalkylalkoxycarbonyl" denotes a cycloalkylalkyl moieties bonded to an oxygen atom of alkoxycarbonyl moiety. Examples of "cycloalkylalkoxycarbonyl" include cyclopropyl-CH$_2$OC(=O)—, cyclopropyl-CH(CH$_3$)OC(=O)— and cyclopentyl-CH$_2$OC(=O)—. "Alkylcarbonylalkyl" denotes a straight-chain or branched chain alkyl group bonded to the carbon atom of to a carbonylalkyl moiety. Examples of "alkylcarbonylalkyl" include (CH$_3$)C(=O)CH$_2$— and (CH$_3$CH$_2$)C(=O)CH$_2$—. "Alkylcarbonyloxy" denotes a straight-chain or branched-chain alkyl group bonded to the carbon atom of to a carbonyloxy moiety. Examples of "alkylcarbonyloxy" include (CH$_3$)C(=O)O— and (CH$_3$CH$_2$)C(=O)O—.

The term "cyanoalkyl" or "cyanoalkoxy" means a cyano group bonded through an alkyl or alkoxy moiety, respectively. The carbon in the cyano group is not included in the total number of carbon atoms for this term. The term "nitroalkyl" or "nitroalkenyl" represents a nitro group bonded through an alkyl or alkenyl moiety, respectively. The term "hydroxyalkyl" means a hydroxyl group bonded through an alkyl moiety. The term "trialkylsilyl" means three alkyl groups bonded through silicon. The term "trialkylsilylalkyl" means three alkyl groups bonded through a silylalkyl moiety. The term "trialkylsilylalkoxy" means three alkyl groups bonded through a silylalkoxy moiety.

The total number of carbon atoms in a substituent group is indicated by the "$C_i$-$C_j$" prefix where i and j are numbers from 1 to 12. For example, $C_1$-$C_4$ alkylsulfonyl designates methylsulfonyl through butylsulfonyl; $C_2$ alkoxyalkyl designates $CH_3OCH_2$—; $C_3$ alkoxyalkyl designates, for example, $CH_3CH(OCH_3)$—, $CH_3OCH_2CH_2$— or $CH_3CH_2OCH_2$—; and $C_4$ alkoxyalkyl designates the various isomers of an alkyl group substituted with an alkoxy group containing a total of four carbon atoms, examples including $CH_3CH_2CH_2OCH_2$— and $CH_3CH_2OCH_2CH_2$—.

When a compound is substituted with a substituent bearing a subscript that indicates the number of said substituents can exceed 1, said substituents (when they exceed 1) are independently selected from the group of defined substituents, e.g., $(R^7)_n$, n is 1, 2, 3, 4 or 5). When a group contains a substituent which can be hydrogen, for example $R^2$ or $R^3$, then when this substituent is taken as hydrogen, it is recognized that this is equivalent to said group being unsubstituted. When a variable group is shown to be optionally attached to a position, for example $R^{(7)}_n$ wherein n may be 0, then hydrogen may be at the position even if not recited in the variable group definition. When one or more positions on a group are said to be "not substituted" or "unsubstituted", then hydrogen atoms are attached to take up any free valency.

The expression "fully saturated" in relation to a ring of atoms means that the bonds between the atoms of the ring are all single. The expression "fully unsaturated" in relation to a ring means that the bonds between the atoms in the ring are single or double bonds according to valence bond theory and furthermore the bonds between the atoms in the ring include as many double bonds as possible without double bonds being cumulative (i.e. no C=C=C, N=C=C, etc.). The term "partially unsaturated" in relation to a ring denotes a ring comprising at least one ring member bonded to an adjacent ring member though a double bond and which conceptually potentially accommodates a number of non-cumulated double bonds through adjacent ring members (i.e. in its fully unsaturated counterpart form) greater than the number of double bonds present (i.e. in its partially unsaturated form). When a fully unsaturated ring satisfies Hückel's rule then it can also be described as aromatic.

Unless otherwise indicated, a "ring" or "ring system" as a component of Formula 1 (e.g., substituent $Q^1$) is carbocyclic or heterocyclic. The term "ring system" denotes two or more fused rings. The terms "bicyclic ring system" and "fused bicyclic ring system" denote a ring system consisting of two fused rings, in which either ring can be saturated, partially unsaturated, or fully unsaturated unless otherwise indicated. The term "fused heterobicyclic ring system" denotes a fused bicyclic ring system in which at least one ring atom is not carbon. The term "ring member" refers to an atom or other moiety (e.g., C(=O), C(=S), S(=O) or S(=O)$_2$) forming the backbone of a ring or ring system.

The terms "carbocyclic ring", "carbocycle" or "carbocyclic ring system" denote a ring or ring system wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 5 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring". Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and that (4n+2) π electrons, where n is a positive integer, are associated with the ring to comply with Hückel's rule. The term "aromatic ring or ring system" denotes a carbocyclic or heterocyclic ring or ring system in which the ring or at least one ring of the ring system is aromatic. The term "aromatic ring or ring system" is also referred to as "aryl". The term "aromatic carbocyclic ring system" denotes a carbocyclic ring system in which at least one ring of the ring system is aromatic. The term "aromatic heterocyclic ring system" denotes a heterocyclic ring system in which at least one ring of the ring system is aromatic. The term "nonaromatic ring system" denotes a carbocyclic or heterocyclic ring system that may be fully saturated, as well as partially or fully unsaturated, provided that none of the rings in the ring system are aromatic. The term "nonaromatic carbocyclic ring system" describes a carbocyclic ring system in which no ring in the ring system is aromatic. The term "nonaromatic heterocyclic ring system" denotes a heterocyclic ring system in which no ring in the ring system is aromatic.

The term "substituted or unsubstituted" or "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "substituted or unsubstituted" is used interchangeably with the phrase "optionally substituted" or with the term "(un)substituted." Unless otherwise indicated, an optionally substituted group may have a substituent at each substitutable position of the group, and each substitution is independent of the other.

When $Q^1$ or $Q^2$ is 4- to 7-membered heterocyclic ring system, it may be attached to the remainder of Formula 1 though any available carbon or nitrogen ring atom, unless otherwise described. As noted above, $Q^1$ and $Q^2$ can be (among others) phenyl optionally substituted with one or more substituents selected from a group of substituents as defined in the Summary of the Invention. An example of phenyl optionally substituted with one to five substituents is the ring illustrated as U-1 in Exhibit 1, wherein, for example, $R^v$ is $R^{10}$ as defined in the Summary of the Invention for $Q^1$, or $R^v$ is $R^{11}$ as defined in the Summary of the Invention for $Q^2$, and r is an integer (from 0 to 5).

As noted above, $Q^1$ and $Q^2$ can be (among others) a 5- or 6-membered unsaturated heterocyclic ring, substituted or unsubstituted with one or more substituents selected from a group of substituents as defined in the Summary of the Invention. Examples of a 5- or 6-membered unsaturated aromatic heterocyclic ring substituted or unsubstituted with from one or more substituents include the rings U-2 through U-61 illustrated in Exhibit 1 wherein $R^v$ is any substituent as defined in the Summary of the Invention for $Q^1$ and $Q^2$, and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit 1

U-1

U-2

U-3

U-4

U-5

U-6

U-7

U-8

U-9

U-10

U-11

U-12

U-13

U-14

U-15

U-16

U-17

U-18

U-19

U-20

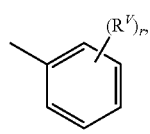
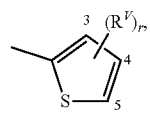
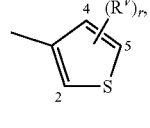
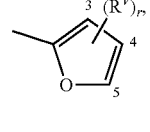
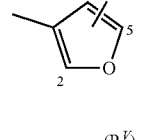
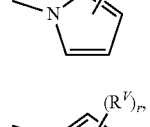
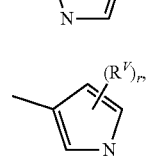
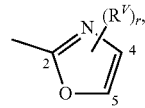
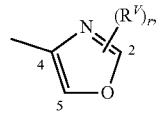
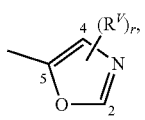
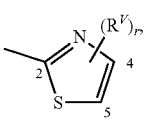
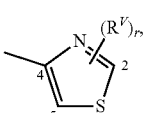
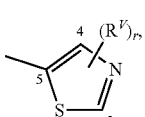
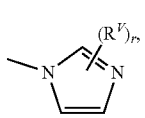
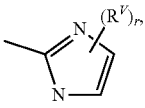
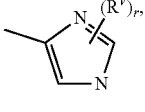
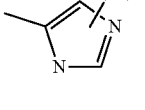
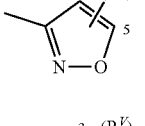
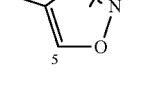

| | |
|---|---|
| 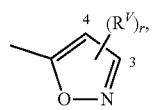 | U-21 |
| 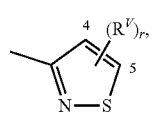 | U-22 |
| 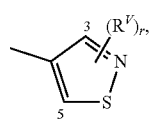 | U-23 |
| 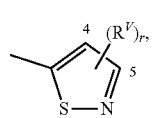 | U-24 |
| 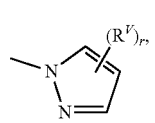 | U-25 |
| 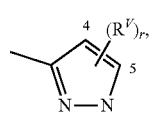 | U-26 |
| 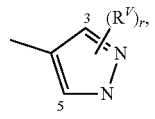 | U-27 |
| 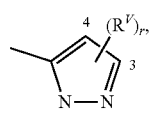 | U-28 |
| 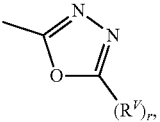 | U-29 |
| 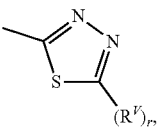 | U-30 |
| 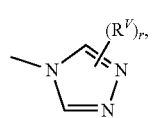 | U-31 |
| 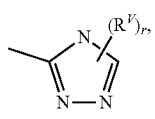 | U-32 |
| | |
|---|---|
| 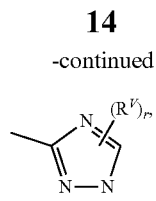 | U-33 |
| 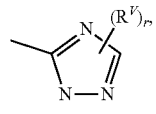 | U-34 |
| 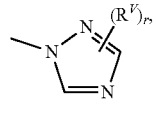 | U-35 |
| 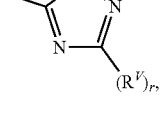 | U-36 |
| 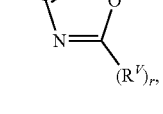 | U-37 |
| 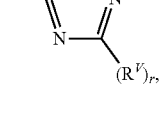 | U-38 |
| 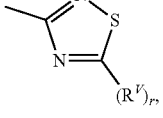 | U-39 |
| 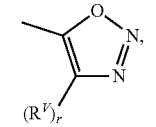 | U-40 |
| 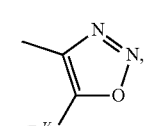 | U-41 |
| 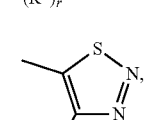 | U-42 |
| 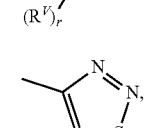 | U-43 |
| 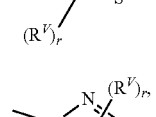 | U-44 |
| 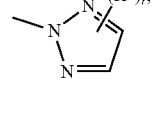 | |

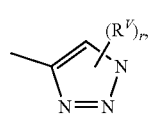 U-45

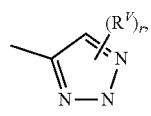 U-46

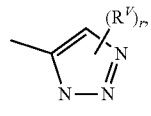 U-47

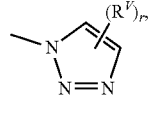 U-48

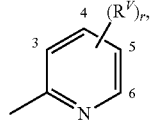 U-49

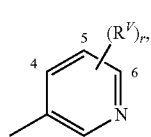 U-50

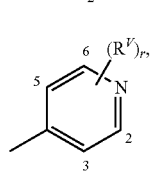 U-51

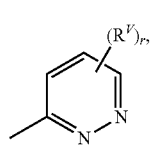 U-52

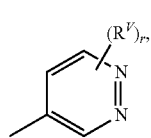 U-53

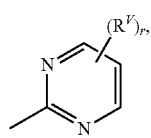 U-54

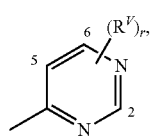 U-55

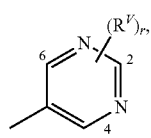 U-56

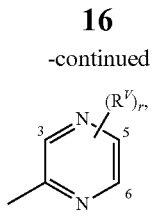 U-57

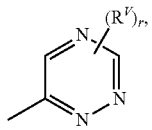 U-58

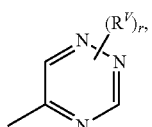 U-59

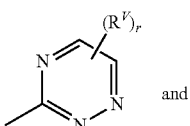 U-60 and

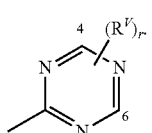 U-61

Note that when $Q^1$ or $Q^2$ is a 5- or 6-membered saturated or unsaturated non-aromatic heterocyclic ring optionally substituted with one or more substituents selected from the group of substituents as defined in the Summary of the Invention for $Q^1$ or $Q^2$, one or two carbon ring members of the heterocycle can optionally be in the oxidized form of a carbonyl moiety.

Examples of a 5- or 6-membered saturated or non-aromatic unsaturated heterocyclic ring containing ring members selected from up to two O atoms and up to two S atoms, and optionally substituted on carbon atom ring members with up to five substituents as defined in the Summary of the Invention includes the rings G-1 through G-35 as illustrated in Exhibit 2. Note that when the attachment point on the G group is illustrated as floating, the G group can be attached to the remainder of Formula 1 through any available carbon or nitrogen of the G group by replacement of a hydrogen atom. The optional substituents corresponding to $R^V$ can be attached to any available carbon or nitrogen by replacing a hydrogen atom. For these G rings, r is typically an integer from 0 to 4, limited by the number of available positions on each G group.

Note that when $Q^1$ or $Q^2$ comprises a ring selected from G-28 through G-35, $G^2$ is selected from O, S or N. Note that when $G^2$ is N, the nitrogen atom can complete its valence by substitution with either H or the substituents corresponding to $R^V$ as defined in the Summary of the Invention for $Q^1$ or $Q^2$ (i.e. $R^{10}$ or $R^{11}$ on carbon atoms and $R^{12}$ or $R^{13}$ on nitrogen atoms).

Exhibit 2

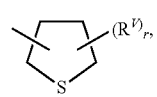 G-1

-continued
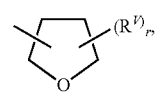 G-2
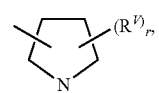 G-3
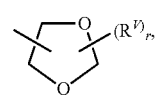 G-4
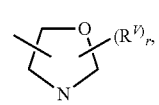 G-5
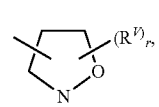 G-6
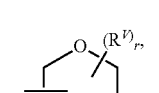 G-7
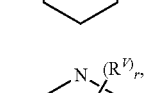 G-8
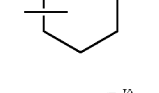 G-9
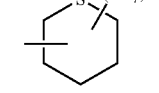 G-10
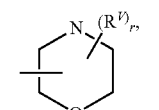 G-11
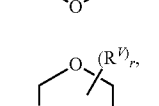 G-12
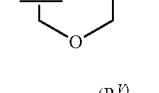 G-13
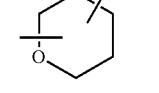 G-14
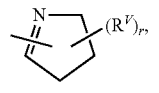 G-15
-continued
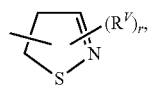 G-16
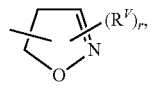 G-17
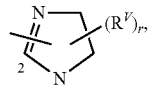 G-18
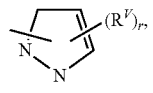 G-19
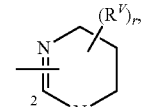 G-20
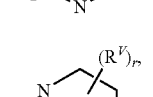 G-21
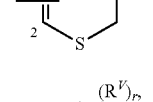 G-22
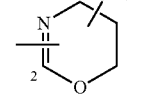 G-23
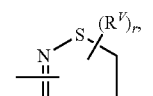 G-24
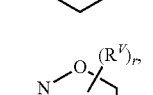 G-25
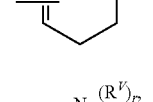 G-26
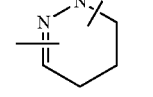 G-27
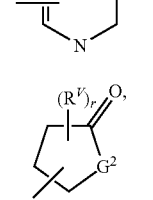 G-28

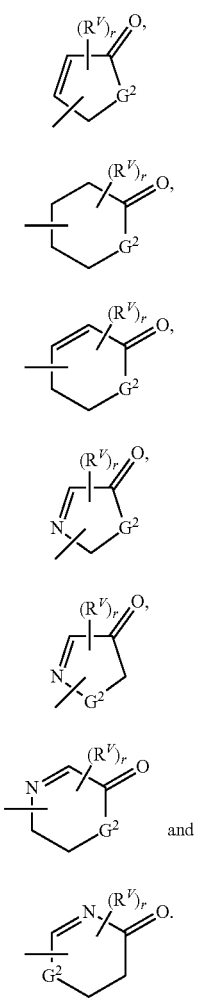

As noted above, $Q^1$ or $Q^2$ can be (among others) an 8-, 9- or 10-membered fused bicyclic ring system optionally substituted with one or more substituents selected from a group of substituents as defined in the Summary of the Invention (i.e. $R^{10}$ or $R^{11}$ on carbon atoms and $R^{12}$ or $R^{13}$ on nitrogen atoms). Examples of 8-, 9- or 10-membered fused bicyclic ring system optionally substituted with from one or more substituents include the rings U-81 through U-123 illustrated in Exhibit 3 wherein $R^V$ is any substituent as defined in the Summary of the Invention for $Q^1$ or $Q^2$ (i.e. $R^{10}$ or $R^{11}$ on carbon atoms and $R^{12}$ or $R^{13}$ on nitrogen atoms), and r is typically an integer from 0 to 5.

Exhibit 3

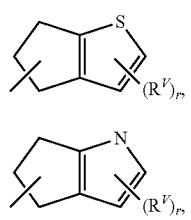

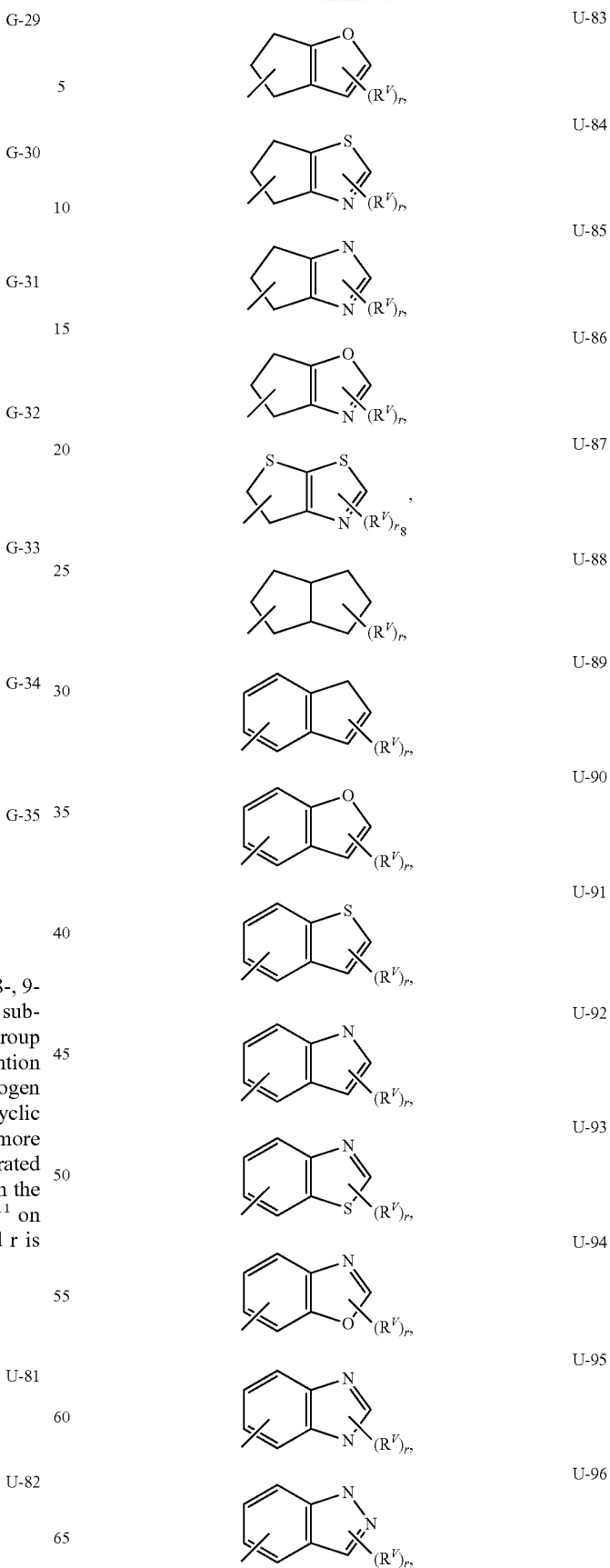

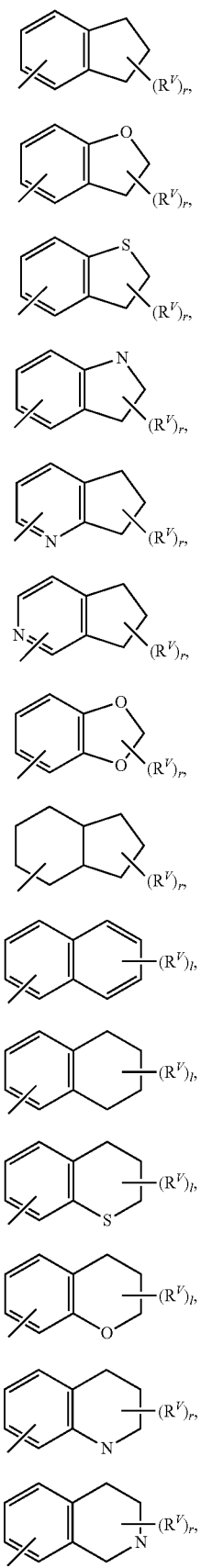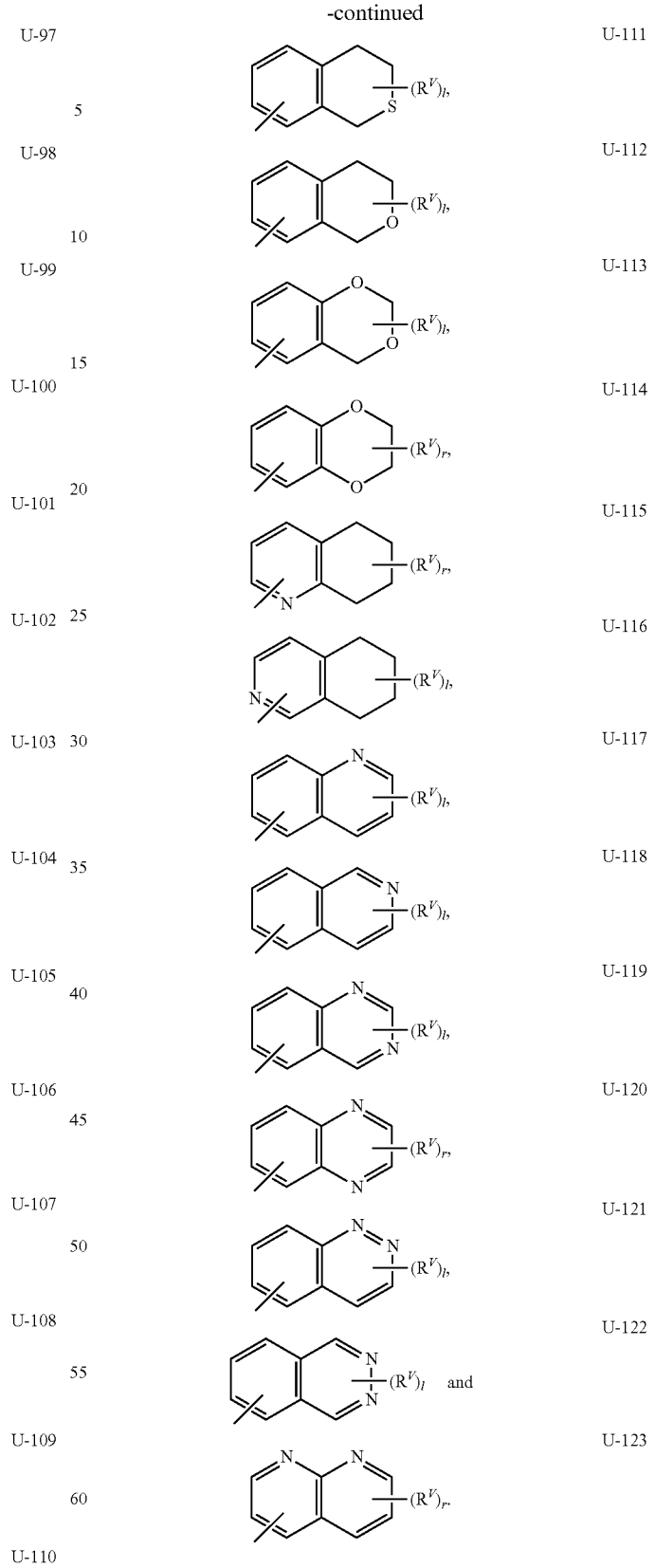
Although $R^v$ groups are shown in the structures U-1 through U-123, it is noted that they do not need to be present since they are optional substituents. Note that when $R^v$ is H when attached to an atom, this is the same as if said atom is unsubstituted. The nitrogen atoms that require substitution to fill their valence are substituted with H or R$^v$. Note that when the attachment point between (R$^v$)$_r$ and the U group is illustrated as floating, (R$^v$)$_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. Note that some U groups can only be substituted with less than 4 R$^v$ groups (e.g., U-2 through U-5, U-7 through U-48, and U-52 through U-61).

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form. Particularly when R$^4$ and R$^5$ are each H, the C(O)N(Q$^2$)(R$^9$) and Q$^1$ substituents are typically mostly in the thermodynamically preferred trans configuration on the pyrrolidinone ring.

For example, as shown in the following, the C(O)N(Q$^2$)(R$^9$) moiety (i.e. a compound of Formula 1 wherein both Y is O; and J is —CR$^2$R$^3$—, R$^1$ is H, and R$^2$ and R$^3$ are both H) bonded to the carbon at the 3-position of the ring and Q$^1$ bonded to the carbon at the 4-position of the ring are generally found in the trans configuration. These two carbon atoms both possess a chiral center. The most prevalent pair of enantiomers are depicted as Formula 1' and Formula 1". While this invention pertains to all stereoisomers, the preferred enantiomer for biological operability is identified as Formula 1'. For a comprehensive discussion of all aspects of stereoisomerism, see Ernest L. Eliel and Samuel H. Wilen, *Stereochemistry of Organic Compounds*, John Wiley & Sons, 1994.

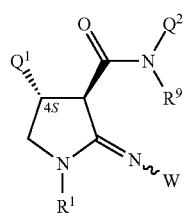

1'

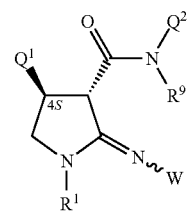

1"

The skilled artisan will also recognize that the carbon atom at the 5-position of the pyrrolidinone ring (i.e. when J is —CR$^2$R$^3$—, the carbon atom to which both R$^2$ and R$^3$ are bonded) also contains a stereocenter indicated by a (*) as shown in Formula 1'". This invention pertains to all stereoisomers, and therefore, when either R$^2$ or R$^3$ are other than the same substituent, then a mixture of diastereomers is possible.

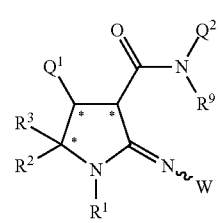

1'"

Molecular depictions drawn herein follow standard conventions for depicting stereochemistry. To indicate stereoconfiguration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom closer to the viewer. Constant width lines indicate bonds with a direction opposite or neutral relative to bonds shown with solid or dashed wedges; constant width lines also depict bonds in molecules or parts of molecules in which no particular stereoconfiguration is intended to be specified.

This invention also comprises racemic mixtures, for example, equal amounts of the enantiomers of Formulae 1' and 1" (and optionally 1'"). In addition, this invention includes compounds that are enriched compared to the racemic mixture in an enantiomer of Formula 1. Also included are the essentially pure enantiomers of compounds of Formula 1, for example, Formula 1' and Formula 1".

When enantiomerically enriched, one enantiomer is present in greater amounts than the other, and the extent of enrichment can be defined by an expression of enantiomeric excess ("ee"), which is defined as (2x−1)·100%, where x is the mole fraction of the dominant enantiomer in the mixture (e.g., an ee of 20% corresponds to a 60:40 ratio of enantiomers).

Preferably the compositions of this invention have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Compounds of Formula 1 can comprise additional chiral centers. For example, substituents and other molecular constituents such as $R^A$ and $R^B$ may themselves contain chiral centers. This invention comprises racemic mixtures as well as enriched and essentially pure stereoconfigurations at these additional chiral centers.

Compounds of this invention can exist as one or more conformational isomers due to restricted rotation about the amide bond (e.g., $C(O)N(Q^2)(R^9)$) in Formula 1. This invention comprises mixtures of conformational isomers. In addition, this invention includes compounds that are enriched in one conformer relative to others.

When enantiomerically enriched, one enantiomer is present in greater amounts than the other, and the extent of enrichment can be defined by an expression of enentiomeric ratio (ER) expressed as the relative area % of the two entantiomers determined by chiral high-performance liquid chromatography.

Preferably the compositions of this invention have at least a 50% ER; more preferably at least a 75% ER; still more preferably at least a 90% ER; and the most preferably at least a 94% ER of the more active isomer. Of particular note are enantiomerically pure embodiments of the more active isomer.

Compounds of Formula 1 can comprise additional chiral centers. For example, substituents and other molecular constituents such as $R^2$, $R^3$ and $R^6$ may themselves contain chiral centers. This invention comprises racemic mixtures as well as enriched and essentially pure stereoconfigurations at these additional chiral centers.

Compounds of Formula 1 typically exist in more than one form, and Formula 1 thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, stereoisomers, N-oxides and agriculturally suitable salts thereof.

Embodiments of the present invention as described in the Summary of the Invention include where Formula 1 as used in the following Embodiments includes N-oxides and salts thereof:

Embodiment 1

A compound of Formula 1, including all stereoisomers, N-oxides, and salts thereof, agricultural compositions containing them and their use as herbicides as described in the Summary of the Invention.

Embodiment 2

A compound of Embodiment 1 wherein W is —NR$^A$R$^B$.

Embodiment 3

A compound of Embodiment 1 wherein W is —OR$^C$.

Embodiment 4

A compound of Embodiment 1 or 2 wherein R$^A$ is H, cyano, CHO, $C_2$-$C_4$ alkylcarbonyl or $C_1$-$C_4$ alkyl.

Embodiment 5

A compound of Embodiment 4 wherein $R^A$ is H, CHO, $C_2$-$C_4$ alkylcarbonyl or $C_1$-$C_4$ alkyl.

Embodiment 6

A compound of Embodiment 5 wherein $R^A$ is H or $C_1$-$C_4$ alkyl.

Embodiment 7

A compound of Embodiment 6 wherein $R^A$ is H or $CH_3$.

Embodiment 8

A compound of Embodiment 7 wherein $R^A$ is H.

Embodiment 9

A compound of Embodiment 7 wherein $R^A$ is $CH_3$.

Embodiment 10

A compound of any one of Embodiments 1 through 9 wherein $R^B$ is H, CHO, $C_1$-$C_6$ alkyl, $C_2$-$C_6$ alkenyl, $C_3$-$C_6$ alkynyl, $C_2$-$C_8$ alkoxyalkyl, $C_2$-$C_8$ alkylthioalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl or $C_2$-$C_8$ dialkylaminosulfonyl; or a phenyl ring substituted or unsubstituted with up to 5 substituents independently selected from $R^{16}$; or a 5- to 6-membered heterocyclic ring, substituted or unsubstituted on ring members with up to 5 substituents independently selected from $R^{16}$; or $R^A$ and $R^B$ are taken together along with the nitrogen atom to which they are both bonded to form a 5- or 6-membered ring containing ring members selected from carbon, oxygen, nitrogen and —C(=O)—; or taken together as an 6- to 10-membered bicyclic ring system.

Embodiment 11

A compound of Embodiment 10 wherein $R^B$ is H, $C_1$-$C_6$ alkyl, $C_2$-$C_8$ alkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl or $C_2$-$C_8$ dialkylaminosulfonyl; or a phenyl ring substituted or unsubstituted with up to 4 substituents independently selected from $R^{16}$; or $R^A$ and $R^B$ are taken together along with the nitrogen atom to which they are both bonded to form a 5- or 6-membered ring containing ring members selected from carbon, oxygen and —C(=O)—; or taken together as a 6- to 10-membered bicyclic ring system.

Embodiment 12

A compound of Embodiment 11 wherein $R^B$ is H, $C_1$-$C_6$ alkyl, $C_2$-$C_8$ alkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl or $C_2$-$C_8$ dialkylaminosulfonyl; or a phenyl ring substituted or unsubstituted with up to 3 substituents independently selected from $R^{16}$;

$R^A$ and $R^B$ are taken together along with the nitrogen atom to which they are both bonded to form a 5-membered ring containing ring members selected from carbon and oxygen; or taken together as a 6- to 9-membered bicyclic ring system.

Embodiment 13

A compound of Embodiment 12 wherein $R^B$ is H, $C_2$-$C_8$ alkylcarbonyl, $C_4$-$C_{10}$ cycloalkylcarbonyl, $C_2$-$C_8$ alkoxycarbonyl or $C_4$-$C_{10}$ cycloalkoxycarbonyl; or a phenyl ring substituted or unsubstituted with up to 3 substituents independently selected from $R^{16}$.

Embodiment 14

A compound of Embodiment 13 wherein $R^B$ is H or $C_2$-$C_8$ alkylcarbonyl.

Embodiment 15

A compound of Embodiment 1 or 2 wherein $R^A$ and $R^B$ are taken together along with the nitrogen atom to which they are both bonded to form a 5- or 6-membered ring containing ring members selected from carbon and oxygen and —C(=O)—; or taken together as a 6- to 10-membered bicyclic ring systems selected from the group consisting of

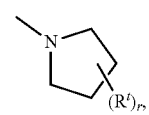

W-1

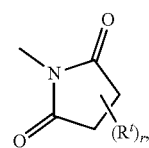

W-2

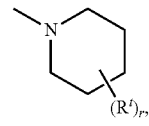

W-3

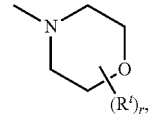

W-4

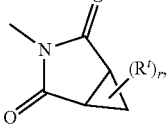

W-5

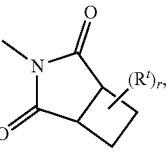

W-6

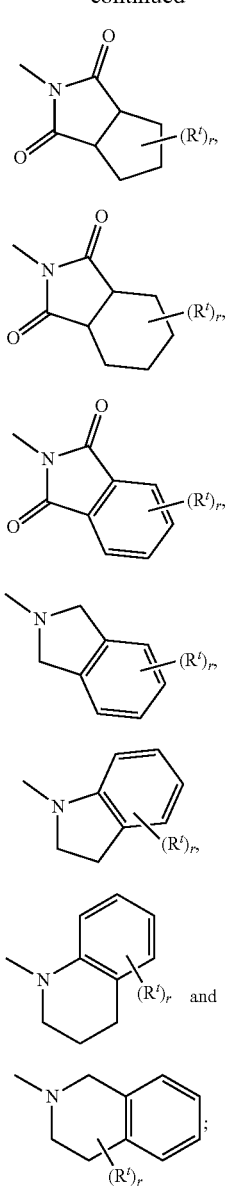

$R^t$ is halogen, cyano or $C_1$-$C_4$ alkyl; and r is 0 to 4.

Embodiment 16

A compound of Embodiment 15 wherein $R^A$ and $R^B$ are taken together as an 8- to 9-membered bicyclic ring system selected from W-7, W-8 and W-9; $R^t$ is halogen or $C_1$-$C_4$ alkyl; and r is 0 to 3.

Embodiment 17

A compound of Embodiment 15 wherein $R^A$ and $R^B$ are taken together as a 9-membered bicyclic ring system selected from W-9; $R^t$ is F, Cl, Br or $CH_3$; and r is 0 to 2.

Embodiment 18

A compound of any one of Embodiments 1 or 3 wherein $R^C$ is $C_1$-$C_4$ haloalkyl, $C_2$-$C_4$ haloalkylcarbonyl or $C_3$-$C_6$ cycloalkyl; or phenyl substituted or unsubstituted with halogen or $C_1$-$C_4$ alkyl; or a 6-membered nitrogen containing aromatic ring substituted or unsubstituted with halogen or $C_1$-$C_4$ alkyl.

Embodiment 19

A compound of Embodiment 18 wherein $R^C$ is $CF_3$, —C(=O)$CF_3$ or cyclopropyl; or phenyl substituted or unsubstituted with halogen or $C_1$-$C_4$ alkyl; or an unsubstituted pyridine or pyrimidine ring.

Embodiment 20

A compound of Embodiment 19 wherein $R^C$ is $CF_3$; or phenyl substituted or unsubstituted with halogen; or an unsubstituted pyridine ring.

Embodiment 21

A compound of any one of Embodiments 1 through 20 wherein J is —$CR^2R^3$—, —$CR^2R^3$—$CR^4R^5$— or —$NR^6$—.

Embodiment 22

A compound of Embodiment 21 wherein J is —$CR^2R^3$— or —$CR^2R^3$—$CR^4R^5$—.

Embodiment 23

A compound of Embodiment 22 wherein J is —$CR^2R^3$—$CR^4R^5$—.

Embodiment 24

A compound of Embodiment 22 wherein J is —$CR^2R^3$—.

Embodiment 25

A compound of any one of Embodiments 1 through 24 wherein Y is O or S.

Embodiment 26

A compound of Embodiment 25 wherein Y is S.

Embodiment 27

A compound of Embodiment 25 wherein Y is O.

Embodiment 28

A compound of any one of Embodiments 1 through 27 wherein $R^1$ is H, CHO, $C_3$-$C_8$ alkylcarbonylalkyl, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ alkylthioalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_2$-$C_8$ alkylaminocarbonyl, $C_3$-$C_{10}$ dialkylaminocarbonyl or $C_4$-$C_{10}$ cycloalkylaminocarbonyl.

Embodiment 29

A compound of Embodiment 28 wherein $R^1$ is H, $C_3$-$C_8$ alkylcarbonylalkyl, $C_1$-$C_6$ alkyl, $C_1$-$C_6$ haloalkyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_2$-$C_8$ haloalkoxyalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl or $C_2$-$C_8$ haloalkoxycarbonyl.

Embodiment 30

A compound of Embodiment 29 wherein $R^1$ is H, $C_1$-$C_6$ alkyl, $C_1$-$C_6$ haloalkyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_2$-$C_8$ haloalkoxyalkyl or $C_2$-$C_8$ alkoxycarbonyl.

Embodiment 31

A compound of Embodiment 30 wherein $R^1$ is H, $C_1$-$C_6$ alkyl, $C_3$-$C_6$ cycloalkyl, $C_4$-$C_8$ cycloalkylalkyl or $C_2$-$C_8$ alkoxyalkyl.

Embodiment 32

A compound of Embodiment 31 wherein $R^1$ is H, $CH_3$, $CH_2CH_3$, cyclopropyl, cyclopropylmethyl or $CH_2OCH_3$.

Embodiment 33

A compound of any one of Embodiments 1 through 32 wherein $Q^1$ is a phenyl ring or a naphthalenyl ring system, each ring or ring system substituted or unsubstituted with up to 5 substituents independently selected from $R^{10}$; or a 5- to 6-membered heterocyclic ring; or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 2 carbon ring members are independently selected from C(=O) and C(=S), and the sulfur atom ring members are independently selected from $S(=O)_u(=NR^{14})_v$, each ring or ring system substituted or unsubstituted with up to 4 substituents independently selected from $R^{10}$ on carbon atom ring members and selected from $R^{12}$ on nitrogen atom ring members.

Embodiment 34

A compound of Embodiment 33 wherein $Q^1$ is a phenyl ring substituted or unsubstituted with up to 4 substituents independently selected from $R^{10}$; or a 5- to 6-membered heterocyclic ring, each ring containing ring members selected from carbon atoms and 1 to 4 heteroatoms independently selected from up to 2 O, up to 2 S and up to 4 N atoms, each ring substituted or unsubstituted with up to 4 substituents independently selected from $R^{10}$ on carbon atom ring members and selected from $R^{12}$ on nitrogen atom ring members.

Embodiment 35

A compound of Embodiment 34 wherein $Q^1$ is a phenyl ring substituted or unsubstituted with up to 4 substituents independently selected from $R^{10}$.

Embodiment 36

A compound of Embodiment 35 wherein $Q^1$ is a phenyl ring substituted or unsubstituted with up to 3 substituents independently selected from $R^{10}$.

Embodiment 37

A compound of Embodiment 36 wherein $Q^1$ is a phenyl ring substituted or unsubstituted with up to 2 substituents independently selected from $R^{10}$.

Embodiment 38

A compound of Embodiment 37 wherein $Q^1$ is a phenyl ring substituted with up 2 substituents independently selected from $R^{10}$.

Embodiment 39

A compound of Embodiment 38 wherein $Q^1$ is a phenyl ring substituted with up 2 substituents independently selected from $R^{10}$ where one substituent is at the para (4-) position.

Embodiment 40

A compound of Embodiment 38 wherein $Q^1$ is a phenyl ring substituted with up 2 substituents independently selected from $R^{10}$ where one substituent is at the meta (3-) position.

Embodiment 41

A compound of any one of Embodiments 1 through 40 wherein $Q^1$ is other than an unsubstituted phenyl ring.

Embodiment 42

A compound of Embodiment 33 wherein $Q^1$ is an 8- to 10-membered bicyclic ring system containing ring members selected from carbon atoms and 1 to 4 heteroatoms independently selected from up to 2 O atoms, each bicyclic ring system substituted or unsubstituted with up to 4 substituents independently selected from $R^{10}$ on carbon atom ring members.

Embodiment 43

A compound of Embodiment 42 wherein $Q^1$ is a 9-membered bicyclic ring system containing ring members selected from carbon atoms and 1 to 4 heteroatoms independently selected from up to 2 O atoms, each bicyclic ring system substituted or unsubstituted with up to 4 substituents independently selected from $R^{10}$ on carbon atom ring members.

Embodiment 44

A compound of Embodiment 43 wherein $Q^1$ is a 9-membered heteroaromatic bicyclic ring system containing ring members selected from carbon atoms and 2 O atoms, each bicyclic ring system substituted or unsubstituted with up to 3 substituents independently selected from $R^{10}$ on carbon atom ring members (i.e. U-103 in Exhibit 3).

Embodiment 45

A compound of Embodiment 44 wherein $Q^1$ is U-103A:

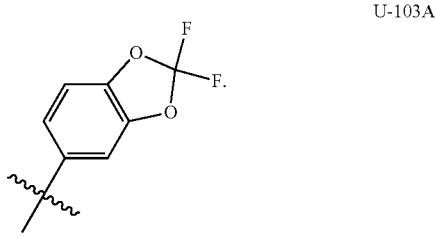 [SMILES: *c1ccc2c(c1)OC(F)(F)O2]

U-103A

Embodiment 46

A compound of any one of Embodiments 1 through 45 wherein $Q^2$ is a phenyl ring, each ring substituted or unsubstituted with up to 4 substituents independently selected from $R^{11}$; or a 5- to 6-membered heterocyclic ring; or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 2 carbon ring members are independently selected from C(=O) and C(=S), and the sulfur atom ring members are independently selected from $S(=O)_u(=NR^{14})_v$, each ring or ring system substituted or unsubstituted with up to 4 substituents independently selected from $R^{11}$ on carbon atom ring members and selected from $R^{13}$ on nitrogen atom ring members.

Embodiment 47

A compound of Embodiment 46 wherein $Q^2$ is a phenyl ring, substituted or unsubstituted with up to 4 substituents independently selected from $R^{11}$; or a 5- to 6-membered heterocyclic ring; or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 2 carbon ring members are independently selected from C(=O) and C(=S), and the sulfur atom ring members are independently selected from $S(=O)_u(=NR^{14})_v$, each ring or ring system substituted or unsubstituted with up to 4 substituents independently selected from $R^{11}$ on carbon atom ring members and selected from $R^{13}$ on nitrogen atom ring members.

Embodiment 48

A compound of Embodiment 47 wherein $Q^2$ is a phenyl ring, substituted or unsubstituted with up to 4 substituents independently selected from $R^{11}$; or a 5- to 6-membered heterocyclic ring containing ring members selected from carbon atoms and 1 to 4 heteroatoms independently selected from up to 4 N atoms, wherein up to 2 carbon ring members are independently selected from C(=O) and C(=S), each ring or ring system substituted or unsubstituted with up to 4 substituents independently selected from $R^{11}$ on carbon atom ring members and selected from $R^{13}$ on nitrogen atom ring members.

Embodiment 49

A compound of Embodiment 48 wherein $Q^2$ is a phenyl ring, substituted or unsubstituted with up to 4 substituents independently selected from $R^{11}$.

Embodiment 50

A compound of Embodiment 49 wherein $Q^2$ is a phenyl ring, substituted or unsubstituted with up to 3 substituents independently selected from $R^{11}$.

Embodiment 51

A compound of Embodiment 50 wherein $Q^2$ is a phenyl ring, substituted or unsubstituted with up to 2 substituents independently selected from $R^{11}$.

Embodiment 52

A compound of Embodiment 51 wherein $Q^2$ is a phenyl ring, substituted with at least 2 substituents independently selected from $R^{11}$ where one substituent is at the ortho (2-) position.

Embodiment 53

A compound of Embodiment 52 wherein $Q^2$ is a phenyl ring, substituted with at least 2 substituents independently selected from $R^{11}$ where one substituent is at the meta (3-) position.

Embodiment 54

A compound of any one of Embodiments 1 through 53 wherein $Q^2$ is other than an unsubstituted phenyl ring.

Embodiment 55

A compound of any one of Embodiments 1 through 54 wherein $R^2$ and $R^3$ are each independently H or $C_1$-$C_4$ alkyl.

Embodiment 56

A compound of Embodiment 55 wherein $R^2$ and $R^3$ are each independently H or $CH_3$.

Embodiment 57

A compound of Embodiment 56 wherein $R^2$ and $R^3$ are each independently H.

Embodiment 58

A compound of any one of Embodiments 1 through 57 wherein $R^4$ and $R^5$ are each independently H, halogen, $C_1$-$C_4$ alkyl or $C_1$-$C_4$ alkoxy.

Embodiment 59

A compound of Embodiment 58 wherein $R^4$ and $R^5$ are each independently H, halogen or $C_1$-$C_4$ alkyl.

Embodiment 60

A compound of Embodiment 59 wherein $R^4$ and $R^5$ are each independently H, Cl or $CH_3$.

Embodiment 61

A compound of any one of Embodiments 1 through 60 wherein $R^6$ is H, $C_1$-$C_6$ alkyl or $C_1$-$C_6$ alkoxy.

Embodiment 62

A compound of Embodiment 61 wherein $R^6$ is H or $C_1$-$C_6$ alkyl.

Embodiment 63

A compound of Embodiment 62 wherein $R^6$ is H or $CH_3$.

Embodiment 64

A compound of Embodiment 63 wherein $R^6$ is H.

Embodiment 65

A compound of any one of Embodiments 1 through 27 or 33 through 60 wherein $R^1$ and $R^6$ are taken together as $C_3$ alkylene or —$CH_2OCH_2$—.

Embodiment 66

A compound of Embodiment 65 wherein $R^1$ and $R^6$ are taken together as $C_3$ alkylene.

Embodiment 67

A compound of any one of Embodiments 1 through 66 wherein $R^7$ and $R^8$ are each independently H, halogen, $C_1$-$C_4$ alkoxy or $C_1$-$C_4$ alkyl.

Embodiment 68

A compound of Embodiment 67 wherein $R^7$ and $R^8$ are each independently H, F, $C_1$ or $CH_3$.

Embodiment 69

A compound of Embodiment 68 wherein $R^7$ and $R^8$ are each independently H or $CH_3$.

Embodiment 70

A compound of Embodiment 69 wherein $R^7$ and $R^8$ are each independently H.

Embodiment 71

A compound of any one of Embodiments 1 through 70 wherein $R^9$ is H, $C_1$-$C_6$ alkyl, $C_2$-$C_8$ alkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_4$-$C_{10}$ cycloalkylcarbonyl, $C_2$-$C_8$ alkoxycarbonyl or $C_4$-$C_{10}$ cycloalkoxycarbonyl.

Embodiment 72

A compound of Embodiment 71 wherein $R^9$ is H, $C_1$-$C_6$ alkyl, $C_2$-$C_8$ alkoxyalkyl, $C_2$-$C_8$ alkylcarbonyl or $C_2$-$C_8$ alkoxycarbonyl.

Embodiment 73

A compound of Embodiment 72 wherein $R^9$ is H, $C_1$-$C_6$ alkyl or $C_2$-$C_8$ alkoxycarbonyl.

Embodiment 74

A compound of Embodiment 73 wherein $R^9$ is H, $CH_3$ or —$C(=O)OCH_3$.

Embodiment 75

A compound of Embodiment 74 wherein $R^9$ is H.

Embodiment 76

A compound of any one of Embodiments 1 through 75 wherein each $R^{10}$ and $R^{11}$ is halogen, nitro, $C_1$-$C_8$ alkyl, $C_1$-$C_8$ cyanoalkyl, $C_1$-$C_8$ cyanoalkoxy, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkoxyhaloalkoxy, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_2$-$C_8$ alkylcarbonyl, $C_2$-$C_8$ haloalkylcarbonyl, $C_4$-$C_{10}$ cycloalkylcarbonyl, —$C(=O)OH$, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —$C(=O)NH_2$, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_8$ haloalkenyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylsulfonyl, $C_1$-$C_8$ haloalkylsulfonyl, $C_3$-$C_8$ cycloalkylsulfonyl.

Embodiment 77

A compound of Embodiment 76 wherein each $R^{10}$ and $R^{11}$ is independently halogen, $C_1$-$C_8$ alkyl, $C_1$-$C_8$ haloalkyl, $C_2$-$C_8$ alkoxyalkyl, $C_3$-$C_8$ alkoxyalkoxyalkyl, $C_4$-$C_{10}$ cycloalkylalkyl, $C_5$-$C_{12}$ alkylcycloalkylalkyl, $C_3$-$C_8$ cycloalkyl, $C_3$-$C_8$ halocycloalkyl, $C_6$-$C_{12}$ cycloalkylcycloalkyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_1$-$C_8$ alkoxy, $C_1$-$C_8$ haloalkoxy, $C_2$-$C_8$ haloalkenyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy or $C_2$-$C_8$ haloalkylcarbonyloxy.

Embodiment 78

A compound of Embodiment 77 wherein each $R^{10}$ and $R^{11}$ is independently halogen, $C_1$-$C_8$ alkyl, $C_1$-$C_8$ haloalkyl, $C_2$-$C_8$ alkoxyalkyl, $C_4$-$C_{10}$ cycloalkylalkyl, $C_5$-$C_{12}$ alkylcycloalkylalkyl, $C_3$-$C_8$ cycloalkyl, $C_3$-$C_8$ halocycloalkyl, $C_2$-$C_8$ haloalkoxyalkyl, $C_1$-$C_8$ alkoxy, $C_1$-$C_8$ haloalkoxy or $C_2$-$C_8$ alkoxyalkoxy.

Embodiment 79

A compound of Embodiment 78 wherein each $R^{10}$ and $R^{11}$ is independently halogen, $C_1$-$C_8$ alkyl, $C_1$-$C_8$ haloalkyl, $C_3$-$C_8$ cycloalkyl, $C_1$-$C_8$ alkoxy or $C_1$-$C_8$ haloalkoxy.

Embodiment 80

A compound of Embodiment 79 wherein each $R^{10}$ and $R^{11}$ is independently halogen, $C_1$-$C_8$ alkyl, $C_1$-$C_8$ haloalkyl, $C_1$-$C_8$ alkoxy or $C_1$-$C_8$ haloalkoxy.

Embodiment 81

A compound of Embodiment 80 wherein each $R^{10}$ and $R^{11}$ is independently halogen or $C_1$-$C_8$ alkyl.

Embodiment 82

A compound of Embodiment 81 wherein each $R^{10}$ and $R^{11}$ is independently halogen or $C_1$-$C_8$ haloalkyl.

Embodiment 83

A compound of Embodiment 80 wherein each $R^{10}$ and $R^{11}$ is independently halogen or $C_1$-$C_8$ alkoxy.

Embodiment 84

A compound of Embodiment 80 wherein each $R^{10}$ and $R^{11}$ is independently halogen or $C_1$-$C_8$ haloalkoxy.

Embodiment 85

A compound of Embodiment 80 wherein each $R^{10}$ and $R^{11}$ is independently $C_1$-$C_8$ alkyl or $C_1$-$C_8$ alkoxy.

Embodiment 86

A compound of Embodiment 80 wherein each $R^{10}$ and $R^{11}$ is independently $C_1$-$C_8$ alkyl or $C_1$-$C_8$ haloalkyl.

Embodiment 87

A compound of any one of Embodiments 1 through 86 wherein each $R^{12}$ and $R^{13}$ is independently $C_1$-$C_3$ alkyl, $C_2$-$C_3$ alkenyl, $C_3$-$C_6$ cycloalkyl, $C_2$-$C_3$ alkoxyalkyl, $C_2$-$C_3$ alkylcarbonyl or $C_2$-$C_3$ alkylaminoalkyl.

Embodiment 88

A compound of Embodiment 87 wherein each $R^{12}$ and $R^{13}$ is independently $C_1$-$C_3$ alkyl, $C_3$-$C_6$ cycloalkyl or $C_2$-$C_3$ alkylcarbonyl.

Embodiment 89

A compound of Embodiment 88 wherein each $R^{12}$ and $R^{13}$ is independently $C_1$-$C_3$ alkyl or $C_2$-$C_3$ alkylcarbonyl.

Embodiment 90

A compound of Embodiment 89 wherein each $R^{12}$ and $R^{13}$ is independently $C_1$-$C_3$ alkyl.

Embodiment 91

A compound of Embodiment 90 wherein each $R^{12}$ and $R^{13}$ is independently $CH_3$.

Embodiment 92

A compound of any one of Embodiments 1 through 91 wherein each $R^{14}$ is independently H or —(C=O)$CH_3$.

Embodiment 93

A compound of Embodiment 92 wherein each $R^{14}$ is independently H.

Embodiment 94

A compound of any one of Embodiments 1 through 93 wherein $R^{15}$ is H, CHO, $C_1$-$C_4$ alkyl, $C_2$-$C_6$ alkylcarbonyl or $C_2$-$C_6$ haloalkylcarbonyl.

Embodiment 95

A compound of Embodiment 94 wherein $R^{15}$ is H, $CH_3$, —(C=O)$CH_3$ or —(C=O)$CF_3$.

Embodiment 96

A compound of Embodiment 95 wherein each $R^{15}$ is independently H or $CH_3$.

Embodiment 97

A compound of any one of Embodiments 1 through 96 wherein each $R^{16}$, $R^{17}$ and $R^{18}$ is independently halogen, cyano, hydroxy, amino, nitro, —CHO, —C(=O)OH, —C(=O)$NH_2$, —$SO_2NH_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_1$-$C_8$ hydroxyalkyl, $C_2$-$C_8$ haloalkylcarbonyl, $C_2$-$C_6$ alkoxyalkyl, $C_2$-$C_6$ alkylaminoalkyl, $C_2$-$C_8$ alkoxycarbonyl, $C_3$-$C_8$ cycloalkyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_3$-$C_8$ dialkylaminoalkyl, $C_1$-$C_6$ alkoxy, $C_1$-$C_6$ haloalkoxy, $C_2$-$C_8$ alkylcarbonyloxy or $C_1$-$C_6$ alkylthio.

Embodiment 98

A compound of Embodiment 97 wherein each $R^{16}$, $R^{17}$ and $R^{18}$ is independently halogen, cyano, hydroxy, amino, nitro, —CHO, —C(=O)OH, —C(=O)$NH_2$, —$SO_2NH_2$, $C_1$-$C_6$ alkyl or $C_1$-$C_6$ haloalkyl.

Embodiment 99

A compound of Embodiment 98 wherein each $R^{16}$, $R^{17}$ and $R^{18}$ is independently halogen, nitro, $C_1$-$C_6$ alkyl or $C_1$-$C_6$ haloalkyl.

Embodiment 100

A compound of Embodiment 99 wherein each $R^{16}$, $R^{17}$ and $R^{18}$ is independently halogen, $C_1$-$C_6$ alkyl or $C_1$-$C_6$ haloalkyl.

Embodiment 101

A compound of Embodiment 100 wherein each $R^{16}$, $R^{17}$ and $R^{18}$ is independently halogen or $C_1$-$C_6$ alkyl.

Embodiment 102

A compound of Embodiment 101 wherein each $R^{16}$, $R^{17}$ and $R^{18}$ is independently halogen.

Embodiment 103

A compound of any one of Embodiments 1 through 102 wherein the sum of u and v is 0.

Embodiment 104

A compound of any one of Embodiments 1 through 102 wherein the sum of u and v is 2.

Embodiments of this invention, including Embodiments 1-104 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-104 above as well as any other embodiments described herein, and any combination thereof, pertain to the compositions and methods of the present invention.

Embodiment A

A compound of Formula 1 wherein
- $R^A$ is H, cyano, CHO, $C_2$-$C_4$ alkylcarbonyl or $C_1$-$C_4$ alkyl;
- $R^B$ is H, CHO, $C_1$-$C_6$ alkyl, $C_2$-$C_6$ alkenyl, $C_3$-$C_6$ alkynyl, $C_2$-$C_8$ alkoxyalkyl, $C_2$-$C_8$ alkylthioalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl or $C_2$-$C_8$ dialkylaminosulfonyl; or a phenyl ring substituted or unsubstituted with up to 5 substituents independently selected from $R^{16}$; or a 5- to 6-membered heterocyclic ring, substituted or unsubstituted on ring members with up to 5 substituents independently selected from $R^{16}$; or
- $R^A$ and $R^B$ are taken together along with the nitrogen atom to which they are both bonded to form a 5- or 6-membered ring containing ring members selected from carbon, oxygen, nitrogen and —C(=O)—; or taken together as an 6- to 10-membered bicyclic ring system;
- $R^C$ is $C_1$-$C_4$ haloalkyl, $C_2$-$C_4$ haloalkoxycarbonyl or $C_3$-$C_8$ cycloalkyl; or phenyl substituted or unsubstituted with halogen or $C_1$-$C_4$ alkyl; or a 6-membered nitrogen containing aromatic ring substituted or unsubstituted with halogen or $C_1$-$C_4$ alkyl;
- J is —$CR^2R^3$—, —$CR^2R^3$—$CR^4R^5$— or —$NR^6$—;
- Y is O or S;
- $R^1$ is H, CHO, $C_3$-$C_8$ alkylcarbonylalkyl, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ alkylthioalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_2$-$C_8$ alkylaminocarbonyl, $C_3$-$C_{10}$ dialkylaminocarbonyl or $C_4$-$C_{10}$ cycloalkylaminocarbonyl;
- $Q^1$ is a phenyl ring or a naphthalenyl ring system, each ring or ring system substituted or unsubstituted with up to 5 substituents independently selected from $R^{10}$; or a 5- to 6-membered heterocyclic ring; or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 2 carbon ring members are independently selected from C(=O) and C(=S), and the sulfur atom ring members are independently selected from $S(=O)_u(=NR^{14})_v$, each ring or ring system substituted or unsubstituted with up to 4 substituents independently selected from $R^{10}$ on carbon atom ring members and selected from $R^{12}$ on nitrogen atom ring members;
- $Q^2$ is a phenyl ring, each ring substituted or unsubstituted with up to 4 substituents independently selected from $R^{11}$; or a 5- to 6-membered heterocyclic ring; or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 2 carbon ring members are independently selected from C(=O) and C(=S), and the sulfur atom ring members are independently selected from $S(=O)_u(=NR^{14})_v$, each ring or ring system substituted or unsubstituted with up to 4 substituents independently selected from $R^{11}$ on carbon atom ring members and selected from $R^{13}$ on nitrogen atom ring members;
- $R^2$ and $R^3$ are each independently H or $C_1$-$C_4$ alkyl;
- $R^4$ and $R^5$ are each independently H, halogen, $C_1$-$C_4$ alkyl or $C_1$-$C_4$ alkoxy;
- $R^6$ is H, $C_1$-$C_6$ alkyl or $C_1$-$C_6$ alkoxy;
- $R^7$ and $R^8$ are each independently H, halogen, $C_1$-$C_4$ alkoxy or $C_1$-$C_4$ alkyl;
- $R^9$ is H, $C_1$-$C_6$ alkyl, $C_2$-$C_8$ alkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_4$-$C_{10}$ cycloalkylcarbonyl, $C_2$-$C_8$ alkoxycarbonyl or $C_4$-$C_{10}$ cycloalkoxycarbonyl;
- each $R^{10}$ and $R^{11}$ is halogen, nitro, $C_1$-$C_8$ alkyl, $C_1$-$C_8$ cyanoalkyl, $C_1$-$C_8$ cyanoalkoxy, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkoxyhaloalkoxy, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_1$-$C_8$ alkoxy, $C_1$-$C_8$ haloalkoxy, $C_2$-$C_8$ alkenyloxy, $C_2$-$C_8$ haloalkenyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylsulfonyl, $C_1$-$C_8$ haloalkylsulfonyl, $C_3$-$C_8$ cycloalkylsulfonyl;
- each $R^{12}$ and $R^{13}$ is independently $C_1$-$C_3$ alkyl, $C_2$-$C_3$ alkenyl, $C_3$-$C_6$ cycloalkyl, $C_2$-$C_3$ alkoxyalkyl, $C_2$-$C_3$ alkylcarbonyl or $C_2$-$C_3$ alkylaminoalkyl;
- each $R^{14}$ is independently H or —(C=O)CH$_3$;
- each $R^{16}$ is independently halogen, cyano, hydroxy, amino, nitro, —CHO, —C(=O)OH, —C(=O)NH$_2$, —SO$_2$NH$_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_1$-$C_8$ hydroxyalkyl, $C_2$-$C_8$ haloalkylcarbonyl, $C_2$-$C_6$ alkoxyalkyl, $C_2$-$C_6$ alkylaminoalkyl, $C_2$-$C_8$ alkoxycarbonyl, $C_3$-$C_8$ cycloalkyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_3$-$C_8$ dialkylaminoalkyl, $C_1$-$C_6$ alkoxy, $C_1$-$C_6$ haloalkoxy, $C_2$-$C_8$ alkylcarbonyloxy or $C_1$-$C_6$ alkylthio; and
the sum of u and v is 2.

Embodiment B

A compound of Embodiment A wherein
$R^A$ is H, CHO, $C_2$-$C_4$ alkylcarbonyl or $C_1$-$C_4$ alkyl;
$R^B$ is H, $C_1$-$C_6$ alkyl, $C_2$-$C_8$ alkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl or $C_2$-$C_8$ dialkylaminosulfonyl; or a phenyl ring substituted or unsubstituted with up to 4 substituents independently selected from $R^{16}$; or
$R^A$ and $R^B$ are taken together along with the nitrogen atom to which they are both bonded to form a 5- or 6-membered ring containing ring members selected from carbon, oxygen and —C(=O)—; or taken together as a 6- to 10-membered bicyclic ring system;
$R^C$ is $CF_3$, —C(=O)$CF_3$ or cyclopropyl; or phenyl substituted or unsubstituted with halogen or $C_1$-$C_4$ alkyl; or an unsubstituted pyridine or pyrimidine ring;
J is —$CR^2R^3$— or —$CR^2R^3$—$CR^4R^5$—;
Y is O;
$R^1$ is H, $C_3$-$C_8$ alkylcarbonylalkyl, $C_1$-$C_6$ alkyl, $C_1$-$C_6$ haloalkyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_2$-$C_8$ haloalkoxyalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl or $C_2$-$C_8$ haloalkoxycarbonyl;
$Q^1$ is a phenyl ring substituted or unsubstituted with up to 4 substituents independently selected from $R^{10}$; or a 5- to 6-membered heterocyclic ring, each ring containing ring members selected from carbon atoms and 1 to 4 heteroatoms independently selected from up to 2 O, up to 2 S and up to 4 N atoms, each ring substituted or unsubstituted with up to 4 substituents independently selected from $R^{10}$ on carbon atom ring members and selected from $R^{12}$ on nitrogen atom ring members;
$Q^2$ is a phenyl ring, substituted or unsubstituted with up to 4 substituents independently selected from $R^{11}$; or a 5- to 6-membered heterocyclic ring; or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 2 carbon ring members are independently selected from C(=O) and C(=S), and the sulfur atom ring members are independently selected from S(=O)$_u$(=$NR^{14}$)$_v$, each ring or ring system substituted or unsubstituted with up to 4 substituents independently selected from $R^{11}$ on carbon atom ring members and selected from $R^{13}$ on nitrogen atom ring members;
$R^2$ and $R^3$ are each independently H or $CH_3$;
$R^4$ and $R^5$ are each independently H, halogen or $C_1$-$C_4$ alkyl;
$R^7$ and $R^8$ are each independently H, F, $C_1$ or $CH_3$;
$R^9$ is H, $C_1$-$C_6$ alkyl, $C_2$-$C_8$ alkoxyalkyl, $C_2$-$C_8$ alkylcarbonyl or $C_2$-$C_8$ alkoxycarbonyl;
each $R^{10}$ and $R^{11}$ is independently halogen, $C_1$-$C_8$ alkyl, $C_1$-$C_8$ haloalkyl, $C_2$-$C_8$ alkoxyalkyl, $C_3$-$C_8$ alkoxyalkoxyalkyl, $C_4$-$C_{10}$ cycloalkylalkyl, $C_5$-$C_{12}$ alkylcycloalkylalkyl, $C_3$-$C_8$ cycloalkyl, $C_3$-$C_8$ halocycloalkyl, $C_6$-$C_{12}$ cycloalkylcycloalkyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_1$-$C_8$ alkoxy, $C_1$-$C_8$ haloalkoxy, $C_2$-$C_8$ haloalkenyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy or $C_2$-$C_8$ haloalkylcarbonyloxy;
each $R^{12}$ and $R^{13}$ is independently $C_1$-$C_3$ alkyl, $C_3$-$C_6$ cycloalkyl or $C_2$-$C_3$ alkylcarbonyl;
each $R^{14}$ is independently H; and
each $R^{16}$ is independently halogen, cyano, hydroxy, amino, nitro, —CHO, —C(=O)OH, —C(=O)$NH_2$, —$SO_2NH_2$, $C_1$-$C_6$ alkyl or $C_1$-$C_6$ haloalkyl.

Embodiment C

A compound of Embodiment B wherein
W is $NR^AR^B$;
$R^A$ is H or $C_1$-$C_4$ alkyl;
$R^B$ is H, $C_1$-$C_6$ alkyl, $C_2$-$C_8$ alkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl or $C_2$-$C_8$ dialkylaminosulfonyl; or a phenyl ring substituted or unsubstituted with up to 3 substituents independently selected from $R^{16}$;
$R^A$ and $R^B$ are taken together along with the nitrogen atom to which they are both bonded to form a 5-membered ring containing ring members selected from carbon and oxygen; or taken together as a 6- to 9-membered bicyclic ring system;
J is —$CR^2R^3$—;
$R^1$ is H, $C_1$-$C_6$ alkyl, $C_1$-$C_6$ haloalkyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_2$-$C_8$ haloalkoxyalkyl or $C_2$-$C_8$ alkoxycarbonyl;
$Q^1$ is a phenyl ring substituted or unsubstituted with up to 4 substituents independently selected from $R^{10}$;
$Q^2$ is a phenyl ring, substituted or unsubstituted with up to 4 substituents independently selected from $R^{11}$;
$R^2$ and $R^3$ are each independently H or $CH_3$;
$R^7$ and $R^8$ are each independently H or $CH_3$;
$R^9$ is H, $C_1$-$C_6$ alkyl or $C_2$-$C_8$ alkoxycarbonyl;
each $R^{10}$ and $R^{11}$ is independently halogen, $C_1$-$C_8$ alkyl, $C_1$-$C_8$ haloalkyl, $C_2$-$C_8$ alkoxyalkyl, $C_4$-$C_{10}$ cycloalkylalkyl, $C_5$-$C_{12}$ alkylcycloalkylalkyl, $C_3$-$C_8$ cycloalkyl, $C_3$-$C_8$ halocycloalkyl, $C_2$-$C_8$ haloalkoxyalkoxy, $C_1$-$C_8$ alkoxy, $C_1$-$C_8$ haloalkoxy or $C_2$-$C_8$ alkoxyalkoxy;
each $R^{12}$ and $R^{13}$ is independently $C_1$-$C_3$ alkyl or $C_2$-$C_3$ alkylcarbonyl; and
each $R^{16}$ is independently halogen, nitro, $C_1$-$C_6$ alkyl or $C_1$-$C_6$ haloalkyl.

Embodiment D

A compound of Embodiment C wherein
$R^A$ is H or $CH_3$;
$R^B$ is H, $C_2$-$C_8$ alkylcarbonyl, $C_4$-$C_{10}$ cycloalkylcarbonyl, $C_2$-$C_8$ alkoxycarbonyl or $C_4$-$C_{10}$ cycloalkoxycarbonyl; or a phenyl ring substituted or unsubstituted with up to 3 substituents independently selected from $R^{16}$;
$R^1$ is H, $C_1$-$C_6$ alkyl, $C_3$-$C_6$ cycloalkyl, $C_4$-$C_8$ cycloalkylalkyl or $C_2$-$C_8$ alkoxyalkyl;

$Q^1$ is a phenyl ring substituted or unsubstituted with up to 3 substituents independently selected from $R^{10}$;
$Q^2$ is a phenyl ring, substituted or unsubstituted with up to 3 substituents independently selected from $R^{11}$;
$R^2$ and $R^3$ are each independently H;
$R^7$ and $R^8$ are each independently H or F;
$R^9$ is H, $CH_3$ or $—C(=O)OCH_3$;
each $R^{10}$ and $R^{11}$ is independently halogen, $C_1$-$C_8$ alkyl, $C_1$-$C_8$ haloalkyl, $C_1$-$C_8$ alkoxy or $C_1$-$C_8$ haloalkoxy; and
each $R^{16}$ is independently halogen, $C_1$-$C_6$ alkyl or $C_1$-$C_6$ haloalkyl.

Embodiment E

A compound of Embodiment C wherein
$R^A$ and $R^B$ are taken together along with the nitrogen atom to which they are both bonded to form a 5- or 6-membered ring containing ring members selected from carbon and oxygen and $—C(=O)—$; or taken together as a 6- to 10-membered bicyclic ring systems selected from the group consisting of W-1 through W-13 (i.e., as described in Embodiment 15);
$R^r$ is halogen, cyano or $C_1$-$C_4$ alkyl;
r is 0 to 4;
$Q^1$ is a phenyl ring substituted or unsubstituted with up to 3 substituents independently selected from $R^{10}$;
$Q^2$ is a phenyl ring, substituted or unsubstituted with up to 3 substituents independently selected from $R^{11}$;
$R^2$ and $R^3$ are each independently H;
$R^7$ and $R^8$ are each independently H;
$R^9$ is H, $CH_3$ or $—C(=O)OCH_3$;
each $R^{10}$ and $R^{11}$ is independently halogen, $C_1$-$C_8$ alkyl, $C_1$-$C_8$ haloalkyl, $C_1$-$C_8$ alkoxy or $C_1$-$C_8$ haloalkoxy; and
each $R^{16}$ is independently halogen, $C_1$-$C_6$ alkyl or $C_1$-$C_6$ haloalkyl.

Embodiment F

A compound of Embodiment E wherein
$R^A$ and $R^B$ are taken together as a 8- to 9-membered bicyclic ring system selected from W-7, W-8 and W-9;
$R^r$ is halogen or $C_1$-$C_4$ alkyl;
r is 0 to 3;
$Q^1$ is a phenyl ring substituted or unsubstituted with up to 2 substituents independently selected from $R^{10}$;
$Q^2$ is a phenyl ring, substituted or unsubstituted with up to 2 substituents independently selected from $R^{11}$;
$R^9$ is H; and
each $R^{10}$ and $R^{11}$ is independently halogen or $C_1$-$C_8$ haloalkyl.

Embodiment G

A compound of Embodiment B wherein
W is $OR^C$;
$R^C$ is $CF_3$; or phenyl substituted or unsubstituted with halogen; or an unsubstituted pyridine ring;
J is $—CR^2R^3—$;
$Q^1$ is a phenyl ring substituted or unsubstituted with up to 3 substituents independently selected from $R^{10}$;
$Q^2$ is a phenyl ring, substituted or unsubstituted with up to 3 substituents independently selected from $R^{11}$;
$R^2$ and $R^3$ are each independently H;
$R^9$ is H, $C_1$-$C_6$ alkyl or $C_2$-$C_8$ alkoxycarbonyl;
$R^7$ and $R^8$ are each independently H or F;

$R^9$ is H, $CH_3$ or $—C(=O)OCH_3$; and
each $R^{10}$ and $R^{11}$ is independently halogen, $C_1$-$C_8$ alkyl, $C_1$-$C_8$ haloalkyl, $C_1$-$C_8$ alkoxy or $C_1$-$C_8$ haloalkoxy.

A Specific Embodiment of the Invention is the Following Compound of the Summary of the Invention 2-[(3R,4S)-3-[[(2,3-difluorophenyl)amino]carbonyl]-1-methyl-4-[4-(trifluoromethyl)phenyl]-2-pyrrolidinylidene]hydrazide 2,2-dimethylpropanoic Acid (Compound 1)

This invention also relates to a method for controlling undesired vegetation comprising applying to the locus of the vegetation herbicidally effective amounts of the compounds of the invention (e.g., as a composition described herein). Of note as embodiments relating to methods of use are those involving the compounds of embodiments described above. Compounds of the invention are particularly useful for selective control of weeds in crops such as wheat, barley, maize, soybean, sunflower, cotton, oilseed rape and rice, and specialty crops such as sugarcane, citrus, fruit and nut crops.

Also noteworthy as embodiments are herbicidal compositions of the present invention comprising the compounds of embodiments described above.

This invention also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid and pyributicarb, and (b16) herbicide safeners; and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, desmetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol, pyridate, siduron, simazine, simetryn, tebuthiuron, terbacil, terbumeton, terbuthylazine, terbutryn and trietazine.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for protein synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-sodium, foramsulfuron, halosulfuron-methyl, imazamethabenz-methyl, imazamox, imazapic, imazapyr, imazaquin, imazethapyr, imazosulfuron, iodosulfuron-methyl (including sodium salt), iofensulfuron (2-iodo-N-[[(4-methoxy-6-methyl-1,3,5-triazin-2-yl)amino]carbonyl]benzenesulfonamide), mesosulfuron-methyl, metazosulfuron (3-chloro-4-(5,6-dihydro-5-methyl-1,4,2-dioxazin-3-yl)-N-[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuron-methyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethanesulfonamide), triasulfuron, tribenuron-methyl, trifloxysulfuron (including sodium salt), triflusulfuron-methyl and tritosulfuron.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate.

"EPSP synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, cyclopyranil, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, trifludimoxazin (dihydro-1,5-dimethyl-6-thioxo-3-[2,2,7-trifluoro-3,4-dihydro-3-oxo-4-(2-propyn-1-yl)-2H-1,4-benzoxazin-6-yl]-1,3,5-triazine-2,4(1H,3H)-dione) and tiafenacil (methyl N-[2-[[2-chloro-5-[3,6-dihydro-3-methyl-2,6-dioxo-4-(trifluoromethyl)-1(2H)-pyrimidinyl]-4-fluorophenyl]thio]-1-oxopropyl]-β-alaninate).

"GS inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P ((2S)-2-amino-4-(hydroxymethylphosphinyl)butanoic acid) and bilanaphos.

"VLCFA elongase inhibitors" (b9) are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[(2,5-dichloro-4-ethoxyphenyl)methyl]

sulfonyl]-4,5-dihydro-5,5-dimethylisoxazole), fentrazamide, flufenacet, indanofan, mefenacet, metazachlor, metolachlor, napropanilide, napropamide, napropamide-M ((2R)—N,N-diethyl-2-(1-naphthalenyloxy)propanamide), pethoxamid, piperophos, pretilachlor, propachlor, propisochlor, pyroxasulfone, and thenylchlor, including resolved forms such as S-metolachlor and chloroacetamides and oxyacetamides.

"Auxin transport inhibitors" (b10) are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS inhibitors" (b11) are chemical compounds that inhibit carotenoid biosynthesis pathway at the phytoene desaturase step. Examples of PDS inhibitors include beflubutamid, S-beflubutamid, diflufenican, fluridone, flurochloridone, flurtamone norflurzon and picolinafen.

"HPPD inhibitors" (b12) are chemical substances that inhibit the biosynthesis of synthesis of 4-hydroxyphenylpyruvate dioxygenase. Examples of HPPD inhibitors include benzobicyclon, benzofenap, bicyclopyrone (4-hydroxy-3-[[2-[(2-methoxyethoxy)methyl]-6-(trifluoromethyl)-3-pyridinyl]carbonyl]bicyclo[3.2.1]oct-3-en-2-one), fenquinotrione (2-[[8-chloro-3,4-dihydro-4-(4-methoxyphenyl)-3-oxo-2-quinoxalinyl]carbonyl]-1,3-cyclohexanedione), isoxachlortole, isoxaflutole, mesotrione, pyrasulfotole, pyrazolynate, pyrazoxyfen, sulcotrione, tefuryltrione, tembotrione, tolpyralate (1-[[1-ethyl-4-[3-(2-methoxyethoxy)-2-methyl-4-(methylsulfonyl)benzoyl]-1H-pyrazol-5-yl]oxy]ethyl methyl carbonate), topramezone, 5-chloro-3-[(2-hydroxy-6-oxo-1-cyclohexen-1-yl)carbonyl]-1-(4-methoxyphenyl)-2(1H)-quinoxalinone, 4-(2,6-diethyl-4-methylphenyl)-5-hydroxy-2,6-dimethyl-3(2H)-pyridazinone, 4-(4-fluorophenyl)-6-[(2-hydroxy-6-oxo-1-cyclohexen-1-yl)carbonyl]-2-methyl-1,2,4-triazine-3,5(2H,4H)-dione, 5-[(2-hydroxy-6-oxo-1-cyclohexen-1-yl)carbonyl]-2-(3-methoxyphenyl)-3-(3-methoxypropyl)-4(3H)-pyrimidinone, 2-methyl-N-(4-methyl-1,2,5-oxadiazol-3-yl)-3-(methylsulfinyl)-4-(trifluoromethyl)benzamide and 2-methyl-3-(methylsulfonyl)-N-(1-methyl-1H-tetrazol-5-yl)-4-(trifluoromethyl)benzamide.

"HST inhibitors" (b13) disrupt a plant's ability to convert homogentisate to 2-methyl-6-solanyl-1,4-benzoquinone, thereby disrupting carotenoid biosynthesis. Examples of HST inhibitors include haloxydine, pyriclor, 3-(2-chloro-3,6-difluorophenyl)-4-hydroxy-1-methyl-1,5-naphthyridin-2(1H)-one, 7-(3,5-dichloro-4-pyridinyl)-5-(2,2-difluoroethyl)-8-hydroxypyrido[2,3-b]pyrazin-6(5H)-one and 4-(2,6-diethyl-4-methylphenyl)-5-hydroxy-2,6-dimethyl-3(2H)-pyridazinone.

HST inhibitors also include compounds of Formulae A and B.

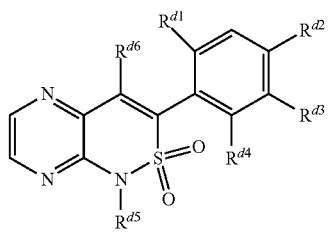

A

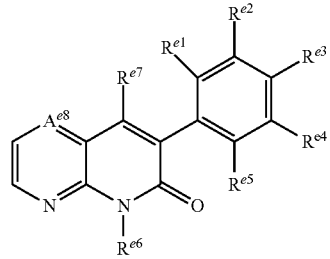

B wherein $R^{d1}$ is H, Cl or $CF_3$; $R^{d2}$ is H, Cl or Br; $R^{d3}$ is H or Cl; $R^{d4}$ is H, Cl or $CF_3$; $R^{d5}$ is $CH_3$, $CH_2CH_3$ or $CH_2CHF_2$; and $R^{d6}$ is OH, or —OC(=O)-i-Pr; and $R^{e1}$ is H, F, Cl, $CH_3$ or $CH_2CH_3$; $R^{e2}$ is H or $CF_3$; $R^{e3}$ is H, $CH_3$ or $CH_2CH_3$; $R^{e4}$ is H, F or Br; $R^{e5}$ is Cl, $CH_3$, $CF_3$, $OCF_3$ or $CH_2CH_3$; $R^{e6}$ is H, $CH_3$, $CH_2CHF_2$ or C≡CH; $R^{e7}$ is OH, —OC(=O)Et, —OC(=O)-i-Pr or —OC(=O)-t-Bu; and $A^{e8}$ is N or CH.

"Cellulose biosynthesis inhibitors" (b14) inhibit the biosynthesis of cellulose in certain plants. They are most effective when applied preemergence or early postemergence on young or rapidly growing plants. Examples of cellulose biosynthesis inhibitors include chlorthiamid, dichlobenil, flupoxam, indaziflam ($N^2$-[(1R,2S)-2,3-dihydro-2,6-dimethyl-1H-inden-1-yl]-6-(1-fluoroethyl)-1,3,5-triazine-2,4-diamine), isoxaben and triaziflam.

"Other herbicides" (b15) include herbicides that act through a variety of different modes of action such as mitotic disruptors (e.g., flamprop-M-methyl and flamprop-M-isopropyl), organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, bromobutide, cinmethylin, clomazone, cumyluron, cyclopyrimorate (6-chloro-3-(2-cyclopropyl-6-methylphenoxy)-4-pyridazinyl 4-morpholinecarboxylate), daimuron, 2-[(2,5-dichlorophenyl)methyl]-4,4-dimethyl-3-isoxazolidinone, difenzoquat, etobenzanid, fluometuron, flurenol, fosamine, fosamine-ammonium, dazomet, dymron, ipfencarbazone (1-(2,4-dichlorophenyl)-N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 5-[[(2,6-difluorophenyl)methoxy]methyl]-4,5-dihydro-5-methyl-3-(3-methyl-2-thienyl)isoxazole.

"Other herbicides" (b15) also include a compound of Formula (b15A),

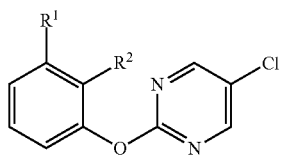

(b15A)

wherein $R^1$ is Cl, Br or CN; and $R^2$ is C(=O)$CH_2CH_2CF_3$, $CH_2CH_2CH_2CF_3$ or 3-$CHF_2$-isoxazol-5-yl. "Other herbicides" (b15) also include a compound of Formula (b15B)

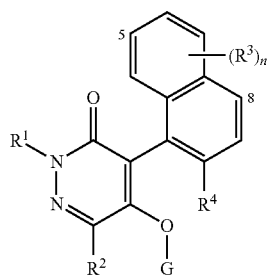

(b15B)

wherein $R^1$ is $CH_3$, $R^2$ is Me, $R^4$ is $OCHF_2$, G is H, and n is 0; $R^1$ is $CH_3$, $R^2$ is Me, $R^3$ is 5-F, $R^4$ is Cl, G is H, and n is 1; $R^1$ is $CH_3$, $R^2$ is Cl, $R^4$ is Me, G is H, and n is 0; $R^1$ is $CH_3$, $R^2$ is Me, $R^4$ is Cl, G is H, and n is 0; $R^1$ is $CH_3$, $R^2$ is Me, $R^3$ is 5-Me, $R^4$ is $OCHF_2$, G is H, and n is 1; $R^1$ is $CH_3$, $R^2$ is Me, $R^3$ is 5-Br, $R^4$ is $OCHF_2$, G is H, and n is 1; $R^1$ is $CH_3$, $R^2$ is Me, $R^3$ is 5-Cl, $R^4$ is Cl, G is H, and n is 1; or $R^1$ is $CH_3$, $R^2$ is $CH_3$, $R^4$ is $OCHF_2$, G is C(O)Me, and n is 0.

"Other herbicides" (b15) also include a compound of Formula (b15C)

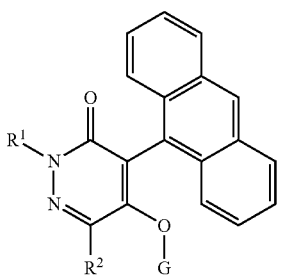

(b15C)

wherein
$R^1$ is $CH_3$, $R^2$ is Cl, and G is H; or
$R^1$ is $CH_3$, $R^2$ is Cl, and G is C(O)Me.

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzenesulfonamide and N-(aminocarbonyl)-2-fluorobenzenesulfonamide, 1-bromo-4-[(chloromethyl)sulfonyl]benzene, 2-(dichloromethyl)-2-methyl-1,3-dioxolane (MG 191), 4-(dichloroacetyl)-1-oxa-4-azospiro[4.5]decane (MON 4660), 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide.

The compounds of Formula 1 can be prepared by general methods known in the art of synthetic organic chemistry. Of note are the following methods described in Schemes 1-X and variations thereof. The definitions of W, $R^1$, J, $Q^1$, $R^7$, $R^8$, $R^9$, $Q^2$, and Y in the compounds of Formulae 1 through 9 below are as defined above in the Summary of the Invention unless otherwise noted. Formulae 1A-1C and 2A are various subsets of a compound of Formulae 1 and 2, respectively. Substituents for each subset Formula are as defined for its parent Formula unless otherwise noted.

As shown in Scheme 1 a compound of Formula 1A (i.e. a compound of Formula 1 wherein Y is O) can be prepared by reaction of thiolactams of Formula 2 with an amine of Formula 3. These reactions can be aided by the addition of an activating agent such as a Lewis or Brønsted acid and are typically run at temperatures ranging from 0 to 120° C. in a solvent such as methanol, ethanol, tetrahydrofuran, acetonitrile, dichloromethane or N,N-dimethylformamide. The method of Scheme 1 utilizing mercuric acetate is illustrated by Step A of Synthesis Example 2.

Scheme 1

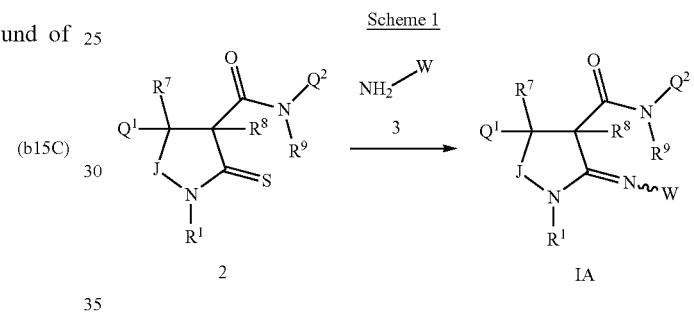

As shown in Scheme 2 a compound of Formula 1A can alternately be prepared by reaction of thioalkyl imidates of Formula 4 with an amine of Formula 3. These reactions are typically run at temperatures ranging from 0 to 120° C. in a solvent such as methanol, ethanol, tetrahydrofuran, acetonitrile, dichloromethane or N,N-dimethylformamide.

Scheme 2

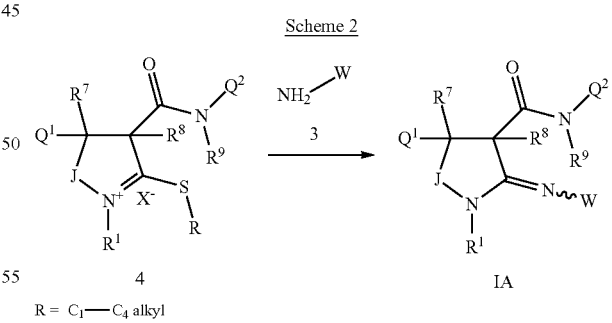

R = $C_1$—$C_4$ alkyl

As shown in Scheme 3 a compound of Formula 4 can be prepared by reaction of a thiolactam of Formula 2 with an alkylating agent. Suitable alkylating agents include, but are not limited to alkyl sulfonates or alkyl halides such as methyl iodide or methyl bromide, such as. These reactions are typically run at reaction temperatures ranging from 0 to 80° C. in a solvent such as acetonitrile, tetrahydrofuran, dichloromethane or N,N-dimethylformamide.

Scheme 3

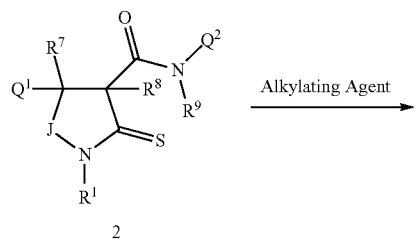

Scheme 5

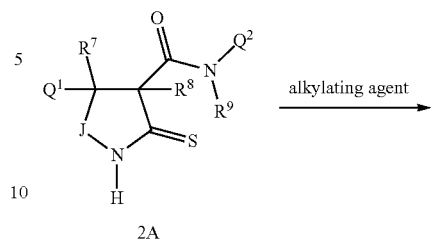

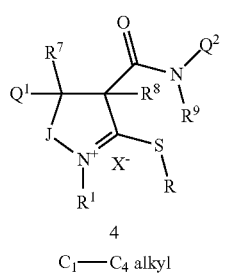

$R = C_1$—$C_4$ alkyl

As shown in Scheme 4 a compound of Formula 1B (i.e. Formula 1 wherein Y is O and $R^1$ is H) can be prepared by reaction of a thioalkyl imidate of Formula 5 with an amine of Formula 3. These reactions are typically run at temperatures ranging from 0 to 120° C. in a solvent such as methanol, ethanol, tetrahydrofuran, acetonitrile, dichloromethane or N,N-dimethylformamide.

Scheme 4

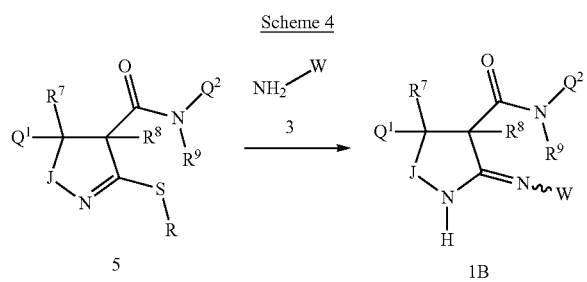

$R = C_1$—$C_4$ alkyl

As shown in Scheme 5, a compound of Formula 5 can be prepared by reaction of a thiolactam of Formula 2A (i.e. a compound of Formula 2 wherein $R^1$ is H) with an alkylating agent. Suitable alkylating agents include, but are not limited to, alkyl sulfonates or alkyl halides such as methyl iodide or methyl bromide. These reactions are typically run at reaction temperatures ranging from 0 to 80° C. in a solvent such as acetonitrile, tetrahydrofuran, dichloromethane or N,N-dimethylformamide in the presence of a base such as, but not limited to, triethylamine or potassium carbonate.

$R = C_1$—$C_4$ alkyl

As shown in Scheme 6 a compound of Formula 2 can be prepared by the reactions of an acid of Formula 6 with an amine of Formula 7 in the presence of a dehydrative coupling reagent such as propylphosphonic anhydride, dicyclohexylcarbodiimide, N-(3-dimethylaminopropyl)-N'-ethylcarbodiimide, N,N'-carbonyldiimidazole, 2-chloro-1,3-dimethylimidazolium chloride or 2-chloro-1-methylpyridinium iodide. Polymer-supported reagents, such as polymer-supported cyclohexylcarbodiimide, are also suitable. These reactions are typically run at temperatures ranging from 0 to 60° C. in a solvent such as dichloromethane, acetonitrile, N,N-dimethylformamide or ethyl acetate in the presence of a base such as triethylamine, N,N-diisopropylamine, or 1,8-diazabicyclo[5.4.0]undec-7-ene. See *Organic Process Research & Development* 2009, 13, 900-906 for coupling conditions employing propylphosphonic anhydride. The method of Scheme 6 utilizing propylphosphonic anhydride is illustrated by Step H of Synthesis Example 1. Substituents in the 2- and 3-positions of ring in a compound of Formula 2, i.e. C(O)N($Q^2$)($R^9$), are predominantly in the trans configuration. In some instances, the presence of minor amounts of the cis isomer can be detected by NMR.

Scheme 6

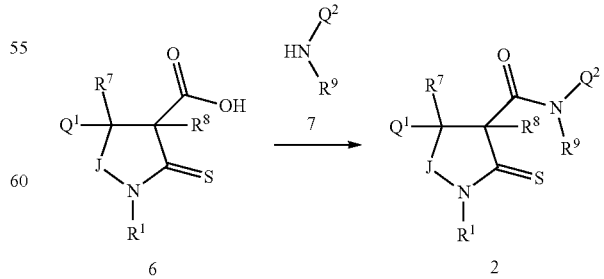

As shown in Scheme 7 a compound of Formula 6 can be prepared by hydrolysis of an ester of Formula 8 by methods well known to those skilled in the art. Hydrolysis is carried out with aqueous base or aqueous acid, typically in the presence of a co-solvent. Suitable bases for the reaction include, but are not limited to, hydroxides such as sodium and potassium hydroxide and carbonates such as sodium and potassium carbonate. Suitable acids for the reaction include, but are not limited to, inorganic acids such as hydrochloric acid, hydrobromic acid and sulfuric acid, and organic acids such as acetic acid and trifluoroacetic acid. A wide variety of co-solvents are suitable for the reaction including, but not limited to, methanol, ethanol and tetrahydrofuran. The reaction is conducted at temperatures ranging from −20° C. to the boiling point of the solvent, and typically from 0 to 100° C. The method of Scheme 7 is illustrated by Step C of Synthesis Example 1.

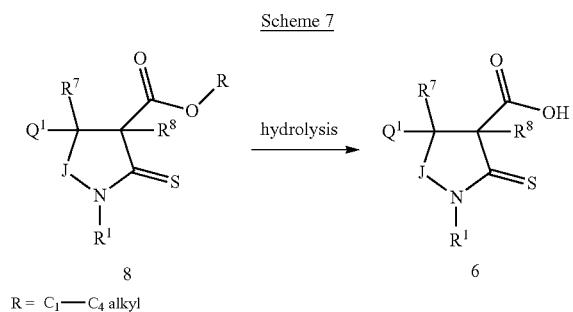

Scheme 7

R = $C_1$—$C_4$ alkyl

As shown in Scheme 8, a compound of Formula 8 can be prepared by reacting a compound of Formula 9 with a thionation reagent such as Lawesson's reagent, tetraphosphorus decasulfide or diphosphorus pentasulfide in a solvent such as tetrahydrofuran or toluene. Typically, the reaction is carried out at temperatures ranging from 0 to 115° C. The method of Scheme 8 utilizing Lawesson's reagent is illustrated by Step F of Synthesis Example 1.

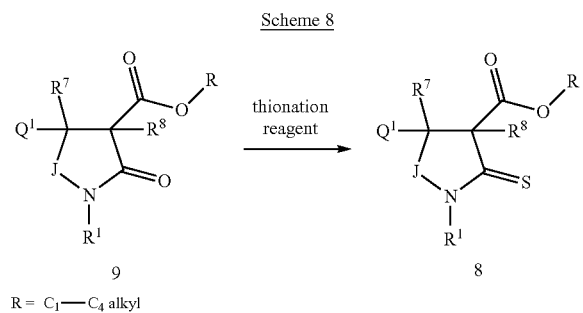

Scheme 8

R = $C_1$—$C_4$ alkyl

Compounds of Formula 9 are known in the literature, see: WO 2016/196593.

As shown in Scheme 9 a compound of Formula 1C (i.e. Formula 1 wherein Y is S) can be prepared by reacting compounds of Formula 1A with a thionation reagent such as Lawesson's reagent, tetraphosphorus decasulfide or diphosphorus pentasulfide in a solvent such as tetrahydrofuran or toluene. Typically, the reaction is carried out at temperatures ranging from 0 to 115° C.

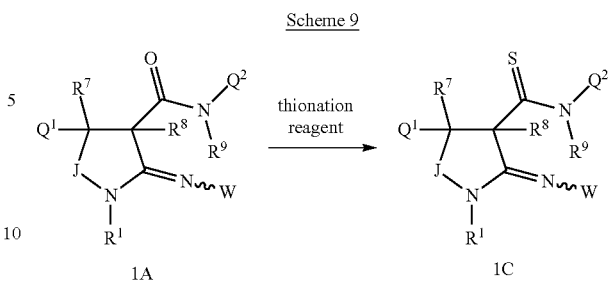

Scheme 9

It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations*, 2nd Ed., Wiley-VCH, New York, 1999. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1. The above reactions can also in many cases be performed in alternate order It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane CDCl$_3$ at 400 MHz unless otherwise noted; "s" means singlet, "d" means doublet, "t" means triplet, "q" means quartet, "m" means multiplet and "bs" means broad singlet.

Synthesis Example 1

Preparation of (3R,4S)—N-(2,3-difluorophenyl)-2-hydrazinylidene-1-methyl-4-[4-(trifluoromethyl)phenyl]-3-pyrrolidinecarboxamide (Compound 2)

Step A: Preparation of 1,3 diethyl 2-[(1S)-2-nitro-1-[4-(trifluoromethyl)phenyl]ethyl]-propanedioate To a solution of 1-i[(1E)-2-nitroethenyl]-4-(trifluoromethyl)benzene (14 g, 64.5 mmol) in toluene (70 mL), was added diethyl malonate (12.38 g, 77.4 mmol) and bis[(1R,2R)—N$^1$,N$^2$-bis(phenylmethyl)-1,2-cyclohexanediamine-κN$^1$,κN$^2$]dibromonickel (OC-6-12) (CAS Registry No. 941321-23-9) (1.03 g, 1.29 mmol). The reaction mixture was stirred at room temperature for 48 h. The reaction mixture was then concentrated in vacuo to give the crude product which was charged onto silica and purified by medium pressure liquid chromatography (10% ethyl acetate in petroleum ether as eluent) to provide 25 g of the title compound.

Step B: Preparation of ethyl (3R,4S)-2-oxo-4-[4-(trifluoromethyl)phenyl]-3-pyrrolidinecarboxylate To a solution of 1,3-diethyl 2-[(1S)-2-nitro-1-[4-(trifluoromethyl)phenyl]ethyl]-propanedioate (i.e. the product of Step A) (25 g, 66.31 mmol) in ethanol (250 mL) and water (38 mL) was added iron powder (18.56 g, 331.56 mmol) and ammonium chloride (1.79 g, 33.15 mmol) and the reaction mixture was heated at 100° C. After 16 h the reaction mixture was filtered through Celite® diatomaceaous earth filter aid and concentrated in vacuo. The residue was diluted with water and extracted with ethyl acetate three times. The combined organic layers were washed with water and brine and dried over Na$_2$SO$_4$. The solvent was concentrated in vacuo to give the crude compound which was washed with n-pentane to yield 10.6 g of the title compound melting at 125-129° C.

Step C: Preparation of (3R,4S)-2-oxo-4-[4-(trifluoromethyl)phenyl]-3-pyrrolidinecarboxylic Acid To a solution of ethyl (3R,4S)-2-oxo-4-[4-(trifluoromethyl)phenyl]-3-pyrrolidinecarboxylate (i.e. the product of Step B) (9.6 g, 31.89 mmol) in ethanol (100 mL) and water (100 mL) was added sodium hydroxide (3.82 g, 95.68 mmol) at 0° C. The reaction mixture was stirred at room temperature for 16 h after which the reaction mixture was concentrated in vacuo and the solid was dissolved in water. The aqueous layer was acidified to pH 1 with 6 N HCl at 0° C., and the resultant solid was collected by filtration and dried under vacuum to yield 8.2 g (94% yield) of the title compound as an off white solid melting at 120-122° C.

Step D: Preparation of (3R,4S)-1-methyl-2-oxo-4-[4-(trifluoromethyl)phenyl]-3-pyrrolidinecarboxylic Acid (3R,4S)-2-Oxo-4-[4-(trifluoromethyl)phenyl]-3-pyrrolidinecarboxylic acid (i.e. the product of Step C) (5 g, 18.31 mmol) in tetrahydrofuran (5 mL) was slowly added to potassium t-butoxide (1 N in tetrahydrofuran, 54.9 mL, 54.9 mmol) at 0° C. After 10 min, bromomethane (25% in toluene, 17.39 mL, 45.78 mmol) was added and the reaction mixture was stirred at room temperature. After 12 h the reaction mixture was diluted with ethyl acetate and acidified to pH 1 with 1 N HCl at 0° C. The resultant solid was collected by filtration and dried under vacuum. The crude solid was washed with n-pentane to yield 4.6 g of the title compound as an off-white solid melting at 143-147° C.
$^1$H NMR (dmso d$_6$) δ 12.8 (bs, 1H), 7.73-7.71 (d, 2H), 7.59-7.57 (d, 2H), 3.94-3.89 (m, 1H), 3.77-3.72 (t, 1H), 3.61-3.58 (d, 1H), 3.41-3.26 (m, 1H), 2.80 (s, 3H).

Step E: Preparation of methyl (3R,4S)-1-methyl-2-oxo-4-[4-(trifluoromethyl)phenyl]-3-pyrrolidinecarboxylate To a solution of (3R,4S)-1-methyl-2-oxo-4-[4-(trifluoromethyl)phenyl]-3-pyrrolidinecarboxylic acid (i.e. the product of Step D) (2.5 g, 8.71 mmol) in methanol (30 mL) was added sulfuric acid (2.5 mL) and the reaction mixture was heated at 90° C. After 16 h the reaction mixture was concentrated in vacuo and diluted with water. The aqueous layer was extracted with ethyl acetate twice and the combined organics were washed with water and brine and dried over Na$_2$SO$_4$. The solvent was removed and the resultant solid was washed with n-pentane to yield 2.25 g of the title compound as an off-white solid melting at 89-91° C.
$^1$H NMR δ 7.62-7.60 (d, 2H), 7.36-7.34 (d, 2H), 4.07-4.06 (d, 1H), 3.85-3.80 (m, 1H), 3.78 (s, 3H), 3.59-3.56 (d, 1H), 3.44-3.39 (m, 1H), 2.95 (s, 3H).

Step F: Preparation of methyl (3S,4S)-1-methyl-2-thioxo-4-[4-(trifluoromethyl)phenyl]-3-pyrrolidinecarboxylate To a solution of methyl (3R,4S)-1-methyl-2-oxo-4-[4-(trifluoromethyl)phenyl]-3-pyrrolidinecarboxylate (i.e. the product of Step E) (2 g, 6.64 mmol) in toluene (40 mL) was added Lawesson's reagent (3.22 g, 7.9 mmol) and the reaction mixture was stirred at 125° C. After 3 h the reaction mixture was diluted with water and extracted with ethyl acetate (3×). The combined organic layers were washed with water and brine and dried over Na$_2$SO$_4$. The organics were then concentrated under reduced pressure to give a crude material which was purified by silica gel chromatography eluting with 15% ethyl acetate in petroleum to yield 2 g of the title compound as a solid melting at 152-156° C.
$^1$H NMR δ 7.62-7.60 (d, 2H), 7.33-7.31 (d, 2H), 4.26-4.21 (m, 1H), 4.07-4.02 (m, 2H), 3.81 (s, 3H), 3.78-3.75 (m, 1H), 3.34 (s, 3H).

Step G: Preparation of (3S,4S)-1-methyl-2-thioxo-4-[4-(trifluoromethyl)phenyl]-3-pyrrolidinecarboxylic Acid To a solution of methyl (3S,4S)-1-methyl-2-thioxo-4-[4-(trifluoromethyl)phenyl]-3-pyrrolidinecarboxylate (i.e. the product of Step F) (0.6 g, 1.89 mmol) in ethanol (20 mL) and H$_2$O (20 mL) was added sodium hydroxide (0.23 g, 5.68 mmol) at 0° C. The reaction mixture was stirred at room temperature for 16 h. The reaction mixture was then concentrated in vacuo and the resultant solid was dissolved in water. The aqueous mixture was acidified to pH 1 with 6 N hydrochloric acid at 0° C. The resultant solid was collected by filtration and dried under vacuum to yield 0.57 g of the title compound as a solid melting at 104-108° C.

¹H NMR (dmso d₆) δ 12.85 (bs, 1H), 7.74-7.72 (d, 2H), 7.57-7.55 (d, 2H), 4.21-4.17 (m, 1H), 4.02-3.95 (m, 1H), 3.90-3.78 (m, 2H), 3.23 (s, 3H).

Step H: Preparation of (3S,4S)—N-(2,3-difluorophenyl)-1-methyl-2-thioxo-4-[4-(trifluoromethyl)phenyl]-3-pyrrolidinecarboxamide To a solution of (3S,4S)-1-methyl-2-thioxo-4-[4-(trifluoromethyl)phenyl]-3-pyrrolidinecarboxylic acid (i.e. the product of Step G) (0.5 g, 1.65 mmol) in N,N-dimethylformamide (5 mL) and dichloromethane (40 mL) was added triethylamine (0.71 mL, 4.95 mmol) and 2,3-difluoroaniline (0.42 g, 3.30 mmol). The reaction mixture was stirred at room temperature for 10 min, then propylphosphonic anhydride (T3P®) (50% in ethyl acetate, 2.25 mL, 3.30 mmol) was added at 0° C. After stirring for 12 h at room temperature the reaction mixture was diluted with water and extracted with ethyl acetate three times. The combined organic layers were washed with water and brine and dried over Na₂SO₄. The organic layers were then concentrated under reduced pressure to give a crude material which was purified by silica gel chromatography eluting with 20% ethyl acetate in petroleum ether to give 0.32 g of the title compound as an off-white solid melting at 183-187° C.

¹H NMR δ 10.05 (bs, 1H), 7.98-7.95 (t, 1H), 7.63-7.40 (d, 2H), 7.40-7.26 (d, 2H), 7.06-6.99 (m, 1H), 6.94-6.87 (m, 1H), 4.48-4.43 (m, 1H), 4.28-4.23 (m, 1H), 4.04-4.03 (d, 1H), 3.77-3.73 (q, 1H), 3.36 (s, 3H).

Step I: Preparation of (3R,4S)—N-(2,3-difluorophenyl)-2-hydrazinylidene-1-methyl-4-[4-(trifluoromethyl)phenyl]-3-pyrrolidinecarboxamide To a solution of (3S,4S)—N-(2,3-difluorophenyl)-1-methyl-2-thioxo-4-[4-(trifluoromethyl)phenyl]-3-pyrrolidinecarboxamide (i.e. the product of Step H) (0.2 g, 0.48 mmol) in methanol (10 mL) was added hydrazine hydrate (2.0 mL) and the reaction mixture was stirred at room temperature. After 48 h the reaction mixture was concentrated under reduced pressure and the resultant solid was washed with n-pentane to yield 80 mg of the title compound as a solid melting at 120-123° C.

¹H NMR δ 12.09 (s, 1H), 8.10-8.07 (m, 1H), 7.61-7.58 (d, 2H), 7.32-7.30 (d, 2H), 7.07-6.99 (m, 1H), 6.90-6.84 (m, 1H), 6.17 (bs, 2H), 4.34-4.33 (d, 1H), 4.16 (s, 1H), 4.03-3.99 (m, 1H), 3.32-3.30 (d, 1H), 2.93 (s, 3H).

Synthesis Example 2

Preparation of 2-[(3R,4S)-3-[[(2,3-difluorophenyl)amino]carbonyl]-1-methyl-4-[4-(trifluoromethyl)phenyl]-2-pyrrolidinylidene]hydrazide 2,2-dimethylpropanoic Acid (Compound 1)

Step A: Preparation of 2-[(3R,4S)-3-[[(2,3-difluorophenyl)amino]carbonyl]-1-methyl-4-[4-(trifluoromethyl)phenyl]-2-pyrrolidinylidene]hydrazide 2,2-dimethylpropanoic Acid To a solution of (3S,4S)—N-(2,3-difluorophenyl)-1-methyl-2-thioxo-4-[4-(trifluoromethyl)phenyl]-3-pyrrolidinecarboxamide (i.e. the product of Step H in Synthesis Example 1) (150 mg, 0.36 mmol) in tetrahydrofuran (15 mL) was added mercury(II) acetate (230 mg, 7.24 mmol) and pivolyl hydrazide (84.5 mg, 7.24 mmol) and the reaction mixture was heated to 90° C. After 12 h the reaction mixture was cooled to room temperature and filtered through Celite® diatomaceaous earth filter aid. The filtrate was concentrated under reduced pressure and the crude material was purified by preparatory high-performance liquid chromatography to yield 25 mg of a of the title compound as a solid (71:26 mixture of isomers) melting at 240-244° C.

¹H NMR δ 10.11 (s, 1H), 9.17 (s, 1H), 7.73-7.71 (d, 2H), 7.67-7.61 (d, 3H), 7.17-7.14 (t, 2H), 4.03-4.02 (d, 1H), 3.85-3.80 (t, 1H), 3.69-3.68 (d, 1H), 3.36 (s, 1H), 2.87 (s, 3H), 1.02 (s, 9H).

By the procedures described herein together with methods known in the art, the following compounds of Table 1 through 12 can be prepared. The following abbreviations are used in the Tables which follow: t means tertiary, i means iso, c means cyclo, Et means ethyl, Pr means propyl, Bu means butyl, i-Pr means isopropyl, Bu means butyl, c-Pr cyclopropyl, c-Bu means cyclobutyl, Ph means phenyl, Py means pyridinyl, S(=O) means sulfinyl, and S(=O)₂ means sulfonyl.

TABLE 1

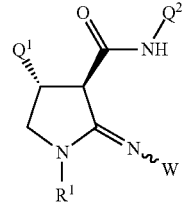

$R^1$ is $CH_3$; $Q^1$ is $Ph(4-CF_3)$; $Q^2$ is $Ph(2,3-di-F)$; and W is W

—NHCH₃
—NHEt
—NH—i-Pr
—NH—t-Bu
—NH-c-Pr
—NH-c-pentyl
—NH-c-hexyl
—N(CH₃)₂
—NCH₃Et
—NCH₃—i-Pr
—NCH₃—t-Bu
—NCH₃-c-Pr
—NCH₃-c-pentyl
—NCH₃-c-hexyl
—NEt₂
—Net-i-Pr
—NEt—t-Bu
—NEt—c-Pr
—NEt-c-pentyl
—NEt-c-hexyl
—NHPh
—NCH₃Ph
—NEtPh
—NHPh(2-F)
—NHPh(3-F)
—NHPh(4-F)
—NHPh(2-CH₃)
—NHPh(3-CH₃)
—NHPh(4-CH₃)
—NH-2-Py
—NH-3-Py
—NH-4-Py
—NHCN
—NH(C=O)H
—NH(C=O)CH₃
—NH(C=O)Et
—NH(C=O)—i-Pr
—NH(C=O)CF₃
—NH(C=O)Ph
—NH(C=O)OCH₃
—NH(C=O)OEt TABLE 1-continued

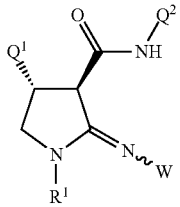

R¹ is CH₃; Q¹ is Ph(4-CF₃); Q² is Ph(2,3-di-F); and W is

W

—NH(C=O)O—i-Pr
—NH(C=O)O—t-Bu
—NH(C=O)OCF₃
—NH(C=O)OPh
—NH(S=O)CH₃
—NH(S=O)Et
—NH(S=O)—i-Pr
—NH(S=O)—t-Bu
—NH(S=O)CF₃
—NH(S=O)Ph
—NH(S=O)OCH₃
—NH(S=O)OEt
—NH(S=O)O—i-Pr
—NH(S=O)O—t-Bu
—NH(S=O)OCF₃

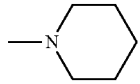

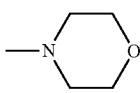

—NH(S=O)OPh
—NH(S(=O)₂)CH₃
—NH(S(=O)₂)Et
—NH(S(=O)₂)—i-Pr
—NH(S(=O)₂)—t-Bu
—NH(S(=O)₂)CF₃
—NH(S(=O)₂)Ph
—NH(S(=O)₂)OCH₃
—NH(S(=O)₂)OEt
—NH(S(=O)₂)O—i-Pr
—NH(S(=O)₂)O—t-Bu
—NH(S(=O)₂)OCF₃
—NH(S(=O)₂)OPh
—OCF₃
—OCF₂CF₃
—OCH₂CF₃
—O-c-Pr

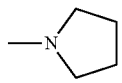

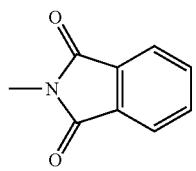

—O-c-pentyl
—O-c-hexyl
—OPh
—OPh(2-F)
—OPh(3-F)
—OPh(4-F)
—OPh(2-CH₃)
—OPh(3-CH₃)
—OPh(4-CH₃)

TABLE 1-continued

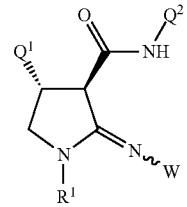

R¹ is CH₃; Q¹ is Ph(4-CF₃); Q² is Ph(2,3-di-F); and W is

W

—O-2-Py
—O-3-Py
—O-4-Py
—O(C=O)CF₃
—O(C=O)CF₂CF₃
—O(C=O)CH₂CF₃

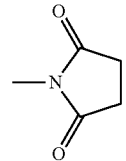

Table 2 is constructed in the same manner as Table 1 except that the Row Heading "R¹ is CH₃; Q¹ is Ph(4-CF₃); Q² is Ph(2,3-di-F); and W is" is replaced with the Row Heading listed for Table 2 below (i.e. "R¹ is CH₃; Q¹ is Ph(4-CF₃); Q² is Ph(2-F) and W is". Tables 3 through 12 are constructed similarly.

| Table | Row Heading |
|---|---|
| 2 | R¹ is CH₃; Q¹ is Ph(4-CF₃); Q² is Ph(2-F); and W is |
| 3 | R¹ is CH₃; Q¹ is Ph(4-CF₃); Q² is 3-Pyr(2,6-di-F); and W is |
| 4 | R¹ is CH₃; Q¹ is Ph(3-CF₃); Q² is Ph(2,3-di-F); and W is |
| 5 | R¹ is CH₃; Q¹ is Ph(3-CF₃); Q² is Ph(2-F); and W is |
| 6 | R¹ is CH₃; Q¹ is Ph(3-CF₃); Q² is 3-Pyr(2,6-di-F); and W is |
| 7 | R¹ is CH₃; Q¹ is 3-Pyr(6-CF₃); Q² is Ph(2,3-di-F); and W is |
| 8 | R¹ is CH₃; Q¹ is 3-Pyr(6-CF₃); Q² is Ph(2-F); and W is |
| 9 | R¹ is CH₃; Q¹ is 3-Pyr(6-CF₃); Q² is 3-Pyr(2,6-di-F); and W is |
| 10 | R¹ is CH₃; Q¹ is 4-Pyr(2-OCHF₂,6-CH₃); Q² is Ph(2,3-di-F); and W is |
| 11 | R¹ is CH₃; Q¹ is 4-Pyr(2-OCHF₂,6-CH₃); Q² is Ph(2-F); and W is |
| 12 | R¹ is CH₃; Q¹ is 4-Pyr(2-OCHF₂,6-CH₃); Q² is 3-Pyr(2,6-di-F); and W is |

A compound of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, U K, 2000.

In the following Examples, all percentages are by weight and all formulations are prepared in conventional ways. Compound numbers refer to compounds in Index Table A.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

High Strength Concentrate

| | |
|---|---|
| Compound 1 | 98.5% |
| silica aerogel | 0.5% |
| synthetic amorphous fine silica | 1.0% |

Example B

Wettable Powder

| | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

Granule

| | |
|---|---|
| Compound 1 | 10.0% |
| attapulgite granules (low volatile matter, 0.71/0.30 mm; U.S.S. No. 25-50 sieves) | 90.0% |

Example D

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

Emulsifiable Concentrate

| | |
|---|---|
| Compound 1 | 10.0% |
| polyoxyethylene sorbitol hexoleate | 20.0% |
| $C_6$-$C_{10}$ fatty acid methyl ester | 70.0% |

Example F

Microemulsion

| | |
|---|---|
| Compound 1 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

Suspension Concentrate

| | |
|---|---|
| Compound 1 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example H

Emulsion in Water

| | |
|---|---|
| Compound 1 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example I

Oil Dispersion

| | |
|---|---|
| Compound 1 | 25% |
| polyoxyethylene sorbitol hexaoleate | 15% |
| organically modified bentonite clay | 2.5% |
| fatty acid methyl ester | 57.5% |

The present disclosure also includes Examples A through I above except "Compound 1" is replaced with "Compound 2", "Compound 3", "Compound 4", "Compound 5", "Compound 6", "Compound 7" or "Compound 8". Test results indicate that the compounds of the present invention are highly active preemergent and/or postemergent herbicides and/or plant growth regulants. The compounds of the invention generally show highest activity for postemergence weed control (i.e. applied after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g., loblolly pine), and turf species (e.g., Kentucky bluegrass, St. Augustine grass, Kentucky fescue and Bermuda grass). Compounds of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the invention have both preemergent and postemergent herbicidal activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation. Undesired vegetation includes at least one selected from the group consisting of grass weeds and broadleaf weeds. Undesired vegetation is selected from the group consisting of annual bluegrass, Benghal dayflower, blackgrass, black nightshade, broadleaf signalgrass, Canada thistle, cheat, common cocklebur (*Xanthium pensylvanicum*), common ragweed, corn poppies, field violet, giant foxtail, goosegrass, green foxtail, guinea grass, hairy beggarticks, herbicide-resistant black grass, horseweed, Italian rye grass, jimsonweed, Johnson grass (*Sorghum halepense*), large crabgrass, little seed canary grass, morning glory, Pennsylvania smartweed, pitted morning glory, prickly sida, quackgrass, redroot pigweed, shattercane, shepherd's purse, silky windgrass, sunflower (as a weed in a potato crop), wild buckwheat (*Polygonum convolvulus*), wild mustard (*Brassica kaber*), wild oat (*Avena fatua*), wild pointsettia, yellow foxtail, and yellow nutsedge (*Cyperus esculentus*).

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.001 to 20 kg/ha with a preferred range of about 0.004 to 1 kg/ha. One skilled in the art can easily determine the herbicidally effective amount necessary for the desired level of weed control.

In one common embodiment, a compound of the invention is applied, typically in a formulated composition, to a locus comprising desired vegetation (e.g., crops) and undesired vegetation (i.e. weeds), both of which may be seeds, seedlings and/or larger plants, in contact with a growth medium (e.g., soil). In this locus, a composition comprising a compound of the invention can be directly applied to a plant or a part thereof, particularly of the undesired vegetation, and/or to the growth medium in contact with the plant.

Plant varieties and cultivars of the desired vegetation in the locus treated with a compound of the invention can be obtained by conventional propagation and breeding methods or by genetic engineering methods. Genetically modified plants (transgenic plants) are those in which a heterologous gene (transgene) has been stably integrated into the plant's genome. A transgene that is defined by its particular location in the plant genome is called a transformation or transgenic event.

Genetically modified plant cultivars in the locus which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect-resistance, modified oil profiles or drought tolerance.

Although most typically, compounds of the invention are used to control undesired vegetation, contact of desired vegetation in the treated locus with compounds of the invention may result in super-additive or synergistic (enhanced) effects with genetic traits in the desired vegetation, including traits incorporated through genetic modification. For example, resistance to phytophagous insect pests or plant diseases, tolerance to biotic/abiotic stresses or storage stability may be greater than expected from the genetic traits in the desired vegetation.

Compounds of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the invention with other herbicides can broaden the spectrum of activity against additional weed species, and suppress the proliferation of any resistant biotypes. Thus the present invention also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, S-beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, clodinafop-propargyl, clomazone, clomeprop, clopyralid, clopyralid-olamine, cloransulam-methyl, cumyluron, cyanazine, cycloate, cyclopyranil, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, hydantocidin, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metamsodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, tolpyralate, topramezone, tralkoxydim, triallate, triafamone, triasulfuron, triaziflam, tribenuron-methyl, triclopyr, triclopyr-butotyl, triclopyr-triethylammonium, tridiphane, trietazine, trifloxysulfuron, trifludimoxazin, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3 (2H)-pyridazinone), 5-[[(2,6-difluorophenyl)methoxy]methyl]-4,5-dihydro-5-methyl-3-(3-methyl-2-thienyl)isoxazole (previously methioxolin), 4-(4-fluorophenyl)-6-[(2-hydroxy-6-oxo-1-cyclohexen-1-yl)carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methylsulfonyl)-N-(1-methyl-1H-tetrazol-5-yl)-4-(trifluoromethyl)benzamide and 2-methyl-N-(4-methyl-1,2,5-oxadiazol-3-yl)-3-(methylsulfinyl)-4-(trifluoromethyl)benzamide. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Preferred for better control of undesired vegetation (e.g., lower use rate such as from greater-than-additive effects, broader spectrum of weeds controlled, or enhanced crop safety) or for preventing the development of resistant weeds are mixtures of a compound of this invention with a herbicide selected from the group consisting of atrazine, azimsulfuron, beflubutamid, S-beflubutamide, benzisothiazolinone, carfentrazone-ethyl, chlorimuron-ethyl, chlorsulfuron-methyl, clomazone, clopyralid potassium, cloransulam-methyl, 2-[(2,5-dichlorophenyl)methyl]-4,4-dimethyl-3-isoxazolidinone, ethametsulfuron-methyl, flumetsulam, 4-(4-fluorophenyl)-6-[(2-hydroxy-6-oxo-1-cyclohexen-1-yl)carbonyl]-2-methyl-i 1,2,4-triazine-3,5-(2H, 4H)-dione, flupyrsulfuron-methyl, fluthiacet-methyl, fomesafen, imazethapyr, lenacil, mesotrione, metribuzin, metsulfuron-methyl, pethoxamid, picloram, pyroxasulfone, quinclorac, rimsulfuron, S-metolachlor, sulfentrazone, thifensulfuron-methyl, triflusulfuron-methyl and tribenuron-methyl.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual,* 13th Edition, C. D. S. Tomlin, Ed., British Crop Protection Council, Farnham, Surrey, U. K., 2003 and *The BioPesticide Manual,* 2nd Edition, L. G. Copping, Ed., British Crop Protection Council, Farnham, Surrey, U. K., 2001.

For embodiments where one or more of these various mixing partners are used, the mixing partners are typically used in the amounts similar to amounts customary when the mixture partners are used alone. More particularly in mixtures, active ingredients are often applied at an application rate between one-half and the full application rate specified on product labels for use of active ingredient alone. These amounts are listed in references such as *The Pesticide Manual* and *The BioPesticide Manual.* The weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this invention with other biologically active (particularly herbicidal) compounds or agents (i.e. active ingredients) can result in a greater-than-additive (i.e. synergistic (enhanced)) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When synergism (enhanced effects) of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the invention with at least one other herbicidal active ingredient. Of particular note is such a combination where the other herbicidal active ingredient has different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Compounds of this invention can also be used in combination with herbicide safeners such as allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride (1,8- naphthalic anhydride), oxabetrinil, N-(aminocarbonyl)-2-methylbenzenesulfonamide, N-(aminocarbonyl)-2-fluorobenzenesulfonamide, 1-bromo-4-[(chloromethyl) sulfonyl]benzene (BCS), 4-(dichloroacetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimidinecarboxylate, 2,2-dichloro-1-(2,2,5-trimethyl-3-oxazolidinyl)-ethanone and 2-methoxy-N-[[4-[[(methylamino)carbonyl] amino]phenyl]sulfonyl]-benzamide to increase safety to certain crops. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Compounds of the invention cans also be mixed with: (1) polynucleotides including but not limited to DNA, RNA, and/or chemically modified nucleotides influencing the amount of a particular target through down regulation, interference, suppression or silencing of the genetically derived transcript that render a herbicidal effect; or (2) polynucleotides including but not limited to DNA, RNA, and/or chemically modified nucleotides influencing the amount of a particular target through down regulation, interference, suppression or silencing of the genetically derived transcript that render a safening effect.

Of note is a composition comprising a compound of the invention (in a herbicidally effective amount), at least one additional active ingredient selected from the group consisting of other herbicides and herbicide safeners (in an effective amount), and at least one component selected from the group consisting of surfactants, solid diluents and liquid diluents.

Table A1 lists specific combinations of a Component (a) with Component (b) illustrative of the mixtures, compositions and methods of the present invention. Compound 1 (i.e. "Cmpd. No." stands for "Compound Number") in the Component (a) column is identified in Index Table A. The second column of Table A1 lists the specific Component (b) compound (e.g., "2,4-D" in the first line). The third, fourth and fifth columns of Table A1 lists ranges of weight ratios for rates at which the Component (a) compound is typically applied to a field-grown crop relative to Component (b) (i.e. (a):(b)). Thus, for example, the first line of Table A1 specifically discloses the combination of Component (a) (i.e. Compound 1 in Index Table A) with 2,4-D is typically applied in a weight ratio between 1:192-6:1. The remaining lines of Table A1 are to be construed similarly.

TABLE A1

| Component (a) (Cmpd. No.) | Component (b) | Typical Weight Ratio | More Typical Weight Ratio | Most Typical Weight Ratio |
|---|---|---|---|---|
| 1 | 2,4-D | 1:192-6:1 | 1:64-2:1 | 1:24-1:3 |
| 1 | Acetochlor | 1:768-2:1 | 1:256-1:2 | 1:96-1:11 |
| 1 | Acifluorfen | 1:96-12:1 | 1:32-4:1 | 1:12-1:2 |
| 1 | Aclonifen | 1:857-2:1 | 1:285-1:3 | 1:107-1:12 |
| 1 | Alachlor | 1:768-2:1 | 1:256-1:2 | 1:96-1:11 |
| 1 | Ametryn | 1:384-3:1 | 1:128-1:1 | 1:48-1:6 |
| 1 | Amicarbazone | 1:192-6:1 | 1:64-2:1 | 1:24-1:3 |
| 1 | Amidosulfuron | 1:6-168:1 | 1:2-56:1 | 1:1-11:1 |
| 1 | Aminocyclo-pyrachlor | 1:48-24:1 | 1:16-8:1 | 1:6-2:1 |
| 1 | Aminopyralid | 1:20-56:1 | 1:6-19:1 | 1:2-4:1 |
| 1 | Amitrole | 1:768-2:1 | 1:256-1:2 | 1:96-1:11 |
| 1 | Anilofos | 1:96-12:1 | 1:32-4:1 | 1:12-1:2 |
| 1 | Asulam | 1:960-2:1 | 1:320-1:3 | 1:120-1:14 |
| 1 | Atrazine | 1:192-6:1 | 1:64-2:1 | 1:24-1:3 |
| 1 | Azimsulfuron | 1:6-168:1 | 1:2-56:1 | 1:1-11:1 |
| 1 | Beflubutamid | 1:342-4:1 | 1:114-2:1 | 1:42-1:5 |
| 1 | S-Beflubutamid | 1:171-4:0.5 | 1:57-2:0.5 | 1:21-1:2.5 |
| 1 | Benfuresate | 1:617-2:1 | 1:205-1:2 | 1:77-1:9 |
| 1 | Bensulfuron-methyl | 1:25-45:1 | 1:8-15:1 | 1:3-3:1 |
| 1 | Bentazone | 1:192-6:1 | 1:64-2:1 | 1:24-1:3 |
| 1 | Benzobicyclon | 1:85-14:1 | 1:28-5:1 | 1:10-1:2 |
| 1 | Benzofenap | 1:257-5:1 | 1:85-2:1 | 1:32-1:4 |
| 1 | Bicyclopyrone | 1:42-27:1 | 1:14-9:1 | 1:5-2:1 |
| 1 | Bifenox | 1:257-5:1 | 1:85-2:1 | 1:32-1:4 |
| 1 | Bispyribac-sodium | 1:10-112:1 | 1:3-38:1 | 1:1-7:1 |
| 1 | Bromacil | 1:384-3:1 | 1:128-1:1 | 1:48-1:6 |
| 1 | Bromobutide | 1:384-3:1 | 1:128-1:1 | 1:48-1:6 |
| 1 | Bromoxynil | 1:96-12:1 | 1:32-4:1 | 1:12-1:2 |
| 1 | Butachlor | 1:768-2:1 | 1:256-1:2 | 1:96-1:11 |
| 1 | Butafenacil | 1:42-27:1 | 1:14-9:1 | 1:5-2:1 |
| 1 | Butylate | 1:1542-1:2 | 1:514-1:5 | 1:192-1:22 |
| 1 | Carfenstrole | 1:192-6:1 | 1:64-2:1 | 1:24-1:3 |
| 1 | Carfentrazone-ethyl | 1:128-9:1 | 1:42-3:1 | 1:16-1:2 |
| 1 | Chlorimuron-ethyl | 1:8-135:1 | 1:2-45:1 | 1:1-9:1 |
| 1 | Chlorotoluron | 1:768-2:1 | 1:256-1:2 | 1:96-1:11 |
| 1 | Chlorsulfuron | 1:6-168:1 | 1:2-56:1 | 1:1-11:1 |
| 1 | Cincosulfuron | 1:17-68:1 | 1:5-23:1 | 1:2-5:1 |
| 1 | Cinidon-ethyl | 1:384-3:1 | 1:128-1:1 | 1:48-1:6 |
| 1 | Cinmethylin | 1:34-34:1 | 1:11-12:1 | 1:4-3:1 |
| 1 | Clacyfos | 1:34-34:1 | 1:11-12:1 | 1:4-3:1 |
| 1 | Clethodim | 1:48-24:1 | 1:16-8:1 | 1:6-2:1 |
| 1 | Clodinafop-propargyl | 1:20-56:1 | 1:6-19:1 | 1:2-4:1 |
| 1 | Clomazone | 1:384-3:1 | 1:128-1:1 | 1:48-1:6 |
| 1 | Clomeprop | 1:171-7:1 | 1:57-3:1 | 1:21-1:3 |
| 1 | Clopyralid | 1:192-6:1 | 1:64-2:1 | 1:24-1:3 |
| 1 | Cloransulam-methyl | 1:12-96:1 | 1:4-32:1 | 1:1-6:1 |
| 1 | Cumyluron | 1:384-3:1 | 1:128-1:1 | 1:48-1:6 |
| 1 | Cyanazine | 1:384-3:1 | 1:128-1:1 | 1:48-1:6 |
| 1 | Cyclopyrimorate | 1:17-68:1 | 1:5-23:1 | 1:2-5:1 |
| 1 | Cyclosulfamuron | 1:17-68:1 | 1:5-23:1 | 1:2-5:1 |
| 1 | Cycloxydim | 1:96-12:1 | 1:32-4:1 | 1:12-1:2 |
| 1 | Cyhalofop | 1:25-45:1 | 1:8-15:1 | 1:3-3:1 |
| 1 | Daimuron | 1:192-6:1 | 1:64-2:1 | 1:24-1:3 |
| 1 | Desmedipham | 1:322-4:1 | 1:107-2:1 | 1:40-1:5 |
| 1 | Dicamba | 1:192-6:1 | 1:64-2:1 | 1:24-1:3 |
| 1 | Dichlobenil | 1:1371-1:2 | 1:457-1:4 | 1:171-1:20 |
| 1 | Dichlorprop | 1:925-2:1 | 1:308-1:3 | 1:115-1:13 |
| 1 | Diclofop-methyl | 1:384-3:1 | 1:128-1:1 | 1:48-1:6 |
| 1 | Diclosulam | 1:10-112:1 | 1:3-38:1 | 1:1-7:1 |
| 1 | Difenzoquat | 1:288-4:1 | 1:96-2:1 | 1:36-1:4 |
| 1 | Difenfenican | 1:857-2:1 | 1:285-1:3 | 1:107-1:12 |
| 1 | Diflufenzopyr | 1:12-96:1 | 1:4-32:1 | 1:1-6:1 |
| 1 | Dimethachlor | 1:768-2:1 | 1:256-1:2 | 1:96-1:11 |
| 1 | Dimethametryn | 1:192-6:1 | 1:64-2:1 | 1:24-1:3 |
| 1 | Dimethenamid-P | 1:384-3:1 | 1:128-1:1 | 1:48-1:6 |

TABLE A1-continued

| Component (a) (Cmpd. No.) | Component (b) | Typical Weight Ratio | More Typical Weight Ratio | Most Typical Weight Ratio |
|---|---|---|---|---|
| 1 | Dithiopyr | 1:192-6:1 | 1:64-2:1 | 1:24-1:3 |
| 1 | Diuron | 1:384-3:1 | 1:128-1:1 | 1:48-1:6 |
| 1 | EPTC | 1:768-2:1 | 1:256-1:2 | 1:96-1:11 |
| 1 | Esprocarb | 1:1371-1:2 | 1:457-1:4 | 1:171-1:20 |
| 1 | Ethalfluralin | 1:384-3:1 | 1:128-1:1 | 1:48-1:6 |
| 1 | Ethametsulfuron-methyl | 1:17-68:1 | 1:5-23:1 | 1:2-5:1 |
| 1 | Ethoxyfen | 1:8-135:1 | 1:2-45:1 | 1:1-9:1 |
| 1 | Ethoxysulfuron | 1:20-56:1 | 1:6-19:1 | 1:2-4:1 |
| 1 | Etobenzanid | 1:257-5:1 | 1:85-2:1 | 1:32-1:4 |
| 1 | Fenoxaprop-ethyl | 1:120-10:1 | 1:40-4:1 | 1:15-1:2 |
| 1 | Fenoxasulfone | 1:85-14:1 | 1:28-5:1 | 1:10-1:2 |
| 1 | Fenquinotrione | 1:17-68:1 | 1:5-23:1 | 1:2-5:1 |
| 1 | Fentrazamide | 1:17-68:1 | 1:5-23:1 | 1:2-5:1 |
| 1 | Flazasulfuron | 1:17-68:1 | 1:5-23:1 | 1:2-5:1 |
| 1 | Florasulam | 1:2-420:1 | 1:1-140:1 | 2:1-27:1 |
| 1 | Fluazifop-butyl | 1:192-6:1 | 1:64-2:1 | 1:24-1:3 |
| 1 | Flucarbazone | 1:8-135:1 | 1:2-45:1 | 1:1-9:1 |
| 1 | Flucetosulfuron | 1:8-135:1 | 1:2-45:1 | 1:1-9:1 |
| 1 | Flufenacet | 1:257-5:1 | 1:85-2:1 | 1:32-1:4 |
| 1 | Flumetsulam | 1:24-48:1 | 1:8-16:1 | 1:3-3:1 |
| 1 | Flumiclorac-pentyl | 1:10-112:1 | 1:3-38:1 | 1:1-7:1 |
| 1 | Flumioxazin | 1:25-45:1 | 1:8-15:1 | 1:3-3:1 |
| 1 | Fluometuron | 1:384-3:1 | 1:128-1:1 | 1:48-1:6 |
| 1 | Flupyrsulfuron-methyl | 1:3-336:1 | 1:1-112:1 | 2:1-21:1 |
| 1 | Fluridone | 1:384-3:1 | 1:128-1:1 | 1:48-1:6 |
| 1 | Fluroxypyr | 1:96-12:1 | 1:32-4:1 | 1:12-1:2 |
| 1 | Flurtamone | 1:857-2:1 | 1:285-1:3 | 1:107-1:12 |
| 1 | Fluthiacet-methyl | 1:48-42:1 | 1:16-14:1 | 1:3-3:1 |
| 1 | Fomesafen | 1:96-12:1 | 1:32-4:1 | 1:12-1:2 |
| 1 | Foramsulfuron | 1:13-84:1 | 1:4-28:1 | 1:1-6:1 |
| 1 | Glufosinate | 1:288-4:1 | 1:96-2:1 | 1:36-1:4 |
| 1 | Glyphosate | 1:288-4:1 | 1:96-2:1 | 1:36-1:4 |
| 1 | Halosulfuron-methyl | 1:17-68:1 | 1:5-23:1 | 1:2-5:1 |
| 1 | Halauxifen | 1:20-56:1 | 1:6-19:1 | 1:2-4:1 |
| 1 | Halauxifen methyl | 1:20-56:1 | 1:6-19:1 | 1:2-4:1 |
| 1 | Haloxyfop-methyl | 1:34-34:1 | 1:11-12:1 | 1:4-3:1 |
| 1 | Hexazinone | 1:192-6:1 | 1:64-2:1 | 1:24-1:3 |
| 1 | Hydantocidin | 1:1100-16:1 | 1:385-8:1 | 1:144-4:1 |
| 1 | Imazamox | 1:13-84:1 | 1:4-28:1 | 1:1-6:1 |
| 1 | Imazapic | 1:20-56:1 | 1:6-19:1 | 1:2-4:1 |
| 1 | Imazapyr | 1:85-14:1 | 1:28-5:1 | 1:10-1:2 |
| 1 | Imazaquin | 1:34-34:1 | 1:11-12:1 | 1:4-3:1 |
| 1 | Imazethabenz-methyl | 1:171-7:1 | 1:57-3:1 | 1:21-1:3 |
| 1 | Imazethapyr | 1:24-48:1 | 1:8-16:1 | 1:3-3:1 |
| 1 | Imazosulfuron | 1:27-42:1 | 1:9-14:1 | 1:3-3:1 |
| 1 | Indanofan | 1:342-4:1 | 1:114-2:1 | 1:42-1:5 |
| 1 | Indaziflam | 1:25-45:1 | 1:8-15:1 | 1:3-3:1 |
| 1 | Iodosulfuron-methyl | 1:3-336:1 | 1:1-112:1 | 2:1-21:1 |
| 1 | Ioxynil | 1:192-6:1 | 1:64-2:1 | 1:24-1:3 |
| 1 | Ipfencarbazone | 1:85-14:1 | 1:28-5:1 | 1:10-1:2 |
| 1 | Isoproturon | 1:384-3:1 | 1:128-1:1 | 1:48-1:6 |
| 1 | Isoxaben | 1:288-4:1 | 1:96-2:1 | 1:36-1:4 |
| 1 | Isoxaflutole | 1:60-20:1 | 1:20-7:1 | 1:7-2:1 |
| 1 | Lactofen | 1:42-27:1 | 1:14-9:1 | 1:5-2:1 |
| 1 | Lenacil | 1:384-3:1 | 1:128-1:1 | 1:48-1:6 |
| 1 | Linuron | 1:384-3:1 | 1:128-1:1 | 1:48-1:6 |
| 1 | MCPA | 1:192-6:1 | 1:64-2:1 | 1:24-1:3 |
| 1 | MCPB | 1:288-4:1 | 1:96-2:1 | 1:36-1:4 |
| 1 | Mecoprop | 1:768-2:1 | 1:256-1:2 | 1:96-1:11 |
| 1 | Mefenacet | 1:384-3:1 | 1:128-1:1 | 1:48-1:6 |
| 1 | Mefluidide | 1:192-6:1 | 1:64-2:1 | 1:24-1:3 |

TABLE A1-continued

| Component (a) (Cmpd. No.) | Component (b) | Typical Weight Ratio | More Typical Weight Ratio | Most Typical Weight Ratio |
|---|---|---|---|---|
| 1 | Mesosulfuron-methyl | 1:5-224:1 | 1:1-75:1 | 1:1-14:1 |
| 1 | Mesotrione | 1:42-27:1 | 1:14-9:1 | 1:5-2:1 |
| 1 | Metamifop | 1:42-27:1 | 1:14-9:1 | 1:5-2:1 |
| 1 | Metazachlor | 1:384-3:1 | 1:128-1:1 | 1:48-1:6 |
| 1 | Metazosulfuron | 1:25-45:1 | 1:8-15:1 | 1:3-3:1 |
| 1 | Methabenzthiazuron | 1:768-2:1 | 1:256-1:2 | 1:96-1:11 |
| 1 | Metolachlor | 1:768-2:1 | 1:256-1:2 | 1:96-1:11 |
| 1 | Metosulam | 1:8-135:1 | 1:2-45:1 | 1:1-9:1 |
| 1 | Metribuzin | 1:192-6:1 | 1:64-2:1 | 1:24-1:3 |
| 1 | Metsulfuron-methyl | 1:2-560:1 | 1:1-187:1 | 3:1-35:1 |
| 1 | Molinate | 1:1028-2:1 | 1:342-1:3 | 1:128-1:15 |
| 1 | Napropamide | 1:384-3:1 | 1:128-1:1 | 1:48-1:6 |
| 1 | Napropamide-M | 1:192-6:1 | 1:64-2:1 | 1:24-1:3 |
| 1 | Naptalam | 1:192-6:1 | 1:64-2:1 | 1:24-1:3 |
| 1 | Nicosulfuron | 1:12-96:1 | 1:4-32:1 | 1:1-6:1 |
| 1 | Norflurazon | 1:1152-1:1 | 1:384-1:3 | 1:144-1:16 |
| 1 | Orbencarb | 1:1371-1:2 | 1:457-1:4 | 1:171-1:20 |
| 1 | Orthosulfamuron | 1:20-56:1 | 1:6-19:1 | 1:2-4:1 |
| 1 | Oryzalin | 1:514-3:1 | 1:171-1:2 | 1:64-1:8 |
| 1 | Oxadiargyl | 1:384-3:1 | 1:128-1:1 | 1:48-1:6 |
| 1 | Oxadiazon | 1:548-3:1 | 1:182-1:2 | 1:68-1:8 |
| 1 | Oxasulfuron | 1:27-42:1 | 1:9-14:1 | 1:3-3:1 |
| 1 | Oxaziclomefone | 1:42-27:1 | 1:14-9:1 | 1:5-2:1 |
| 1 | Oxyfluorfen | 1:384-3:1 | 1:128-1:1 | 1:48-1:6 |
| 1 | Paraquat | 1:192-6:1 | 1:64-2:1 | 1:24-1:3 |
| 1 | Pendimethalin | 1:384-3:1 | 1:128-1:1 | 1:48-1:6 |
| 1 | Penoxsulam | 1:10-112:1 | 1:3-38:1 | 1:1-7:1 |
| 1 | Penthoxamid | 1:384-3:1 | 1:128-1:1 | 1:48-1:6 |
| 1 | Pentoxazone | 1:102-12:1 | 1:34-4:1 | 1:12-1:2 |
| 1 | Phenmedipham | 1:102-12:1 | 1:34-4:1 | 1:12-1:2 |
| 1 | Picloram | 1:96-12:1 | 1:32-4:1 | 1:12-1:2 |
| 1 | Picolinafen | 1:34-34:1 | 1:11-12:1 | 1:4-3:1 |
| 1 | Pinoxaden | 1:25-45:1 | 1:8-15:1 | 1:3-3:1 |
| 1 | Pretilachlor | 1:192-6:1 | 1:64-2:1 | 1:24-1:3 |
| 1 | Primisulfuron-methyl | 1:8-135:1 | 1:2-45:1 | 1:1-9:1 |
| 1 | Prodiamine | 1:384-3:1 | 1:128-1:1 | 1:48-1:6 |
| 1 | Profoxydim | 1:42-27:1 | 1:14-9:1 | 1:5-2:1 |
| 1 | Prometryn | 1:384-3:1 | 1:128-1:1 | 1:48-1:6 |
| 1 | Propachlor | 1:1152-1:1 | 1:384-1:3 | 1:144-1:16 |
| 1 | Propanil | 1:384-3:1 | 1:128-1:1 | 1:48-1:6 |
| 1 | Propaquizafop | 1:48-24:1 | 1:16-8:1 | 1:6-2:1 |
| 1 | Propoxycarbazone | 1:17-68:1 | 1:5-23:1 | 1:2-5:1 |
| 1 | Propyrisulfuron | 1:17-68:1 | 1:5-23:1 | 1:2-5:1 |
| 1 | Propyzamide | 1:384-3:1 | 1:128-1:1 | 1:48-1:6 |
| 1 | Prosulfocarb | 1:1200-1:2 | 1:400-1:4 | 1:150-1:17 |
| 1 | Prosulfuron | 1:6-168:1 | 1:2-56:1 | 1:1-11:1 |
| 1 | Pyraclonil | 1:42-27:1 | 1:14-9:1 | 1:5-2:1 |
| 1 | Pyraflufen-ethyl | 1:5-224:1 | 1:1-75:1 | 1:1-14:1 |
| 1 | Pyrasulfotole | 1:13-84:1 | 1:4-28:1 | 1:1-6:1 |
| 1 | Pyrazolynate | 1:857-2:1 | 1:285-1:3 | 1:107-1:12 |
| 1 | Pyrazosulfuron-ethyl | 1:10-112:1 | 1:3-38:1 | 1:1-7:1 |
| 1 | Pyrazoxyfen | 1:5-224:1 | 1:1-75:1 | 1:1-14:1 |
| 1 | Pyribenzoxim | 1:10-112:1 | 1:3-38:1 | 1:1-7:1 |
| 1 | Pyributicarb | 1:384-3:1 | 1:128-1:1 | 1:48-1:6 |
| 1 | Pyridate | 1:288-4:1 | 1:96-2:1 | 1:36-1:4 |
| 1 | Pyriftalid | 1:10-112:1 | 1:3-38:1 | 1:1-7:1 |
| 1 | Pyriminobac-methyl | 1:20-56:1 | 1:6-19:1 | 1:2-4:1 |
| 1 | Pyrimisulfan | 1:17-68:1 | 1:5-23:1 | 1:2-5:1 |
| 1 | Pyrithiobac | 1:24-48:1 | 1:8-16:1 | 1:3-3:1 |
| 1 | Pyroxasulfone | 1:85-14:1 | 1:28-5:1 | 1:10-1:2 |
| 1 | Pyroxsulam | 1:5-224:1 | 1:1-75:1 | 1:1-14:1 |
| 1 | Quinclorac | 1:192-6:1 | 1:64-2:1 | 1:24-1:3 |
| 1 | Quizalofop-ethyl | 1:42-27:1 | 1:14-9:1 | 1:5-2:1 |

TABLE A1-continued

| Component (a) (Cmpd. No.) | Component (b) | Typical Weight Ratio | More Typical Weight Ratio | Most Typical Weight Ratio |
|---|---|---|---|---|
| 1 | Rimsulfuron | 1:13-84:1 | 1:4-28:1 | 1:1-6:1 |
| 1 | Saflufenacil | 1:25-45:1 | 1:8-15:1 | 1:3-3:1 |
| 1 | Sethoxydim | 1:96-12:1 | 1:32-4:1 | 1:12-1:2 |
| 1 | Simazine | 1:384-3:1 | 1:128-1:1 | 1:48-1:6 |
| 1 | Sulcotrione | 1:120-10:1 | 1:40-4:1 | 1:15-1:2 |
| 1 | Sulfentrazone | 1:147-8:1 | 1:49-3:1 | 1:18-1:3 |
| 1 | Sulfometuron-methyl | 1:34-34:1 | 1:11-12:1 | 1:4-3:1 |
| 1 | Sulfosulfuron | 1:8-135:1 | 1:2-45:1 | 1:1-9:1 |
| 1 | Tebuthiuron | 1:384-3:1 | 1:128-1:1 | 1:48-1:6 |
| 1 | Tefuryltrione | 1:42-27:1 | 1:14-9:1 | 1:5-2:1 |
| 1 | Tembotrione | 1:31-37:1 | 1:10-13:1 | 1:3-3:1 |
| 1 | Tepraloxydim | 1:25-45:1 | 1:8-15:1 | 1:3-3:1 |
| 1 | Terbacil | 1:288-4:1 | 1:96-2:1 | 1:36-1:4 |
| 1 | Terbuthylazine | 1:857-2:1 | 1:285-1:3 | 1:107-1:12 |
| 1 | Terbutryn | 1:192-6:1 | 1:64-2:1 | 1:24-1:3 |
| 1 | Thenylchlor | 1:85-14:1 | 1:28-5:1 | 1:10-1:2 |
| 1 | Thiazopyr | 1:384-3:1 | 1:128-1:1 | 1:48-1:6 |
| 1 | Thiencarbazone | 1:3-336:1 | 1:1-112:1 | 2:1-21:1 |
| 1 | Thifensulfuron-methyl | 1:5-224:1 | 1:1-75:1 | 1:1-14:1 |
| 1 | Tiafenacil | 1:17-68:1 | 1:5-23:1 | 1:2-5:1 |
| 1 | Thiobencarb | 1:768-2:1 | 1:256-1:2 | 1:96-1:11 |
| 1 | Tolpyralate | 1:31-37:1 | 1:10-13:1 | 1:3-3:1 |
| 1 | Topramzone | 1:6-168:1 | 1:2-56:1 | 1:1-11:1 |
| 1 | Tralkoxydim | 1:68-17:1 | 1:22-6:1 | 1:8-2:1 |
| 1 | Triafamone | 1:2-420:1 | 1:1-140:1 | 2:1-27:1 |
| 1 | Triallate | 1:768-2:1 | 1:256-1:2 | 1:96-1:11 |
| 1 | Triasulfuron | 1:5-224:1 | 1:1-75:1 | 1:1-14:1 |
| 1 | Triaziflam | 1:171-7:1 | 1:57-3:1 | 1:21-1:3 |
| 1 | Tribenuron-methyl | 1:3-336:1 | 1:1-112:1 | 2:1-21:1 |
| 1 | Triclopyr | 1:192-6:1 | 1:64-2:1 | 1:24-1:3 |
| 1 | Trifloxysulfuron | 1:2-420:1 | 1:1-140:1 | 2:1-27:1 |
| 1 | Trifludimoxazin | 1:25-45:1 | 1:8-15:1 | 1:3-3:1 |
| 1 | Trifluralin | 1:288-4:1 | 1:96-2:1 | 1:36-1:4 |
| 1 | Triflusulfuron-methyl | 1:17-68:1 | 1:5-23:1 | 1:2-5:1 |
| 1 | Tritosulfuron | 1:13-84:1 | 1:4-28:1 | 1:1-6:1 |

Table A2 is constructed the same as Table A1 above except that entries below the "Component (a)" column heading are replaced with the respective Component (a) Column Entry shown below. Compound 2 in the Component (a) column is identified in Index Table A. Thus, for example, in Table A2 the entries below the "Component (a)" column heading all recite "Compound 2" (i.e. Compound 2 identified in Index Table A), and the first line below the column headings in Table A2 specifically discloses a mixture of Compound 2 with 2,4-D.

| Table Number | Component (a) Column Entries |
|---|---|
| A2 | Compound 2 |
| A3 | Compound 2 |
| A4 | Compound 2 |
| A5 | Compound 2 |
| A6 | Compound 2 |
| A7 | Compound 2 |
| A8 | Compound 2 |

Preferred for better control of undesired vegetation (e.g., lower use rate such as from synergism (enhanced effects), broader spectrum of weeds controlled, or enhanced crop safety) or for preventing the development of resistant weeds are mixtures of a compound of Formula 1 with a herbicide selected from the group consisting of chlorimuron-ethyl, nicosulfuron, mesotrione, thifensulfuron-methyl, flupyrsulfuron-methyl, tribenuron, pyroxasulfone, pinoxaden, tembotrione, pyroxsulam, metolachlor and S-metolachlor.

The following Tests demonstrate the control efficacy of the compounds of this invention against specific weeds. The weed control afforded by the compounds is not limited, however, to these species. See Index Tables A for compound descriptions. The following abbreviations are used in the Index Table which follow: t-Bu is tert-butyl and Ph is phenyl. The abbreviation "Cmpd. No." stands for "Compound Number". The abbreviation "Ex." stands for "Example" and is followed by a number indicating in which example the compound is prepared. $^1$H NMR spectra in INDEX TABLE B are reported in ppm downfield from tetramethylsilane in DMSO $d_6$ at 400 MHz unless otherwise noted; "s" means singlet, "d" means doublet, "t" means triplet, "q" means quartet, "m" means multiplet and "bs" means broad singlet. Mass spectral data are reported with an estimated precision within ±0.5 Da as the molecular weight of the highest isotopic abundance parent ion (M+1) formed by addition of H$^+$ (molecular weight of 1) to the molecule observed by using atmospheric pressure chemical ionization (AP+)

INDEX TABLE A

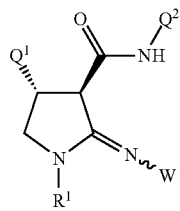

| Cmpd. No. | R¹ | Q¹ | Q² | W | mp (° C.) |
|---|---|---|---|---|---|
| 1 (Ex. 2) | CH₃ | Ph(4-CF₃) | Ph(2,3-di-F) | —NH(C=O)—t-Bu | 240-244 * |
| 2 (Ex. 1) | CH₃ | Ph(4-CF₃) | Ph(2,3-di-F) | —NH₂ | 120-123 * |
| 3 | CH₃ | Ph(4-CF₃) | Ph(2,3-di-F) | —NH(Me) | MS ES+ 427 |
| 4 | CH₃ | Ph(4-CF₃) | Ph(2,3-di-F) | —N(Me)₂ | MS ES+ 441 |
| 5 | CH₃ | Ph(4-CF₃) | Ph(2,3-di-F) | —NH(C=O)Me | MS ES+ 455 |
| 6 | CH₃ | Ph(4-CF₃) | Ph(2,3-di-F) | N-piperidinyl | MS ES+ 481 |
| 7 | CH₃ | Ph(4-CF₃) | Ph(2,3-di-F) | N-morpholinyl | MS ES+ 483 |
| 8 | CH₃ | Ph(4-CF₃) | Ph(2,3-di-F) | —NH(C=O)O—t-Bu | MS ES+ 513 |

\* See Synthesis Example for ¹H NMR data.
\*\* See Index Table B for ¹H NMR data

INDEX TABLE B

| Cmpd. No. | ¹H NMR data |
|---|---|
| 3 | δ 10.66 (s, 1H), 10.31 (s, 1H), 7.80-7.78 (m, 2H), 7.69-7.67 (m, 2H), 7.59-7.56 (m, 1H), 7.26-7.17 (m, 2H), 4.61 (d, 1H), 4.21-4.18 (m, 1H), 4.02 (m, 1H), 3.93-3.89 (m, 1H), 3.13 (s, 3H), 2.48-2.47 (m, 3H). |
| 4 | δ (CDCl₃) 12.05 (s, 1H), 8.15-8.12 (m, 1H), 7.58-7.57 (m, 2H), 7.31-7.30 (m, 2H), 7.07-7.02 (m, 1H), 6.90-6.84 (m, 1H), 4.28-4.26 (m, 1H), 4.02-3.99 (m, 2H), 3.26-3.24 (m, 1H), 2.94 (s, 3H), 2.50 (bs, 6H). |
| 5 | δ 10.13 (s, 1H), 9.54 (s, 1H), 7.72-7.70 (m, 2H), 7.61-7.55 (m, 3H), 7.22-7.16 (m, 2H), 3.98-3.96 (m, 1H), 3.86-3.83 (m, 1H), 3.76-3.73 (m, 1H), 3.40-3.37 (m, 1H), 2.87 (s, 3H), 1.71 (s, 3H). |
| 8 | δ 9.98 (s, 1H), 8.41, (bs, 1H), 7.74-7.70 (m, 3H), 7.58-7.57 (m, 2H), 7.21-7.15 (m, 2H), 4.20-4.19 (m, 1H), 3.83-3.79 (m, 2H), 3.36-3.35 (m, 1H), 2.84 (s, 3H), 1.26 (s, 9H). |

Biological Examples of the Invention

Test A

Seeds of plant species selected from barnyardgrass (*Echinochloa crus-galli*), kochia (*Kochia scoparia*), ragweed (common ragweed, *Ambrosia elatior*), ryegrass, Italian (Italian ryegrass, *Lolium multiflorum*), foxtail, green (green foxtail, *Setaria viridis*), and pigweed (*Amaranthus retroflexus*) were planted into a blend of loam soil and sand and treated preemergence with a directed soil spray using test chemicals formulated in a non-phytotoxic solvent mixture which included a surfactant.

At the same time, plants selected from these weed species and also wheat (*Triticum aestivum*), corn (*Zea mays*), blackgrass (*Alopecurus myosuroides*), and galium (catchweed bedstraw, *Galium aparine*) were planted in pots containing the same blend of loam soil and sand and treated with postemergence applications of test chemicals formulated in the same manner. Plants ranged in height from 2 to 10 cm and were in the one- to two-leaf stage for the postemergence treatment. Treated plants and untreated controls were maintained in a greenhouse for approximately 10 d, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

| | Compounds | | | | | | |
|---|---|---|---|---|---|---|---|
| | 1 | 2 | 3 | 4 | 5 | 7 | 8 |
| 125 g ai/ha Postemergence | | | | | | | |
| Barnyardgrass | 80 | 60 | 70 | 60 | 80 | 50 | 80 |
| Blackgrass | 50 | 30 | 80 | 50 | 80 | 30 | 60 |
| Corn | 40 | 10 | 30 | 20 | 40 | 0 | 70 |
| Foxtail, Giant | — | — | 70 | 80 | 80 | 50 | 80 |
| Foxtail, Green | 80 | 70 | — | — | — | — | — |
| Galium | 10 | 60 | 80 | 70 | 80 | 70 | 70 |
| Kochia | 0 | 0 | 60 | 40 | 30 | 60 | 0 |
| Pigweed | 0 | 40 | 90 | 70 | 80 | 60 | 40 |
| Ragweed | 0 | 0 | 50 | 30 | 0 | 50 | 0 |
| Ryegrass, Italian | 60 | 30 | 40 | 20 | 80 | 30 | 60 |
| Wheat | 30 | 0 | 30 | 20 | 50 | 10 | 40 |
| 31 g ai/ha Postemergence | | | | | | | |
| Barnyardgrass | 40 | 20 | 60 | 0 | 60 | 0 | 60 |
| Blackgrass | 10 | 0 | 40 | 30 | 60 | 30 | 30 |
| Corn | 0 | 10 | 20 | 0 | 0 | 0 | 20 |
| Foxtail, Giant | — | — | 40 | 0 | 70 | 0 | 50 |
| Foxtail, Green | 40 | 30 | — | — | — | — | — |
| Galium | 0 | 60 | 60 | 60 | 70 | 60 | 60 |
| Kochia | 0 | 0 | 20 | 0 | 20 | 0 | 0 |
| Pigweed | 0 | 0 | 0 | 0 | 30 | 0 | 30 |
| Ragweed | 0 | 0 | 0 | 0 | 0 | 0 | 0 |
| Ryegrass, Italian | 20 | 0 | 0 | 0 | 10 | 10 | 10 |

TABLE A-continued

| | Compounds | | | | | | |
|---|---|---|---|---|---|---|---|
| | 1 | 2 | 3 | 4 | 5 | 7 | 8 |
| Wheat 125 g ai/ha Preemergence | 0 | 0 | 0 | 0 | 0 | 0 | 0 |
| Barnyardgrass | 100 | 90 | 90 | 90 | 90 | 50 | 90 |
| Foxtail, Giant | — | — | 90 | 90 | 90 | 90 | 90 |
| Foxtail, Green | 100 | 100 | — | — | — | — | — |
| *Kochia* | 60 | 60 | 30 | 30 | 90 | 20 | 80 |
| Pigweed | 90 | 80 | 70 | 60 | 80 | 10 | 80 |
| Ragweed | 100 | 40 | 0 | 0 | 70 | 0 | 20 |
| Ryegrass, Italian 31 g ai/ha Preemergence | 0 | 0 | 90 | 10 | 90 | 0 | 70 |
| Barnyardgrass | 80 | 70 | 30 | 50 | 90 | 10 | 90 |
| Foxtail, Giant | — | — | 70 | 50 | 90 | 50 | 90 |
| Foxtail, Green | 50 | 70 | — | — | — | — | — |
| *Kochia* | 0 | 0 | 0 | 0 | 10 | 0 | 20 |
| Pigweed | 50 | 0 | 0 | 0 | 70 | 0 | 30 |
| Ragweed | 0 | 0 | 0 | 0 | 0 | 0 | — |
| Ryegrass, Italian | 0 | 0 | 0 | 0 | 20 | 0 | 20 |

Test B

Plant species in the flooded paddy test selected from rice (*Oryza sativa*), sedge, umbrella (small-flower umbrella sedge, *Cyperus difformis*), ducksalad (*Heteranthera limosa*), and barnyardgrass (*Echinochloa crus-galli*) were grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 d, after which time all species were compared to controls and visually evaluated. Plant response ratings, summarized in Table B, are based on a scale of 0 to 100 where 0 is no effect and 100 is complete control. A dash (-) response means no test result.

TABLE B

| | Compounds | | | | | | | |
|---|---|---|---|---|---|---|---|---|
| 250 g ai/ha Flood | 1 | 2 | 3 | 4 | 5 | 7 | 8 | 9 |
| Barnyardgrass | 65 | 40 | 70 | 55 | 45 | 10 | 75 | 75 |
| Ducksalad | 30 | 0 | 100 | 75 | 65 | 45 | 60 | 100 |
| Rice | 0 | 0 | 0 | 0 | 0 | 0 | 0 | 0 |
| Sedge, Umbrella | 0 | 50 | 0 | 0 | 0 | 0 | 0 | 0 |

What is claimed is:

1. A compound of Formula 1, N-oxides salts and stereoisomers thereof

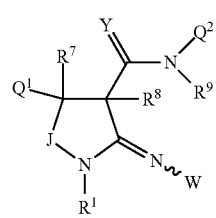

1 wherein
W is —$NR^A R^B$;
$R^A$ is H, cyano, CHO, $C_2$-$C_4$ alkylcarbonyl, $C_1$-$C_4$ alkyl; or phenyl substituted or unsubstituted with halogen or $C_1$-$C_4$ alkyl;

$R^B$ is H, cyano, hydroxy, CHO, $C_1$-$C_6$ alkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl or $C_3$-$C_{10}$ trialkylsilyl; or a phenyl ring or a naphthalenyl ring system, each ring or ring system substituted or unsubstituted with up to 5 substituents independently selected from $R^{16}$; or a 4- to 7-membered heterocyclic ring, substituted or unsubstituted on ring members with up to 5 substituents independently selected from $R^{16}$; or $R^A$ and $R^B$ are taken together along with the nitrogen atom to which they are both bonded to form a 4-, 5- or 6-membered ring containing ring members selected from carbon, oxygen, nitrogen and —C(=O)—; or taken together as a 6- to 10-membered bicyclic ring system; or taken together as an 8- to 13-membered tricyclic ring system, each ring or ring system containing ring members selected from carbon, nitrogen and —C(=O)— and substituted or unsubstituted with halogen, cyano or $C_1$-$C_4$ alkyl;

J is —$CR^2R^3$—, —$CR^2R^3$—$CR^4R^5$—, —$NR^6$— or —O—;

Y is O, S or $NR^{15}$;

$R^1$ is H, hydroxy, amino, cyano, CHO, $C_3$-$C_8$ alkylcarbonylalkyl, —$C(C_1$-$C_4$ alkyl)=N—$O(C_1$-$C_4$ alkyl), —C(O)NH$_2$, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl, $C_3$-$C_8$ cycloalkenyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkenylalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_5$-$C_{10}$ cycloalkylcarbonylalkyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl; or —CPh=N—$O(C_1$-$C_4$ alkyl) where the phenyl is substituted or unsubstituted with up to 5 substituents independently selected from $R^{13}$; or $G^1$;

$Q^1$ is a phenyl ring or a naphthalenyl ring system, each ring or ring system substituted or unsubstituted with up to 5 substituents independently selected from $R^{10}$; or a 4- to 7-membered heterocyclic ring; or an 8- to 10-membered bicyclic ring system, each ring or ring system containing ring members selected from carbon atoms and 1 to 5 heteroatoms independently selected from up to 2 O, up to 2 S and up to 5 N atoms, wherein up to 3 carbon ring members are independently selected from C(=O) and C(=S), and the sulfur atom ring members are independently selected from $S(=O)_u(=NR^{14})_v$, each ring or ring system substituted or unsubstituted with up to 5 substituents independently selected from $R^{10}$ on carbon atom ring members and selected from $R^{12}$ on nitrogen atom ring members;

$Q^2$ is a phenyl ring or a naphthalenyl ring system, each ring or ring system substituted or unsubstituted with up to 5 substituents independently selected from $R^{11}$; or a 4- to 7-membered heterocyclic ring; or an 8- to 10-membered bicyclic ring system, each ring or ring system containing ring members selected from carbon atoms and 1 to 4 heteroatoms independently selected from up to 2 O, up to 2 S and up to 5 N atoms, wherein up to 3 carbon ring members are independently selected from C(=O) and C(=S), and the sulfur atom ring members are independently selected from $S(=O)_u(=NR^{14})_v$, each ring or ring system substituted or unsubstituted with up to 5 substituents independently selected from $R^{11}$ on carbon atom ring members and selected from $R^{13}$ on nitrogen atom ring members;

$R^2$ and $R^3$ are each independently H, halogen, hydroxy, $C_1$-$C_4$ alkyl, $C_1$-$C_4$ haloalkyl or $C_1$-$C_4$ alkoxy; or $R^2$ and $R^3$ are taken together with the carbon atom to which they are bonded to form a $C_3$-$C_7$ cycloalkyl ring;

$R^4$ and $R^5$ are each independently H, halogen, hydroxy, $C_1$-$C_4$ alkyl, $C_1$-$C_4$ haloalkyl or $C_1$-$C_4$ alkoxy;

$R^6$ is H, $C_1$-$C_6$ alkyl or $C_1$-$C_6$ alkoxy; or $R^1$ and $R^6$ are taken together as $C_3$-$C_6$ alkylene or —CH$_2$OCH$_2$—;

$R^7$ and $R^8$ are each independently H, halogen, hydroxy, $C_1$-$C_4$ alkoxy, $C_1$-$C_4$ haloalkyl or $C_1$-$C_4$ alkyl;

$R^9$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_4$-$C_{10}$ cycloalkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl or $C_3$-$C_{10}$ trialkylsilyl; or $G^1$;

each $R^{10}$ and $R^{11}$ is independently halogen, hydroxy, cyano, nitro, amino, $C_1$-$C_8$ alkyl, $C_1$-$C_8$ cyanoalkyl, $C_1$-$C_8$ cyanoalkoxy, $C_1$-$C_8$ haloalkyl, $C_1$-$C_8$ hydroxyalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkynyl, $C_2$-$C_8$ haloalkynyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkoxyhaloalkoxy, $C_3$-$C_6$ cycloalkyl, cyclopropylmethyl, 1-methylcyclopropyl, 2-methylcyclopropyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylamino, $C_2$-$C_8$ dialkylamino, $C_2$-$C_8$ halodialkylamino, $C_2$-$C_8$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_2$-$C_8$ alkylaminocarbonyl, $C_4$-$C_{10}$ cycloalkylaminocarbonyl, $C_3$-$C_{10}$ dialkylaminocarbonyl, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, formylamino, $C_2$-$C_8$ alkylcarbonylamino, $C_2$-$C_8$ haloalkylcarbonylamino, $C_3$-$C_8$ cycloalkylamino, $C_2$-$C_8$ alkoxycarbonylamino, $C_1$-$C_6$ alkylsulfonylamino, $C_1$-$C_6$ haloalkylsulfonylamino, —SF$_5$, —SCN, SO$_2$NH$_2$, $C_3$-$C_{12}$ trialkylsilyl, $C_4$-$C_{12}$ trialkylsilylalkyl or $C_4$-$C_{12}$ trialkylsilylalkoxy; or $G^2$; or $R^{20}S(=O)=N—$, $R^{20}S(=O)_2NR^{19}—C(=O)—$ or $R^{20}(R^{19}N=)_qS(=O)_p—$, wherein the free bond projecting to the right indicates the connecting point to $Q^1$;

each $R^{12}$ and $R^{13}$ is independently cyano, $C_1$-$C_3$ alkyl, $C_1$-$C_8$ hydroxyalkyl, $C_2$-$C_3$ alkenyl, $C_2$-$C_3$ alkynyl, $C_3$-$C_6$ cycloalkyl, $C_2$-$C_3$ alkoxyalkyl, $C_1$-$C_3$ alkoxy, $C_2$-$C_3$ alkylcarbonyl, $C_2$-$C_3$ alkoxycarbonyl, $C_2$-$C_3$ alkylaminoalkyl or $C_3$-$C_4$ dialkylaminoalkyl;

each $R^{14}$ is independently H or C(=O)CH$_3$;

$R^{15}$ is H, cyano, hydroxy, CHO, $C_1$-$C_4$ alkyl, $C_1$-$C_4$ haloalkyl, $C_1$-$C_4$ alkoxy, $C_2$-$C_6$ alkylcarbonyl or $C_2$-$C_6$ haloalkylcarbonyl;

each $G^1$ is independently phenyl; or a 5- or 6-membered heterocyclic ring, each substituted or unsubstituted on ring members with up to 5 substituents independently selected from $R^{17}$;

each $G^2$ is independently phenyl, phenylmethyl, pyridinylmethyl, phenylcarbonyl, phenoxy, phenylethynyl, phenylsulfonyl or a 5- or 6-membered heterocyclic ring, each substituted or unsubstituted on ring members with up to 5 substituents independently selected from $R^{18}$;

each $R^{16}$, $R^{17}$ and $R^{18}$ is independently halogen, cyano, hydroxy, amino, nitro, —CHO, —C(=O)OH, —C(=O)NH$_2$, —SO$_2$NH$_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_1$-$C_8$ hydroxyalkyl, $C_2$-$C_8$ haloalkylcarbonyl, $C_2$-$C_6$ alkoxyalkyl, $C_2$-$C_6$ alkylaminoalkyl, $C_2$-$C_8$ alkoxycarbonyl, $C_3$-$C_8$ cycloalkyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_3$-$C_8$ dialkylaminoalkyl, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_1$-$C_6$ alkylamino, $C_2$-$C_8$ dialkylamino, $C_2$-$C_8$ alkylcarbonylamino, $C_1$-$C_6$ alkylsulfonylamino, phenyl, pyridinyl or thienyl;

each $R^{19}$ is independently H, cyano, $C_2$-$C_3$ alkylcarbonyl or $C_2$-$C_3$ haloalkylcarbonyl;

each $R^{20}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy, $C_3$-$C_{10}$ trialkylsilyl or $G^1$;

each u and v are independently 0, 1 or 2, provided that the sum of u and v is 0, 1 or 2; and each p and q are independently 0, 1 or 2, provided that the sum of u and v is 0, 1 or 2 and when p is 0, q is other than 1 or 2.

2. The compound of claim 1 wherein
$R^A$ is H, cyano, CHO, $C_2$-$C_4$ alkylcarbonyl or $C_1$-$C_4$ alkyl;
$R^B$ is H, CHO, $C_1$-$C_6$ alkyl, $C_2$-$C_6$ alkenyl, $C_3$-$C_6$ alkynyl, $C_2$-$C_8$ alkoxyalkyl, $C_2$-$C_8$ alkylthioalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl or $C_2$-$C_8$ dialkylaminosulfonyl; or a phenyl ring substituted or unsubstituted with up to 5 substituents independently selected from $R^{16}$; or a 5- to 6-membered heterocyclic ring, substituted or unsubstituted on ring members with up to 5 substituents independently selected from $R^{16}$; or
$R^A$ and $R^B$ are taken together along with the nitrogen atom to which they are both bonded to form a 5- or 6-membered ring containing ring members selected from carbon, oxygen, nitrogen and —C(═O)—; or taken together as an 6- to 10-membered bicyclic ring system;
J is —$CR^2R^3$—, —$CR^2R^3$—$CR^4R^5$— or —$NR^6$—;
Y is O or S;
$R^1$ is H, CHO, $C_3$-$C_8$ alkylcarbonylalkyl, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ alkylthioalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_2$-$C_8$ alkylaminocarbonyl, $C_3$-$C_{10}$ dialkylaminocarbonyl or $C_4$-$C_{10}$ cycloalkylaminocarbonyl;
$Q^1$ is a phenyl ring or a naphthalenyl ring system, each ring or ring system substituted or unsubstituted with up to 5 substituents independently selected from $R^{10}$; or a 5- to 6-membered heterocyclic ring; or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 2 carbon ring members are independently selected from C(═O) and C(═S), and the sulfur atom ring members are independently selected from S(═O)$_u$ (═$NR^{14}$)$_v$, each ring or ring system substituted or unsubstituted with up to 4 substituents independently selected from $R^{10}$ on carbon atom ring members and selected from $R^{12}$ on nitrogen atom ring members;
$Q^2$ is a phenyl ring, each ring substituted or unsubstituted with up to 4 substituents independently selected from $R^{11}$; or a 5- to 6-membered heterocyclic ring; or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 2 carbon ring members are independently selected from C(═O) and C(═S), and the sulfur atom ring members are independently selected from S(═O)$_u$ (═$NR^{14}$)$_v$, each ring or ring system substituted or unsubstituted with up to 4 substituents independently selected from $R^{11}$ on carbon atom ring members and selected from $R^{13}$ on nitrogen atom ring members;
$R^2$ and $R^3$ are each independently H or $C_1$-$C_4$ alkyl;
$R^4$ and $R^5$ are each independently H, halogen, $C_1$-$C_4$ alkyl or $C_1$-$C_4$ alkoxy;
$R^6$ is H, $C_1$-$C_6$ alkyl or $C_1$-$C_6$ alkoxy;
$R^7$ and $R^8$ are each independently H, halogen, $C_1$-$C_4$ alkoxy or $C_1$-$C_4$ alkyl;
$R^9$ is H, $C_1$-$C_6$ alkyl, $C_2$-$C_8$ alkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_4$-$C_{10}$ cycloalkylcarbonyl, $C_2$-$C_8$ alkoxycarbonyl or $C_4$-$C_{10}$ cycloalkoxycarbonyl;
each $R^{10}$ and $R^{11}$ is halogen, nitro, $C_1$-$C_8$ alkyl, $C_1$-$C_8$ cyanoalkyl, $C_1$-$C_8$ cyanoalkoxy, $C_1$-$C_8$ haloalkyl, $C_1$-$C_8$ nitroalkyl, $C_2$-$C_8$ alkenyl, $C_2$-$C_8$ haloalkenyl, $C_2$-$C_g$ nitroalkenyl, $C_2$-$C_8$ alkoxyalkyl, $C_3$-$C_8$ alkoxyalkyl, $C_2$-$C_8$ haloalkoxyalkyl, $C_2$-$C_8$ haloalkoxyhaloalkoxy, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_2$-$C_8$ alkylcarbonyl, $C_2$-$C_8$ haloalkylcarbonyl, $C_4$-$C_{10}$ cycloalkylcarbonyl, —C(═O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(═O)$NH_2$, $C_1$-$C_8$ alkoxy, $C_1$-$C_8$ haloalkoxy, $C_2$-$C_8$ alkenyloxy, $C_2$-$C_8$ haloalkenyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylsulfonyl, $C_1$-$C_8$ haloalkylsulfonyl, $C_3$-$C_8$ cycloalkylsulfonyl;
each $R^{12}$ and $R^{13}$ is independently $C_1$-$C_3$ alkyl, $C_2$-$C_3$ alkenyl, $C_3$-$C_6$ cycloalkyl, $C_2$-$C_3$ alkoxyalkyl, $C_2$-$C_3$ alkylcarbonyl or $C_2$-$C_3$ alkylaminoalkyl;
each $R^{14}$ is independently H or —(C═O)$CH_3$;
each $R^{16}$ is independently halogen, cyano, hydroxy, amino, nitro, —CHO, —C(═O)OH, —C(═O)$NH_2$, —$SO_2NH_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_1$-$C_8$ hydroxyalkyl, $C_2$-$C_8$ haloalkylcarbonyl, $C_2$-$C_6$ alkoxyalkyl, $C_2$-$C_6$ alkylaminoalkyl, $C_2$-$C_8$ alkoxycarbonyl, $C_3$-$C_8$ cycloalkyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_3$-$C_8$ dialkylaminoalkyl, $C_1$-$C_6$ alkoxy, $C_1$-$C_6$ haloalkoxy, $C_2$-$C_8$ alkylcarbonyloxy or $C_1$-$C_6$ alkylthio; and
the sum of u and v is 2.

3. The compound of claim 2 wherein
$R^A$ is H, CHO, $C_2$-$C_4$ alkylcarbonyl or $C_1$-$C_4$ alkyl;
$R^B$ is H, $C_1$-$C_6$ alkyl, $C_2$-$C_8$ alkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl or $C_2$-$C_8$ dialkylaminosulfonyl; or a phenyl ring substituted or unsubstituted with up to 4 substituents independently selected from $R^{16}$; or $R^A$ and $R^B$ are taken together along with the nitrogen atom to which they are both bonded to form a 5- or 6-membered ring containing ring members selected from carbon, oxygen and —C(=O)—; or taken together as a 6- to 10-membered bicyclic ring system;

J is —$CR^2R^3$— or —$CR^2R^3$—$CR^4R^5$—;

Y is O;

$R^1$ is H, $C_3$-$C_8$ alkylcarbonylalkyl, $C_1$-$C_6$ alkyl, $C_1$-$C_6$ haloalkyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_2$-$C_8$ haloalkoxyalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl or $C_2$-$C_8$ haloalkoxycarbonyl;

$Q^1$ is a phenyl ring substituted or unsubstituted with up to 4 substituents independently selected from $R^{10}$; or a 5- to 6-membered heterocyclic ring, each ring containing ring members selected from carbon atoms and 1 to 4 heteroatoms independently selected from up to 2 O, up to 2 S and up to 4 N atoms, each ring substituted or unsubstituted with up to 4 substituents independently selected from $R^{10}$ on carbon atom ring members and selected from $R^{12}$ on nitrogen atom ring members;

$Q^2$ is a phenyl ring, substituted or unsubstituted with up to 4 substituents independently selected from $R^{11}$; or a 5- to 6-membered heterocyclic ring; or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 2 carbon ring members are independently selected from C(=O) and C(=S), and the sulfur atom ring members are independently selected from S(=O)$_u$(=NR$^{14}$)$_v$, each ring or ring system substituted or unsubstituted with up to 4 substituents independently selected from $R^{11}$ on carbon atom ring members and selected from $R^{13}$ on nitrogen atom ring members;

$R^2$ and $R^3$ are each independently H or $CH_3$;

$R^4$ and $R^5$ are each independently H, halogen or $C_1$-$C_4$ alkyl;

$R^7$ and $R^8$ are each independently H, F, Cl or $CH_3$;

$R^9$ is H, $C_1$-$C_6$ alkyl, $C_2$-$C_8$ alkoxyalkyl, $C_2$-$C_8$ alkylcarbonyl or $C_2$-$C_8$ alkoxycarbonyl;

each $R^{10}$ and $R^{11}$ is independently halogen, $C_1$-$C_8$ alkyl, $C_1$-$C_8$ haloalkyl, $C_2$-$C_8$ alkoxyalkyl, $C_3$-$C_8$ alkoxyalkoxyalkyl, $C_4$-$C_{10}$ cycloalkylalkyl, $C_5$-$C_{12}$ alkylcycloalkylalkyl, $C_3$-$C_8$ cycloalkyl, $C_3$-$C_8$ halocycloalkyl, $C_6$-$C_{12}$ cycloalkylcycloalkyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_1$-$C_8$ alkoxy, $C_1$-$C_8$ haloalkoxy, $C_2$-$C_8$ haloalkenyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy or $C_2$-$C_8$ haloalkylcarbonyloxy;

each $R^{12}$ and $R^{13}$ is independently $C_1$-$C_3$ alkyl, $C_3$-$C_6$ cycloalkyl or $C_2$-$C_3$ alkylcarbonyl;

each $R^{14}$ is independently H; and each $R^{16}$ is independently halogen, cyano, hydroxy, amino, nitro, —CHO, —C(=O)OH, —C(=O)NH$_2$, —SO$_2$NH$_2$, $C_1$-$C_6$ alkyl or $C_1$-$C_6$ haloalkyl.

4. The compound of claim 3 wherein $R^A$ is H or $C_1$-$C_4$ alkyl;

$R^B$ is H, $C_1$-$C_6$ alkyl, $C_2$-$C_8$ alkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl or $C_2$-$C_8$ dialkylaminosulfonyl; or a phenyl ring substituted or unsubstituted with up to 3 substituents independently selected from $R^{16}$;

$R^A$ and $R^B$ are taken together along with the nitrogen atom to which they are both bonded to form a 5-membered ring containing ring members selected from carbon and oxygen; or taken together as a 6- to 9-membered bicyclic ring system;

J is —$CR^2R^3$—;

$R^1$ is H, $C_1$-$C_6$ alkyl, $C_1$-$C_6$ haloalkyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_2$-$C_8$ haloalkoxyalkyl or $C_2$-$C_8$ alkoxycarbonyl;

$Q^1$ is a phenyl ring substituted or unsubstituted with up to 4 substituents independently selected from $R^{10}$;

$Q^2$ is a phenyl ring, substituted or unsubstituted with up to 4 substituents independently selected from $R^{11}$;

$R^2$ and $R^3$ are each independently H or $CH_3$;

$R^7$ and $R^8$ are each independently H or $CH_3$;

$R^9$ is H, $C_1$-$C_6$ alkyl or $C_2$-$C_8$ alkoxycarbonyl;

each $R^{10}$ and $R^{11}$ is independently halogen, $C_1$-$C_8$ alkyl, $C_1$-$C_8$ haloalkyl, $C_2$-$C_8$ alkoxyalkyl, $C_4$-$C_{10}$ cycloalkylalkyl, $C_5$-$C_{12}$ alkylcycloalkylalkyl, $C_3$-$C_8$ cycloalkyl, $C_3$-$C_8$ halocycloalkyl, $C_2$-$C_8$ haloalkoxyalkoxy, $C_1$-$C_8$ alkoxy, $C_1$-$C_8$ haloalkoxy or $C_2$-$C_8$ alkoxyalkoxy;

each $R^{12}$ and $R^{13}$ is independently $C_1$-$C_3$ alkyl or $C_2$-$C_3$ alkylcarbonyl; and each $R^{16}$ is independently halogen, nitro, $C_1$-$C_6$ alkyl or $C_1$-$C_6$ haloalkyl.

5. The compound of claim 4 wherein $R^A$ is H or $CH_3$;

$R^B$ is H, $C_2$-$C_8$ alkylcarbonyl, $C_4$-$C_{10}$ cycloalkylcarbonyl, $C_2$-$C_8$ alkoxycarbonyl or $C_4$-$C_{10}$ cycloalkoxycarbonyl; or a phenyl ring substituted or unsubstituted with up to 3 substituents independently selected from $R^{16}$;

$R^1$ is H, $C_1$-$C_6$ alkyl, $C_3$-$C_6$ cycloalkyl, $C_4$-$C_8$ cycloalkylalkyl or $C_2$-$C_8$ alkoxyalkyl;

$Q^1$ is a phenyl ring substituted or unsubstituted with up to 3 substituents independently selected from $R^{10}$;

$Q^2$ is a phenyl ring, substituted or unsubstituted with up to 3 substituents independently selected from $R^{11}$;

$R^2$ and $R^3$ are each independently H;

$R^7$ and $R^8$ are each independently H or F;

$R^9$ is H, $CH_3$ or —C(=O)OCH$_3$;

each $R^{10}$ and $R^{11}$ is independently halogen, $C_1$-$C_8$ alkyl, $C_1$-$C_8$ haloalkyl, $C_1$-$C_8$ alkoxy or $C_1$-$C_8$ haloalkoxy; and each $R^{16}$ is independently halogen, $C_1$-$C_6$ alkyl or $C_1$-$C_6$ haloalkyl.

6. The compound of claim 4 wherein $R^A$ and $R^B$ are taken together along with the nitrogen atom to which they are both bonded to form a 5- or 6-membered ring containing ring members selected from carbon and oxygen and —C(=O)—; or taken together as a 6- to 10-membered bicyclic ring system selected from the group consisting of W-1 through W-13

W-1

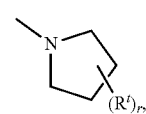

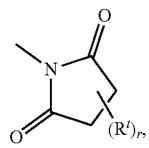
W-2

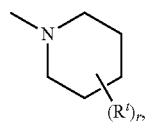
W-3

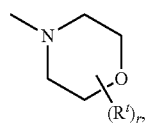
W-4

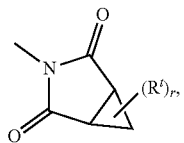
W-5

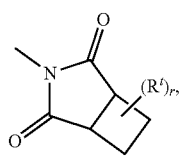
W-6

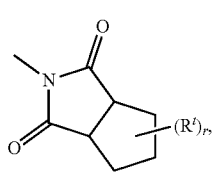
W-7

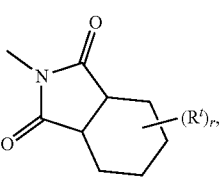
W-8

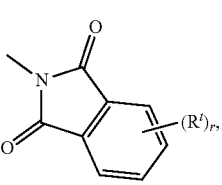
W-9

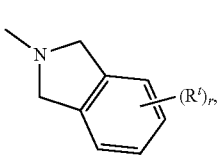
W-10

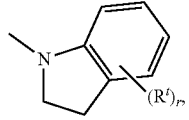
W-11

W-12 and

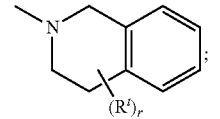
W-13;

$R^t$ is halogen, cyano or $C_1$-$C_4$ alkyl;
r is 0 to 4;
$Q^1$ is a phenyl ring substituted or unsubstituted with up to 3 substituents independently selected from $R^{10}$;
$Q^2$ is a phenyl ring, substituted or unsubstituted with up to 3 substituents independently selected from $R^{11}$;
$R^2$ and $R^3$ are each independently H;
$R^7$ and $R^8$ are each independently H;
$R^9$ is H, $CH_3$ or —C(=O)OCH$_3$;
each $R^{10}$ and $R^{11}$ is independently halogen, $C_1$-$C_8$ alkyl, $C_1$-$C_8$ haloalkyl, $C_1$-$C_8$ alkoxy or $C_1$-$C_8$ haloalkoxy; and
each $R^{16}$ is independently halogen, $C_1$-$C_6$ alkyl or $C_1$-$C_6$ haloalkyl.

7. The compound of claim 6 wherein
$R^A$ and $R^B$ are taken together as a 8- to 9-membered bicyclic ring system selected from W-7, W-8 and W-9;
$R^t$ is halogen or $C_1$-$C_4$ alkyl;
r is 0 to 3;
$Q^1$ is a phenyl ring substituted or unsubstituted with up to 2 substituents independently selected from $R^{10}$;
$Q^2$ is a phenyl ring, substituted or unsubstituted with up to 2 substituents independently selected from $R^{11}$;
$R^9$ is H; and
each $R^{10}$ and $R^{11}$ is independently halogen or $C_1$-$C_8$ haloalkyl.

8. A compound of claim 1 that is
2-[(3R,4S)-3-[[(2,3-difluorophenyl)amino]carbonyl]-1-methyl-4-[4-(trifluoromethyl)phenyl]-2-pyrrolidinylidene]hydrazide 2,2-dimethylpropanoic acid.

9. A herbicidal composition comprising a compound of claim 1 and further comprising at least one component selected from the group consisting of surfactants, solid diluents and liquid diluents.

10. A herbicidal composition comprising a compound of claim 1, and further comprising at least one additional active ingredient selected from the group consisting of other herbicides and herbicide safeners, and at least one component selected from the group consisting of surfactants, solid diluents and liquid diluents.

11. A herbicidal mixture comprising a compound of claim 1, and at least one additional active ingredient selected from photosystem II inhibitors, acetohydroxy acid synthase inhibitors, acetyl-CoA carboxylase inhibitors, auxin mimics, 5-enol-pyruvylshikimate-3-phosphate synthase inhibitors, photosystem I electron diverters, protoporphyrinogen oxidase inhibitors, glutamine synthetase inhibitors, very long chain fatty acid elongase inhibitors, auxin transport inhibitors, phytoene desaturase inhibitors, 4-hydroxyphenyl-pyruvate dioxygenase inhibitors, homogentisate solanesyltransferase inhibitors, cellulose biosynthesis inhibitors, mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid, pyributicarb and herbicide safeners; and salts thereof.

12. A method for controlling the growth of undesired vegetation comprising contacting the vegetation or its environment with a herbicidally effective amount of a compound of claim 1.

* * * * *